United States Patent
Christou et al.

(10) Patent No.: US 12,303,870 B2
(45) Date of Patent: May 20, 2025

(54) COMPOSITIONS AND METHODS RELATING TO MOLECULAR CERIUM-OXIDE NANOCLUSTERS

(71) Applicant: University of Florida Research Foundation, Inc., Gainesville, FL (US)

(72) Inventors: George Christou, Gainesville, FL (US); Kylie J. Mitchell, Pennington, NJ (US)

(73) Assignee: University of Florida Research Foundation, INC., Gainesville, FL (US)

( * ) Notice: Subject to any disclaimer, the term of this patent is extended or adjusted under 35 U.S.C. 154(b) by 758 days.

(21) Appl. No.: 17/528,678

(22) Filed: Nov. 17, 2021

(65) Prior Publication Data

US 2022/0072512 A1    Mar. 10, 2022

Related U.S. Application Data

(63) Continuation of application No. 16/467,088, filed as application No. PCT/US2017/064890 on Dec. 6, 2017, now Pat. No. 11,207,663.

(60) Provisional application No. 62/579,217, filed on Oct. 31, 2017, provisional application No. 62/430,484, filed on Dec. 6, 2016.

(51) Int. Cl.
| | |
|---|---|
| *B01J 23/10* | (2006.01) |
| *A61K 33/244* | (2019.01) |
| *A61P 39/06* | (2006.01) |
| *C01F 17/235* | (2020.01) |
| *C01F 17/30* | (2020.01) |

(52) U.S. Cl.
CPC .............. *B01J 23/10* (2013.01); *A61K 33/244* (2019.01); *A61P 39/06* (2018.01); *C01F 17/235* (2020.01); *C01F 17/30* (2020.01); *C01P 2002/77* (2013.01); *C01P 2004/64* (2013.01)

(58) Field of Classification Search
CPC ........ B01J 23/10; A61P 39/06; A61K 33/244; C01F 17/30; C01F 17/235; C01P 2002/77; C01P 2004/64
See application file for complete search history.

(56) References Cited

PUBLICATIONS

Okamoto et al. Determination of Nanocluster Sizes from Dark-Field Scanning Transmission Electron Microscopy Images. J. Phys. Chem. C, 2008, 112(6):1759-1763. (Year: 2008).*
Flytzani-Stephanopoulos, Maria. "Nanostructured cerium oxide "Ecocatalysts"." Mrs Bulletin 26.11 (2001): 885-889.
Trovarelli, Alessandro. "Catalytic properties of ceria and CeO2-containing materials." Catalysis Reviews 38.4 (1996): 439-520.
Murray, E. Perry, T. Tsai, and Scott A. Barnett. "A direct-methane fuel cell with a ceria-based anode." Nature 400.6745 (1999): 649-651.
Kharton, V. V., et al. "Ceria-based materials for solid oxide fuel cells." Journal of Materials Science 36.5 (2001): 1105-1117.
Sun, Chunwen, Hong Li, and Liquan Chen. "Nanostructured ceria-based materials: synthesis, properties, and applications." Energy & Environmental Science 5.9 (2012): 8475-8505.
Reed, Kenneth, et al. "Exploring the properties and applications of nanoceria: is there still plenty of room at the bottom?." Environmental Science: Nano 1.5 (2014): 390-405.
Perullini, Mercedes, Sara A. Aldabe Bilmes, and Matías Jobbágy. "Cerium oxide nanoparticles: Structure, applications, reactivity, and eco-toxicology." Nanomaterials: a danger or a promise?. Springer, London, 2013. 307-333.
Carrettin, Silvio, et al. "Nanocrystalline CeO2 increases the activity of Au for CO oxidation by two orders of magnitude." Angewandte Chemie International Edition 43.19 (2004): 2538-2540.
Tabakova, T., et al. "A comparative study of nanosized IB/ceria catalysts for low-temperature water-gas shift reaction." Applied Catalysis A: General 298 (2006): 127-143.
Lee, Seung Soo, et al. "Antioxidant properties of cerium oxide nanocrystals as a function of nanocrystal diameter and surface coating." ACS nano 7.11 (2013): 9693-9703.
Das, Soumen, et al. "Cerium oxide nanoparticles: applications and prospects in nanomedicine." Nanomedicine 8.9 (2013): 1483-1508.
Walkey, Carl, et al. "Catalytic properties and biomedical applications of cerium oxide nanoparticles." Environmental Science: Nano 2.1 (2015): 33-53.
Xu, Can, and Xiaogang Qu. "Cerium oxide nanoparticle: a remarkably versatile rare earth nanomaterial for biological applications." NPG Asia materials 6.3 (2014): e90-e90.
Spulber, M., et al. "Ceria loaded nanoreactors: a nontoxic superantioxidant system with high stability and efficacy." Nanoscale 7.4 (2015): 1411-1423.
Nelson, Bryant C., et al. "Antioxidant cerium oxide nanoparticles in biology and medicine." Antioxidants 5.2 (2016): 15.

(Continued)

*Primary Examiner* — Robert A Wax
*Assistant Examiner* — Olga V. Tcherkasskaya
(74) *Attorney, Agent, or Firm* — Thomas | Horstemeyer LLP

(57) ABSTRACT

Described herein are compositions and methods relating to molecular cerium-oxide nanoclusters. In an aspect, described herein are methods of synthesizing molecular cerium-oxide nanocluster compositions and compositions thereof. In an aspect, described herein are methods of scavenging reactive oxygen species utilizing molecular cerium-oxide nanoclusters as described herein. Also described herein are pharmaceutical compositions and methods of use. Pharmaceutical compositions as described herein can comprise a therapeutically effective amount of a compound (such as a composition comprising one or more molecular cerium-oxide nanoclusters), or a pharmaceutically acceptable salt of the compound, and a pharmaceutically acceptable carrier. Methods of treating oxidative stress are also described herein, comprising administering pharmaceutical compositions as described herein to a subject in need thereof. This abstract is intended as a scanning tool for purposes of searching in the particular art and is not intended to be limiting of the present disclosure.

9 Claims, 47 Drawing Sheets

(56) References Cited

PUBLICATIONS

Pulido-Reyes, Gerardo, et al. "Untangling the biological effects of cerium oxide nanoparticles: the role of surface valence states." Scientific reports 5.1 (2015): 1-14.
Pirmohamed, Talib, et al. "Nanoceria exhibit redox state-dependent catalase mimetic activity." Chemical communications 46.16 (2010): 2736-2738.
Karakoti, A. S., et al. "Nanoceria as antioxidant: synthesis and biomedical applications." Jom 60.3 (2008): 33-37.
Wason, Melissa S., and Jihe Zhao. "Cerium oxide nanoparticles: potential applications for cancer and other diseases." American journal of translational research 5.2 (2013): 126.
Gao, Ying, et al. "Cerium oxide nanoparticles in cancer." OncoTargets and therapy 7 (2014): 835.
Barnham, Kevin J., Colin L. Masters, and Ashley I. Bush. "Neurodegenerative diseases and oxidative stress." Nature reviews Drug discovery 3.3 (2004): 205-214.
Kim, Chi Kyung, et al. "Ceria nanoparticles that can protect against ischemic stroke." Angewandte Chemie International Edition 51.44 (2012): 11039-11043.
Kwon, Hyek Jin, et al. "Mitochondria-targeting ceria nanoparticles as antioxidants for Alzheimer's disease." ACS nano 10.2 (2016): 2860-2870.
Grulke, Eric, et al. "Nanoceria: factors affecting its pro-and anti-oxidant properties." Environmental Science: Nano 1.5 (2014): 429-444.
Das, Mainak, et al. "Auto-catalytic ceria nanoparticles offer neuroprotection to adult rat spinal cord neurons." Biomaterials 28.10 (2007): 1918-1925.
Chen, Junping, et al. "Rare earth nanoparticles prevent retinal degeneration induced by intracellular peroxides." Nature nanotechnology 1.2 (2006): 142-150.
Tarnuzzer, Roy W., et al. "Vacancy engineered ceria nanostructures for protection from radiation-induced cellular damage." Nano letters 5.12 (2005): 2573-2577.
Schubert, David, et al. "Cerium and yttrium oxide nanoparticles are neuroprotective." Biochemical and biophysical research communications 342.1 (2006): 86-91.
Xu, P. T., et al. "Cerium oxide nanoparticles: a potential medical countermeasure to mitigate radiation-induced lung injury in CBA/J mice." Radiation research 185.5 (2016): 516-526.
Ouyang, Zi, et al. "Potential of using cerium oxide nanoparticles for protecting healthy tissue during accelerated partial breast irradiation (APBI)." Physica Medica 32.4 (2016): 631-635.
Alpaslan, Ece, et al. "pH-dependent activity of dextran-coated cerium oxide nanoparticles on prohibiting osteosarcoma cell proliferation." ACS Biomaterials Science & Engineering 1.11 (2015): 1096-1103.
Ni, Pan, et al. "On the origin of the oxidizing ability of ceria nanoparticles." RSC advances 5.118 (2015): 97512-97519.
Xue, Ying, et al. "Direct evidence for hydroxyl radical scavenging activity of cerium oxide nanoparticles." The Journal of Physical Chemistry C 115.11 (2011): 4433-4438.
Lu, Mei, et al. "Insight into several factors that affect the conversion between antioxidant and oxidant activities of nanoceria." ACS applied materials & interfaces 8.36 (2016): 23580-23590.
Asati, Atul, et al. "Oxidase-like activity of polymer-coated cerium oxide nanoparticles." Angewandte Chemie 121.13 (2009): 2344-2348.
Van der Sluis, P. V., and A. L. Spek. "Bypass: an effective method for the refinement of crystal structures containing disordered solvent regions." Acta Crystallographica Section A: Foundations of Crystallography 46.3 (1990): 194-201.
Spek, A. L. "Platon/Squeeze." Acta Crystallogr., Sect. D: Biol. Crystallogr 65 (2009): 148-155.
Mereacre, Valeriu, et al. "Homo-and Heterovalent Polynuclear Cerium and Cerium/Manganese Aggregates." Helvetica Chimica Acta 92.11 (2009): 2507-2524.
Das, Rajorshi, Rupam Sarma, and Jubaraj B. Baruah. "A hexanuclear cerium (IV) cluster with mixed coordination environment." Inorganic Chemistry Communications 13.6 (2010): 793-795.
Hennig, Christoph, et al. "Crystal structure and solution species of Ce (III) and Ce (IV) formates: From mononuclear to hexanuclear complexes." Inorganic chemistry 52.20 (2013): 11734-11743.
Calvez, Guillaume, et al. "A New Series of Anhydrous Lanthanide-Based Octahedral Hexanuclear Complexes." (2009): 3172-3178.
Mathey, Laurent, et al. "Cerium (IV) hexanuclear clusters from cerium (III) precursors: Molecular models for oxidative growth of ceria nanoparticles." Chemistry—A European Journal 21.38 (2015): 13454-13461.
Estes, Shanna L., Mark R. Antonio, and L. Soderholm. "Tetravalent Ce in the nitrate-decorated hexanuclear cluster [Ce6 (μ3-O) 4 (μ3-OH) 4] 12+: a structural end point for ceria nanoparticles." The Journal of Physical Chemistry C 120.10 (2016): 5810-5818.
Babu, Suresh, et al. "Electron paramagnetic study on radical scavenging properties of ceria nanoparticles." Chemical Physics Letters 442.4-6 (2007): 405-408.
Schlick, Shulamith, et al. "Scavenging of hydroxyl radicals by ceria nanoparticles: effect of particle size and concentration." The Journal of Physical Chemistry C 120.12 (2016): 6885-6890.
Zhang, Yan, et al. "Crystal plane effects of nano-CeO 2 on its antioxidant activity." Rsc Advances 4.92 (2014): 50325-50330.
Gagnon, Jacinthe, and Katharina M. Fromm. "Toxicity and protective effects of cerium oxide nanoparticles (nanoceria) depending on their preparation method, particle size, cell type, and exposure route." European Journal of Inorganic Chemistry 2015.27 (2015): 4510-4517.

* cited by examiner

  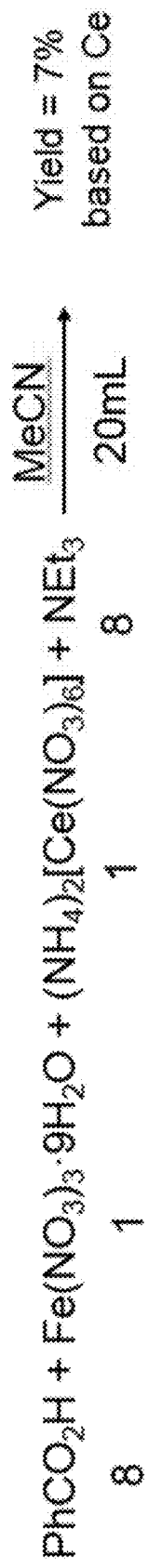  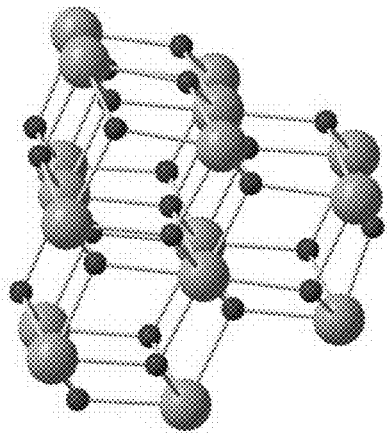
[Ce$_{16}$O$_{17}$(OH)$_6$(O$_2$CPh)$_{24}$(HO$_2$CPh)$_3$(H$_2$O)]
FIG. 3A
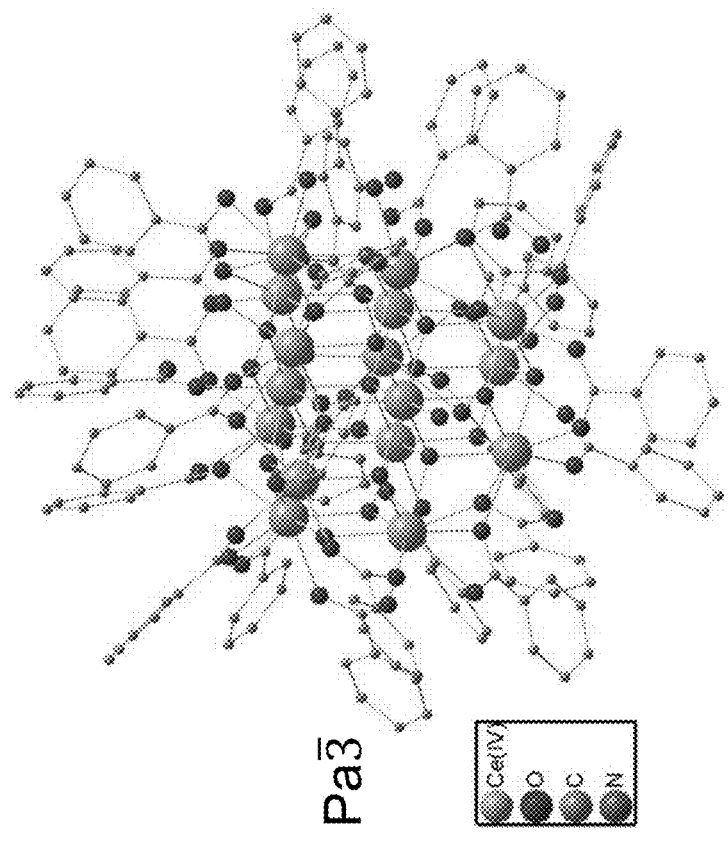
FIG. 3B
FIG. 3C

[Ce$_{24}$O$_{28}$(OH)$_8$(PhCO$_2$)$_{30}$(py)$_4$]

Yield = 11% based on Ce (NH$_4$)$_2$[Ce(NO$_3$)$_6$] + PhCO$_2$H
1    2

P 2$_1$/n

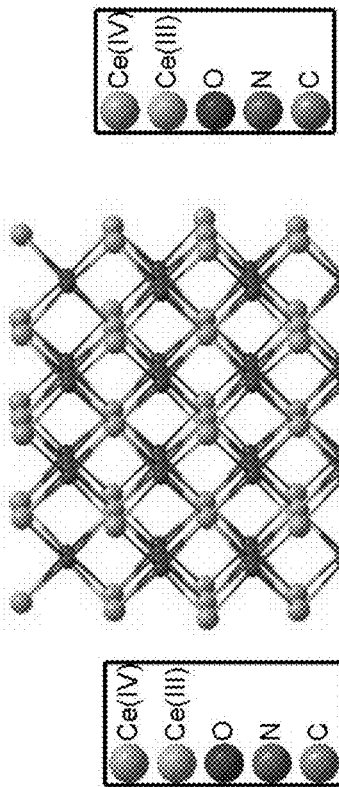
FIG. 5A
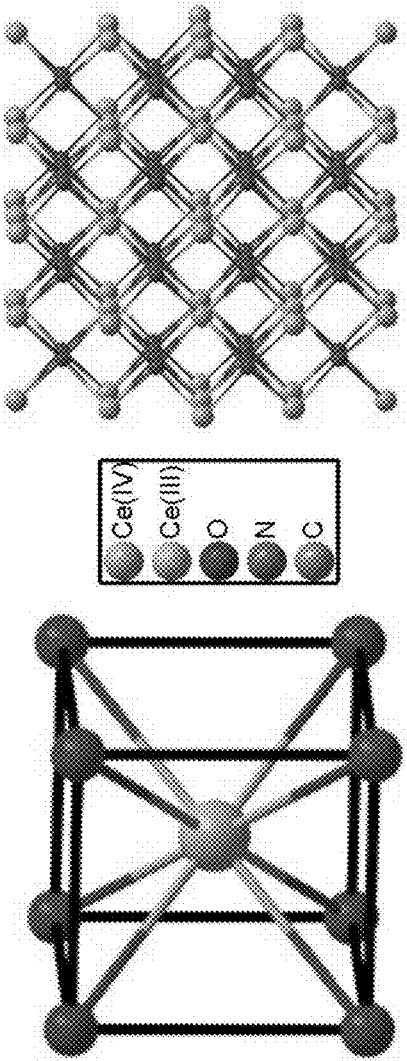
FIG. 5B
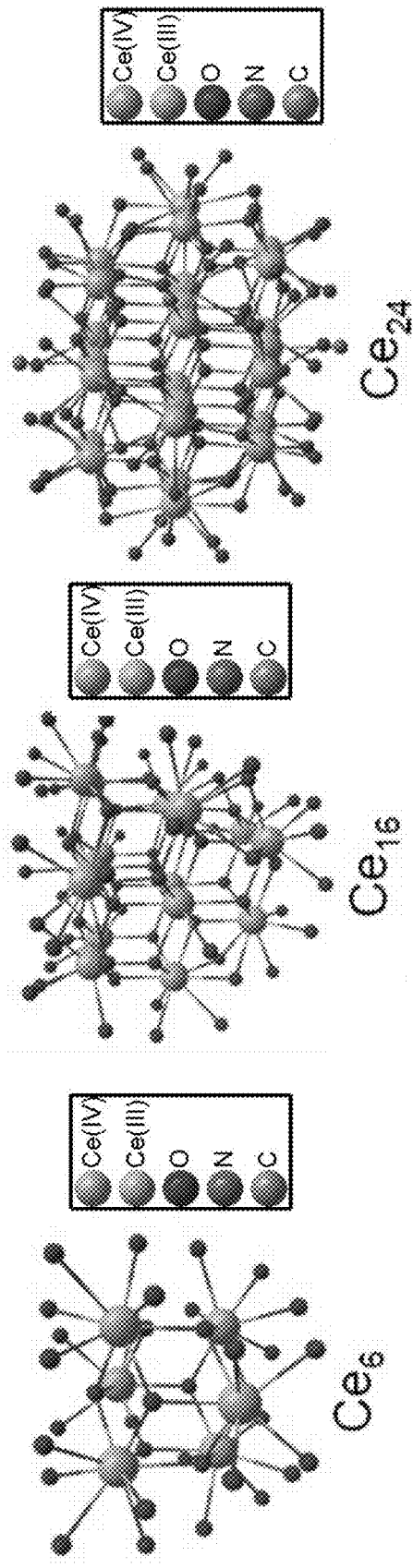
FIG. 5C
FIG. 5D
FIG. 5E

1 = solvent

1 = solvent
2 = crystallization agent

1 = solvent

1 = solvent
2 = crystallization agent

|      | Ce³⁺ | Ce⁴⁺ |      | Ce³⁺ | Ce⁴⁺ |
|------|------|------|------|------|------|
| Ce1  | 4.06 | 3.56 | Ce11 | 4.80 | 4.21 |
| Ce2  | 3.12 | 2.74 | Ce12 | 4.33 | 3.81 |
| Ce3  | 4.58 | 4.02 | Ce13 | 4.51 | 3.96 |
| Ce4  | 4.47 | 3.92 | Ce14 | 4.55 | 3.99 |
| Ce5  | 4.31 | 3.79 | Ce15 | 4.88 | 4.28 |
| Ce6  | 4.52 | 3.97 | Ce16 | 4.54 | 3.98 |
| Ce7  | 4.54 | 3.98 | Ce17 | 3.14 | 2.76 |
| Ce8  | 4.15 | 3.64 | Ce18 | 3.25 | 2.85 |
| Ce9  | 4.53 | 3.98 | Ce19 | 3.08 | 2.70 |
| Ce10 | 4.56 | 4.00 |      |      |      |

$[Ce_{19}O_{18}(OH)_9(PhCO_2)_{27}(py)_3(H_2O)]$

| | O.S. | C.N. | $O^{2-}$ | $OH^-$ |
|---|---|---|---|---|
| Ce14 | +4 | 9 | 3 | 2 |
| Ce15 | +4 | 9 | 3 | 2 |
| Ce16 | +4 | 9 | 3 | 2 |
| Ce17 | +3 | 9 | 2 | 1 |
| Ce18 | +3 | 9 | 2 | 1 |
| Ce19 | +3 | 9 | 2 | 1 |

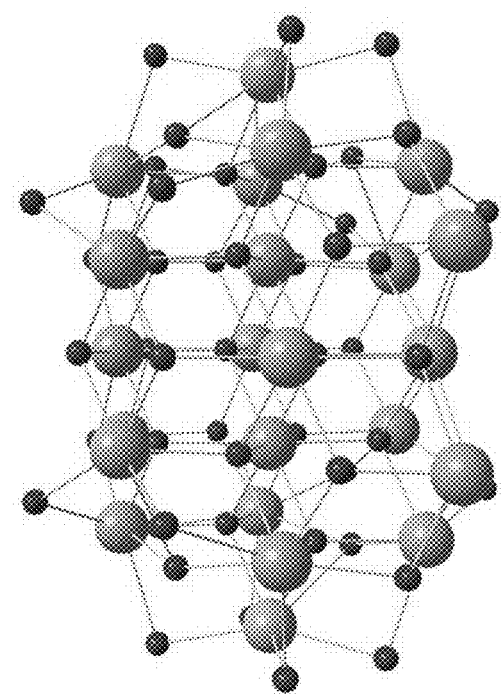
$Ce(NO_3)_3 \quad + \quad PhCO_2H \xrightarrow[10\ mL]{py}$
1      2
MeCN added for crystallization
Yield = 30% based on Ce
FIG. 13A
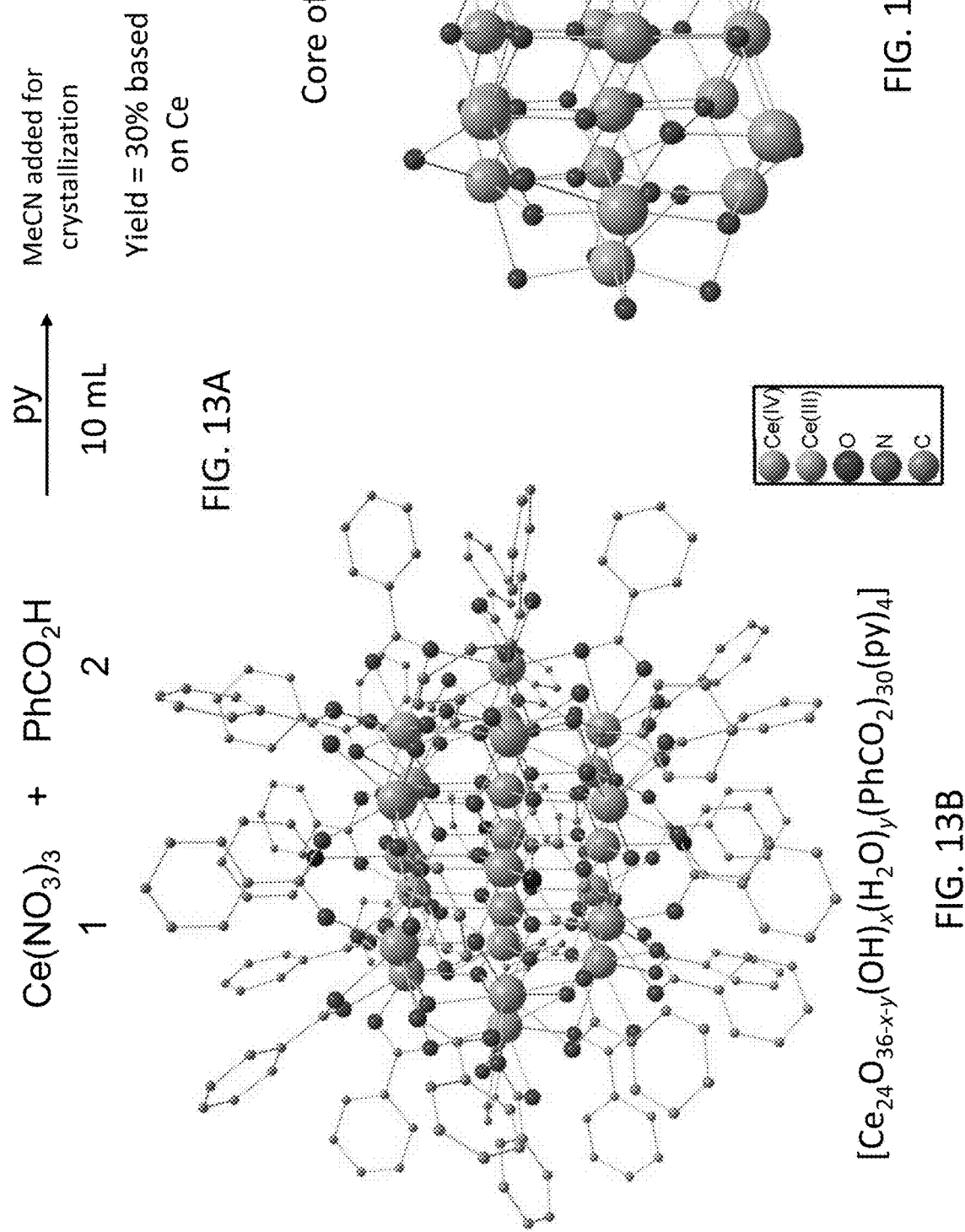
$[Ce_{24}O_{36-x-y}(OH)_x(H_2O)_y(PhCO_2)_{30}(py)_4]$
FIG. 13B
Core of $Ce_{24}$
FIG. 13C BVS Calculations for Ce$_{24}$

| | BVS | Assignment |
|---|---|---|
| O1 | 1.92 | O$^{2-}$ |
| O2 | 1.90 | O$^{2-}$ |
| O3 | 1.87 | O$^{2-}$ |
| O4 | 2.13 | O$^{2-}$ |
| O5 | 2.17 | O$^{2-}$ |
| O6 | 1.97 | O$^{2-}$ |
| O7 | 2.12 | O$^{2-}$ |
| O8 | 1.82 | O$^{2-}$ |
| O9 | 2.09 | O$^{2-}$ |
| O10 | 2.06 | O$^{2-}$ |

FIG. 15A

| | BVS | Assignment |
|---|---|---|
| O11 | 2.13 | O$^{2-}$ |
| O12 | 0.57 | OH$^-$/H$_2$O |
| O13 | 1.95 | O$^{2-}$ |
| O14 | 0.57 | OH$^-$/H$_2$O |
| O15 | 1.23 | OH$^-$ |
| O16 | 1.22 | OH$^-$ |
| O17 | 1.91 | O$^{2-}$ |
| O19 | 1.64 | O$^{2-}$ |

FIG. 15B

| $Ce_{38}a$ | CN | $Ce^3$ | $Ce^4$ |
|---|---|---|---|
| Ce1 | 9 | 4.29 | 3.76 |
| Ce2 | 8 | 4.45 | 3.91 |
| Ce3 | 9 | 4.39 | 3.86 |
| Ce4 | 8 | 4.62 | 4.06 |
| Ce5 | 8 | 4.62 | 4.06 |
| Ce6 | 9 | 4.36 | 3.83 |
| Ce7 | 8 | 4.38 | 3.85 |
| Ce8 | 9 | 4.27 | 3.75 |
| Ce9 | 9 | 4.33 | 3.80 |
| Ce10 | 8 | 4.43 | 3.89 |
| Ce11 | 9 | 4.71 | 4.13 |

FIG. 17A

| $Ce_{38}b$ | CN | $Ce^3$ | $Ce^4$ |
|---|---|---|---|
| Ce21 | 9 | 4.19 | 3.70 |
| Ce22 | 8 | 4.45 | 3.91 |
| Ce23 | 9 | 4.35 | 3.82 |
| Ce24 | 9 | 4.18 | 3.67 |
| Ce25 | 8 | 4.50 | 3.95 |
| Ce26 | 8 | 4.64 | 4.07 |
| Ce27 | 9 | 4.51 | 3.96 |
| Ce28 | 8 | 4.50 | 3.95 |
| Ce29 | 8 | 4.55 | 4.00 |
| Ce30 | 9 | 4.52 | 3.97 |
| Ce31 | 9 | 4.54 | 3.98 |
| Ce32 | 9 | 4.84 | 4.25 |
| Ce33 | 9 | 4.87 | 4.27 |

| O | BVS | Assignment |
|---|---|---|
| O1 | 1.93 | $O^{2-}$ |
| O3 | 1.86 | $O^{2-}$ |
| O4 | 2.14 | $O^{2-}$ |
| O7 (2) | 0.57 | $OH/H_2O$ |
| O9 | 2.13 | $O^{2-}$ |
| O10 | 2.11 | $O^{2-}$ |
| O11 | 2.00 | $O^{2-}$ |
| O12 | 2.04 | $O^{2-}$ |
| O13 | 2.11 | $O^{2-}$ |
| O14 | 1.97 | $O^{2-}$ |
| O15 | 2.11 | $O^{2-}$ |
| O16 | 1.90 | $O^{2-}$ |
| O17 | 2.12 | $O^{2-}$ |
| O18 | 1.71 | $O^{2-}$ |
| O27 (4) | 0.57 | $OH/H_2O$ |
| O28 | 2.10 | $O^{2-}$ |
| O29 | 1.86 | $O^{2-}$ |
| O30 | 1.91 | $O^{2-}$ |
| O39 (2) | 1.52 | $OH/H_2O$ |

| O | BVS | Assignment |
|---|---|---|
| O42 (2) | 0.52 | $OH/H_2O$ |
| O45 | 2.12 | $O^{2-}$ |
| O49 | 1.65 | $O^{2-}$ |
| O50 | 2.12 | $O^{2-}$ |
| O54 | 2.11 | $O^{2-}$ |
| O59 | 1.86 | $O^{2-}$ |
| O60 | 1.72 | $O^{2-}$ |
| O63 | 2.03 | $O^{2-}$ |
| O64 (2) | 0.57 | $OH/H_2O$ |
| O69 | 1.91 | $O^{2-}$ |
| O70 | 2.15 | $O^{2-}$ |
| O71 | 2.10 | $O^{2-}$ |
| O72 | 1.99 | $O^{2-}$ |
| O73 | 2.12 | $O^{2-}$ |
| O74 | 1.96 | $O^{2-}$ |
| O75 (2) | 0.58 | $OH/H_2O$ |
| O79 | 1.89 | $O^{2-}$ |

FIG. 18B

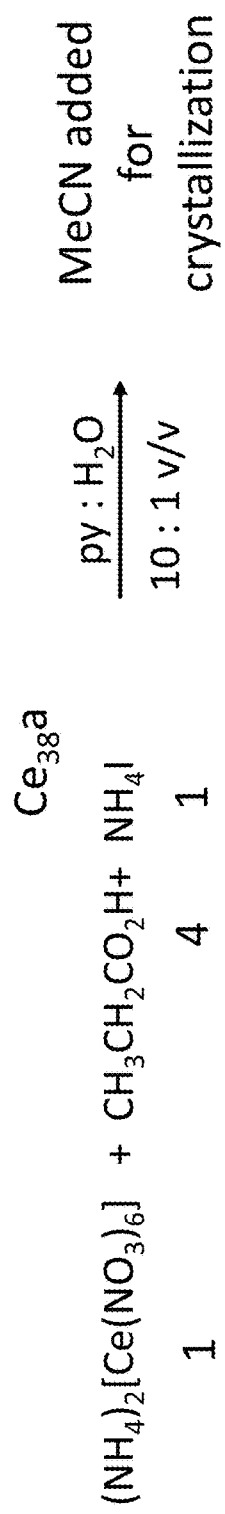
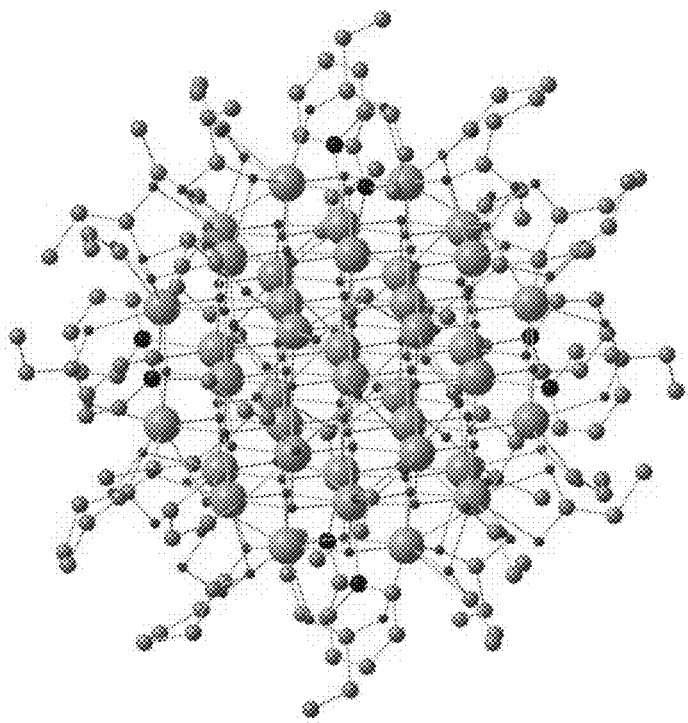
Ce$_{38}$a
(NH$_4$)$_2$[Ce(NO$_3$)$_6$] + CH$_3$CH$_2$CO$_2$H + NH$_4$I
1          4         1
$\xrightarrow{\text{py : H}_2\text{O} \;\; 10:1\;v/v}$
MeCN added for crystallization
Yield = 49% based on Ce
Core of Ce$_{38}$a
OH$^-$/H$_2$O shown in purple
FIG. 19A
FIG. 19C
Ce$_{38}$O$_{62-x-y}$(OH)$_x$(H$_2$O)$_y$(CH$_3$CH$_2$CO$_2$)$_{36}$(py)$_8$
FIG. 19B $Ce_{38}b$ – this is the second molecule in the asymmetric unit
$(NH_4)_2[Ce(NO_3)_6] + CH_3CH_2CO_2H + NH_4I \xrightarrow[10:1 \, v/v]{py:H_2O}$
4      1      1
MeCN added for crystallization
Yield = 49% based on Ce
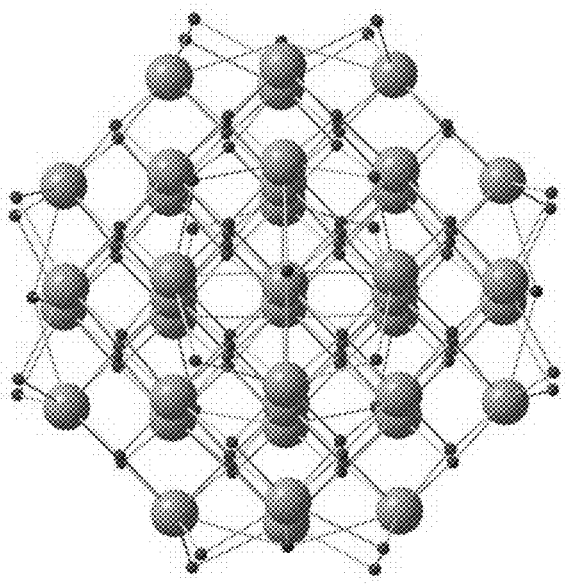
Core of $Ce_{38}b$
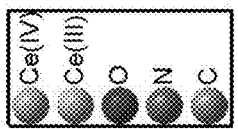
$OH^-/H_2O$ shown in purple
FIG. 20A
FIG. 20C
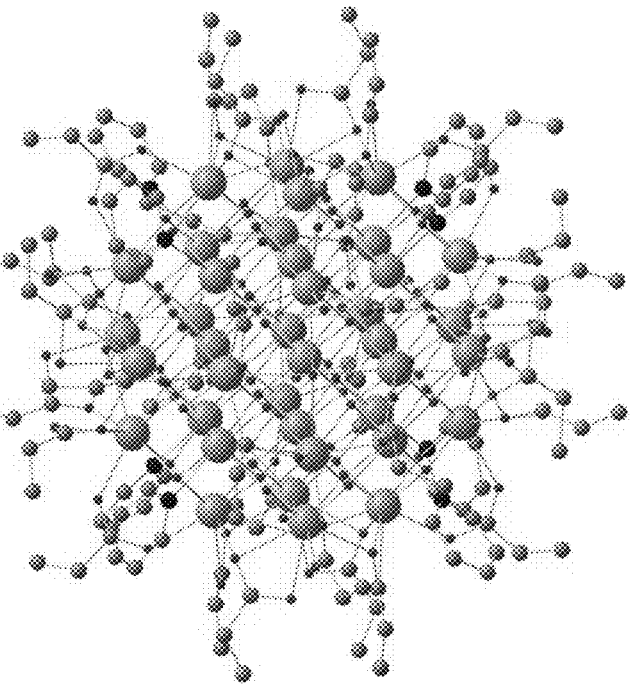
$Ce_{38}O_{62-x-y}(OH)_x(H_2O)_y(CH_3CH_2CO_2)_{36}(py)_8$
FIG. 20B

Ce38a

| Ce | C.N. | O.S. | O | OH/H₂O |
|---|---|---|---|---|
| Ce1 | 9 | 4+ | 4 | 1 |
| Ce2 | 8 | 4+ | 7 | 0 |
| Ce3 | 9 | 4+ | 4 | 1 |
| Ce4 | 8 | 4+ | 8 | 0 |
| Ce5 | 8 | 4+ | 8 | 0 |
| Ce6 | 9 | 4+ | 4 | 1 |
| Ce7 | 8 | 4+ | 6 | 1 |
| Ce8 | 9 | 4+ | 4 | 1 |
| Ce9 | 9 | 4+ | 4 | 1 |
| Ce10 | 8 | 4+ | 7 | 0 |
| Ce11 | 9 | 4+ | 3 | 2 |

| Ce | C.N. | O.S. | O | OH/H₂O |
|---|---|---|---|---|
| Ce21 | 9 | 4+ | 4 | 1 |
| Ce22 | 8 | 4+ | 7 | 0 |
| Ce23 | 9 | 4+ | 4 | 1 |
| Ce24 | 9 | 4+ | 4 | 1 |
| Ce25 | 8 | 4+ | 8 | 0 |
| Ce26 | 8 | 4+ | 8 | 0 |
| Ce27 | 9 | 4+ | 4 | 1 |
| Ce28 | 8 | 4+ | 7 | 0 |
| Ce29 | 8 | 4+ | 8 | 0 |
| Ce30 | 9 | 4+ | 4 | 1 |
| Ce31 | 9 | 4+ | 4 | 1 |
| Ce32 | 9 | 4+ | 4 | 1 |
| Ce33 | 9 | 4+ | 4 | 1 |

FIG. 22B

| Ce | C.N. | Ce-O | Ce-O |
|---|---|---|---|
| Ce1 | 9 | 4.40 | 3.86 |
| Ce2 | 8 | 4.37 | 3.84 |
| Ce3 | 9 | 4.39 | 3.85 |
| Ce4 | 8 | 4.46 | 3.92 |
| Ce5 | 8 | 4.63 | 4.07 |
| Ce6 | 8 | 4.43 | 3.89 |
| Ce7 | 8 | 4.31 | 3.79 |
| Ce8 | 9 | 4.33 | 3.81 |
| Ce9 | 9 | 4.58 | 4.02 |
| Ce10 | 8 | 4.25 | 3.74 |
| Ce11 | 8 | 4.21 | 3.69 |
| Ce12 | 7 | 4.36 | 3.83 |
| Ce13 | 10 | 2.81 | 2.47 |

FIG. 23A

| Ce | C.N. | Ce-O | Ce-O |
|---|---|---|---|
| Ce21 | 8 | 4.41 | 3.87 |
| Ce22 | 7 | 4.24 | 3.73 |
| Ce23 | 9 | 4.34 | 3.81 |
| Ce24 | 8 | 4.06 | 3.56 |
| Ce25 | 8 | 4.66 | 4.09 |
| Ce26 | 8 | 4.31 | 3.78 |
| Ce27 | 8 | 4.14 | 3.64 |
| Ce28 | 8 | 4.23 | 3.71 |
| Ce29 | 8 | 4.47 | 3.93 |
| Ce30 | 9 | 4.39 | 3.86 |
| Ce31 | 10 | 3.20 | 2.81 |
| Ce32 | 8 | 4.46 | 3.91 |
| Ce33 | 9 | 4.49 | 3.95 |

| | BVS | Assignment |
|---|---|---|
| O41 | 1.95 | O²⁻ |
| O42 | 2.09 | O²⁻ |
| O43 | 2.07 | O²⁻ |
| O44 | 2.00 | O²⁻ |
| O45 | 2.00 | O²⁻ |
| O46 | 2.00 | O²⁻ |
| O47 | 2.07 | O²⁻ |
| O48 | 2.18 | O²⁻ |
| O49 | 1.90 | O²⁻ |
| O50 | 1.97 | O²⁻ |
| O51 | 1.85 | O²⁻ |
| O52 | 1.86 | O²⁻ |
| O53 | 1.95 | O²⁻ |
| O54 | 2.14 | O²⁻ |
| O55 | 1.98 | O²⁻ |
| O57 | 0.64 | OH⁻/H₂O |

| | BVS | Assignment |
|---|---|---|
| O1 | 2.14 | O²⁻ |
| O2 | 2.09 | O²⁻ |
| O4 | 0.64 | OH⁻/H₂O |
| O5 | 2.00 | O²⁻ |
| O6 | 1.98 | O²⁻ |
| O7 | 1.88 | O²⁻ |
| O8 | 2.06 | O²⁻ |
| O9 | 2.10 | O²⁻ |
| O10 | 2.06 | O²⁻ |
| O11 | 2.01 | O²⁻ |
| O12 | 1.88 | O²⁻ |
| O13 | 1.99 | O²⁻ |
| O14 | 1.94 | O²⁻ |
| O15 | 1.94 | O²⁻ |
| O16 | 2.00 | O²⁻ |
| O17 | 2.06 | O²⁻ |

FIG. 24A $Ce_{40}a$

MeCN added for crystallization

Yield = 27% based on Ce $(NH_4)_2[Ce(NO_3)_6] + CH_3CO_2H + NH_4I$ 1  4  1

$\xrightarrow[10:1\ v/v]{py:H_2O}$

Core of $Ce_{40}a$ $OH^-/H_2O$ shown in purple $Ce_{40}O_{56}(OH)_x(H_2O)_{2-x}(CH_3CO_2)_{46-y}(py)_4(MeCN)_y$ Ce$_{40}$b – this is the second molecule in the asymmetric unit $(NH_4)_2[Ce(NO_3)_6]$ + $CH_3CO_2H$ + $NH_4I$ $\xrightarrow[10:1\ v/v]{py:H_2O}$ MeCN added for crystallization

1 : 4 : 1

Yield = 27% based on Ce

Core of Ce$_{40}$b

OH$^-$/H$_2$O shown in purple

Ce$_{40}$O$_{56}$(OH)$_x$(H$_2$O)$_{2-x}$(CH$_3$CO$_2$)$_{46-y}$(py)$_4$(MeCN)$_y$

Ce₄₀a

| Ce | CN | O S | O C | OH/H₂O |
|---|---|---|---|---|
| Ce1 | 9 | 4+ | 4 | 1 |
| Ce2 | 8 | 4+ | 7 | 0 |
| Ce3 | 9 | 4+ | 4 | 0 |
| Ce4 | 8 | 4+ | 8 | 0 |
| Ce5 | 8 | 4+ | 8 | 0 |
| Ce6 | 8 | 4+ | 4 | 0 |
| Ce7 | 8 | 4+ | 8 | 0 |
| Ce8 | 9 | 4+ | 4 | 1 |
| Ce9 | 9 | 4+ | 4 | 0 |
| Ce10 | 8 | 4+ | 4 | 0 |
| Ce11 | 8 | 4+ | 4 | 0 |
| Ce12 | 7 | 4+ | 4 | 0 |
| Ce13 | 10 | 3+ | 2 | 1 |

| Ce | CN | O S | O C | OH/H₂O |
|---|---|---|---|---|
| Ce21 | 8 | 4+ | 4 | 0 |
| Ce22 | 7 | 4+ | 4 | 0 |
| Ce23 | 9 | 4+ | 4 | 0 |
| Ce24 | 8 | 4+ | 4 | 0 |
| Ce25 | 8 | 4+ | 8 | 0 |
| Ce26 | 8 | 4+ | 8 | 0 |
| Ce27 | 8 | 4+ | 4 | 0 |
| Ce28 | 8 | 4+ | 7 | 0 |
| Ce29 | 8 | 4+ | 8 | 0 |
| Ce30 | 9 | 4+ | 5 | 1 |
| Ce31 | 10 | 3+ | 2 | 1 |
| Ce32 | 8 | 4+ | 4 | 0 |
| Ce33 | 9 | 4+ | 4 | 1 |

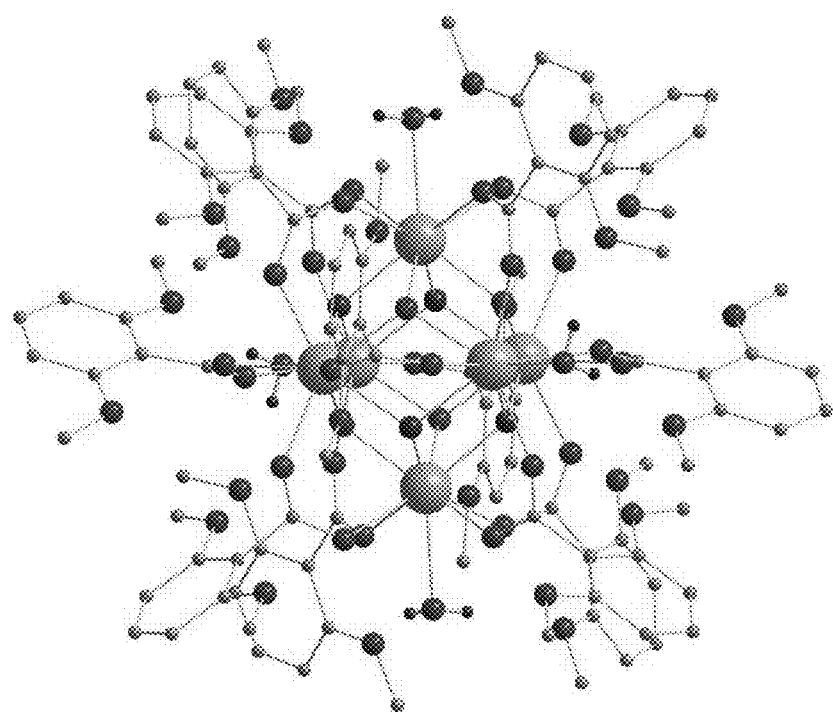
FIG. 38A
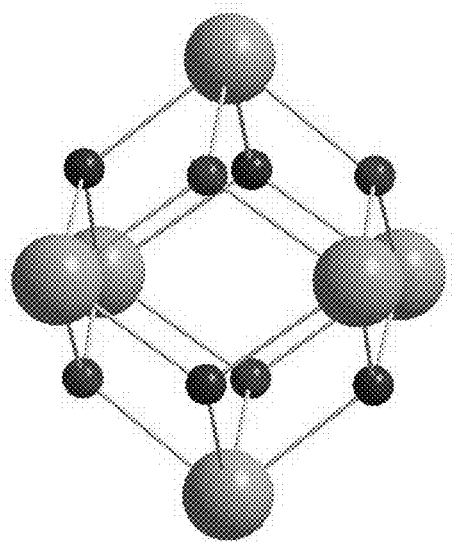 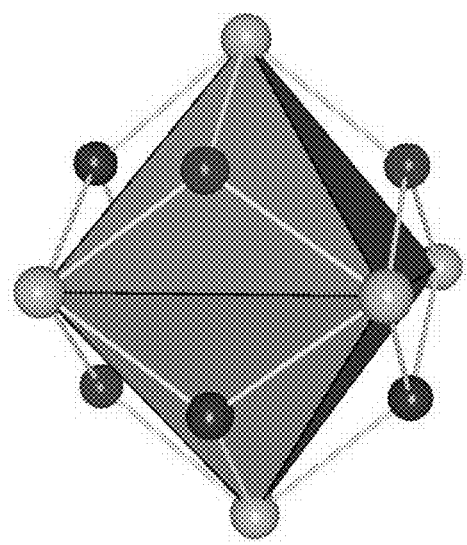
FIG. 38B　　　　　　　　　　　FIG. 38C

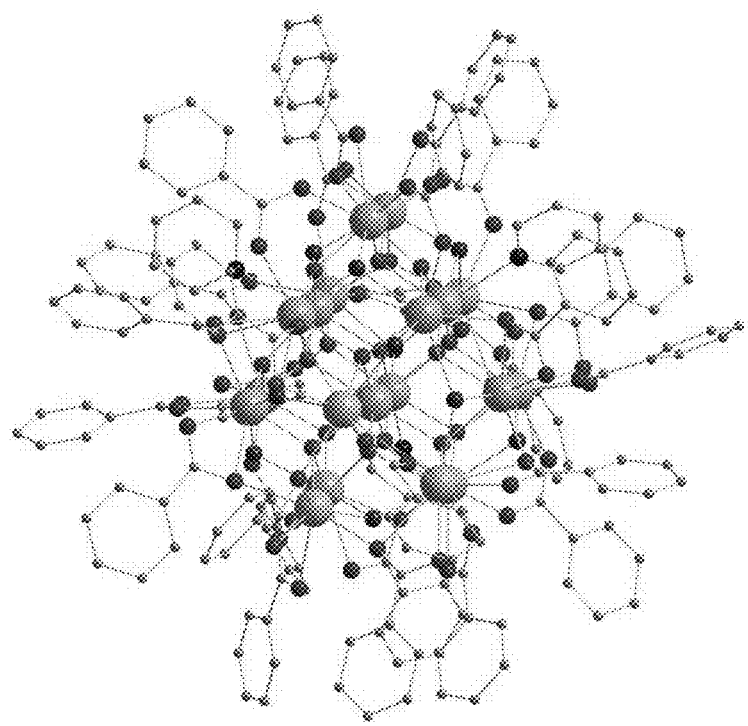
FIG. 40A
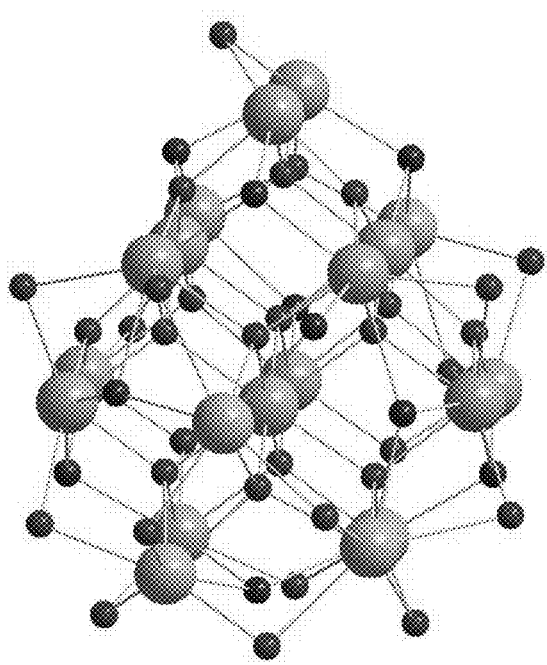 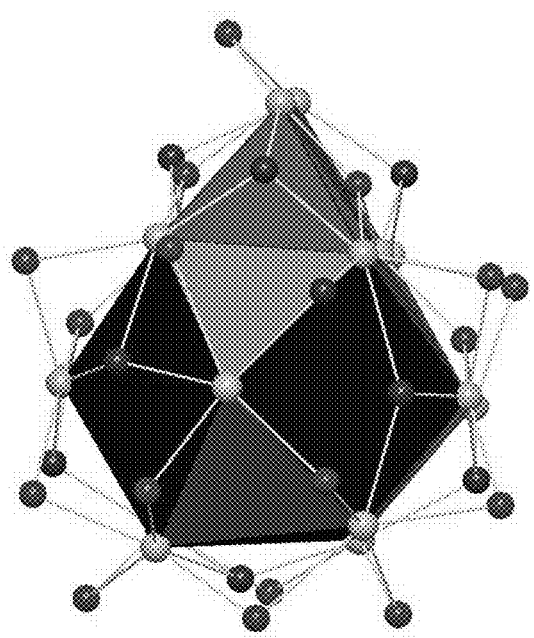
FIG. 40B  FIG. 40C

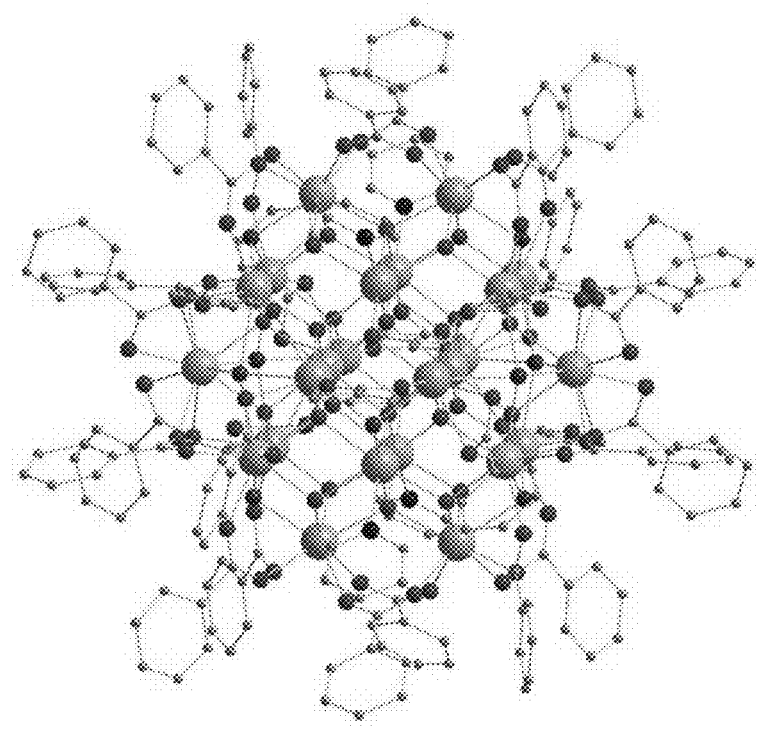
FIG. 41A
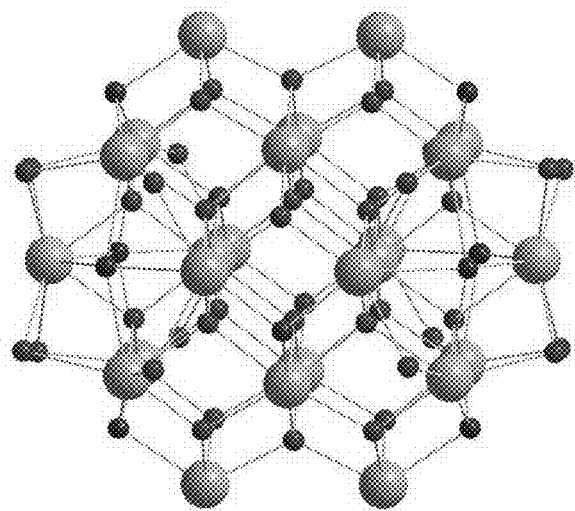 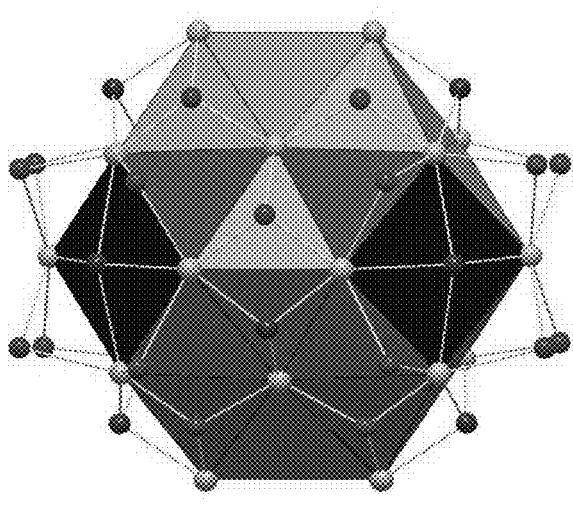
FIG. 41B          FIG. 41C

COMPOSITIONS AND METHODS RELATING TO MOLECULAR CERIUM-OXIDE NANOCLUSTERS

CROSS-REFERENCE TO RELATED APPLICATION

This application claims priority to U.S. non-provisional application entitled "COMPOSITIONS AND METHODS RELATING TO MOLECULAR CERIUM-OXIDE NANOCLUSTERS", having Ser. No. 16/467,088, filed on Jun. 6, 2019, which claims priority to application is the 35 U.S.C. § 371 national stage application of PCT Application No. PCT/US2017/064890 entitled "COMPOSITIONS AND METHODS RELATING TO MOLECULAR CERIUM-OXIDE NANOCLUSTERS" and filed Dec. 6, 2017, where the PCT claims priority to U.S. provisional patent application entitled "COMPOSITIONS AND METHODS RELATING TO MOLECULAR CERIUM-OXIDE NANOCLUSTERS", having Ser. No. 62/430,484, filed on Dec. 6, 2016, and U.S. provisional patent application entitled "COMPOSITIONS AND METHODS RELATING TO MOLECULAR CERIUM-OXIDE NANOCLUSTERS", having Ser. No. 62/579,217, filed on Oct. 31, 2017, all of which are entirely incorporated herein by reference.

BACKGROUND

Cerium oxide (ceria, $CeO_2$) is of importance to many different areas, including industrial catalysis of organic and inorganic reactions, advanced materials, environmental remediation (of power station wastewater, stream and rivers, etc), automobile exhaust scrubbing (deNOx, deSOx), polishing materials, and others. These diverse fields stem primarily from the $Ce^{3+}/Ce^{4+}$ redox couple capability and the relatively low cost of Ce. Unfortunately, many of these applications have to be carried out at high temperatures for significant activity, e.g. the catalysis applications.

In the last decade, study of ceria nanoparticles has seen explosive growth owing to the much greater activity they exhibit, and at lower temperatures, in comparison to the bulk material. This has also opened up various applications of ceria nanoparticles in biomedicine, spanning protection from reactive radicals to therapies for a variety of disorders. As the size of these nanoparticles decreases, the reactivity has been found to increase, but synthesizing a homogenous composition of small ceria nanoparticles without a significant size distribution and/or variation is nearly impossible and hampers detailed study of activity vs size. It has also been found that the $Ce^{3+}/Ce^{4+}$ ratio is very important to the reactivity, but determining the exact $Ce^{3+}/Ce^{4+}$ composition in nanoparticles is challenging. Accordingly, there is a need to address the aforementioned deficiencies and inadequacies.

SUMMARY

Described herein are methods of synthesizing a molecular cerium-oxide nanocluster composition. In certain aspects, methods as described herein comprise providing a cerium source, an organic acid, and a solvent; mixing the cerium source and the organic acid in a ratio of about 1:2 to about 1:4. Mixing can occur in the presence of a solvent to create a reaction mixture at a temperature and a pressure for a period of time to create a composition of molecular cerium-oxide nanoclusters. In certain aspects, a composition of molecular cerium-oxide nanoclusters can contain a plurality of molecular cerium-oxide nanoclusters (1 or more). In certain aspects, the molecular cerium-oxide nanoclusters can have a longest dimension with a size, a $Ce^{3+}/Ce^{4+}$ ratio, and a nuclearity of cerium. Methods of synthesizing molecular cerium-oxide nanocluster compositions can further comprise isolating the compositions with an isolation method.

Described herein are also compositions. In certain aspects, compositions as described herein can comprise a molecular cerium-oxide nanocluster of the formula $[Ce_xO_y(OH)_w(H_2O)_t(RCO_2)_z(L)_m]^n$, $[Ce_xO_y(OH)_w(H_2O)_t(RPO_2)_z(L)_m]^n$ or $[Ce_xO_y(OH)_w(H_2O)_t(RPO_3)_z(L)_m]^n$ of cerium nuclearity of 19 to 100, wherein l, m, n, w, x, y, z are integers of 0 or greater.

In certain aspects, R can be selected from the group consisting of: one or more Ph, one or more $CH_3$, one or more $CH_3CH_2$, one or more aromatic groups, one or more substituted phenyls, a plurality of connected phenyls, one or more linear or branched aliphatic groups, one or more substituted linear or branched aliphatic groups, one or more linear or branched alicyclic groups, or combinations thereof. In certain aspects, L can be one or more neutral organic molecules.

Also described herein are methods of scavenging reactive oxygen species. In certain aspects, methods as described herein can comprise one or more molecular cerium-oxide nanoclusters as described herein and reducing the level of one or more reactive oxygen species from a first level to a second level, wherein the first level is higher than the second level.

Also described herein are methods of treating oxidative stress in a subject in need thereof. Methods of treating oxidative stress in a subject in need thereof can comprise delivering, to a subject in need thereof, a pharmaceutical composition, wherein the pharmaceutical composition includes a therapeutically effective amount of a compound, or a pharmaceutically acceptable salt of the compound, and a pharmaceutically acceptable carrier, to treat the oxidative stress. The compound can comprise one or more molecular cerium-oxide nanoclusters are of the formula $[Ce_xO_y(OH)_w(H_2O)_t(RCO_2)_z(L)_m]^n$, $[Ce_xO_y(OH)_w(H_2O)_t(RPO_2)_z(L)_m]^n$ or $[Ce_xO_y(OH)_w(H_2O)_t(RPO_3)_z(L)_m]^n$ of cerium nuclearity of 19 to 100, wherein l, m, n, w, x, y, z are integers of 0 or greater.

Described herein are pharmaceutical compositions. Pharmaceutical compositions as described herein can comprise a therapeutically effective amount of a compound, or a pharmaceutically acceptable salt of the compound, and a pharmaceutically acceptable carrier, to treat oxidative stress. The compound can be of the following formula: $[Ce_xO_y(OH)_w(H_2O)_t(RCO_2)_z(L)_m]^n$, $[Ce_xO_y(OH)_w(H_2O)_t(RPO_2)_z(L)_m]^n$ or $[Ce_xO_y(OH)_w(H_2O)_t(RPO_3)_z(L)_m]^n$ of cerium nuclearity of 19 to 100, wherein l, m, n, w, x, y, z are integers of 0 or greater.

Further described herein are methods of scavenging free radicals. Scavenging free radicals can be reducing one or more of an amount, concentration, or half-life of free radical species in an environment (such as a fluid or in a living cell), and/or accelerating the rate of decay of free radical species in an environment (such as a fluid or in a living cell), wherein the rate of decay is the reduction in one or more of amount, concentration, or half-life over time. Methods of scavenging free radicals as described herein can comprise delivering a composition to an environment containing free radicals, wherein the composition comprises one or more molecular cerium-oxide nanoclusters with the following formula: $[Ce_xO_y(OH)_w(H_2O)_t(RCO_2)_z(L)_m]^n$, $[Ce_xO_y(OH)_w$ $(H_2O)_t(RPO_2)_z(L)_m]^n$ or $[Ce_xO_y(OH)_w(H_2O)_t(RPO_3)_z(L)_m]^n$ of cerium nuclearity of 19 to 100, wherein l, m, n, w, x, y, z are integers of 0 or greater.

BRIEF DESCRIPTION OF THE DRAWINGS

Many aspects of the disclosed devices and methods can be better understood with reference to the following drawings. The components in the drawings are not necessarily to scale, emphasis instead being placed upon clearly illustrating the relevant principles. Moreover, in the drawings, like reference numerals designate corresponding parts throughout the several views.

FIG. 3A illustrates a prior synthesis reaction for synthesizing a molecular cerium-oxide nanocluster of cerium nuclearity 16 ($Ce_{16}$).

FIG. 3B depicts a structure for a molecular cerium-oxide nanocluster of cerium nuclearity 16 ($Ce_{16}$).

FIG. 3C shows a structure for a molecular cerium-oxide nanocluster core ($[Ce_{16}O_{17}(OH)_6]^{24+}$) of cerium nuclearity 16 ($Ce_{16}$), demonstrating a flourite structure.

FIG. 5B shows a portion of bulk $CeO_2$ structure and the fluorite structure within.

FIG. 5C illustrates a $Ce_6$ nanocluster core structure, demonstrating the fluorite structure and structural similarity to bulk $CeO_2$.

FIG. 5D depicts a $Ce_{16}$ nanocluster core structure, demonstrating the fluorite structure and structural similarity to bulk $CeO_2$.

FIG. 5E shows a $Ce_{24}$ nanocluster core structure, demonstrating the fluorite structure and structural similarity to bulk $CeO_2$.

FIG. 13A illustrates a synthesis reaction for synthesizing a molecular cerium-oxide nanocluster of cerium nuclearity 24 ($Ce_{24}$).

FIG. 13B depicts a structure for a molecular cerium-oxide nanocluster of cerium nuclearity 24 ($Ce_{24}$).

FIG. 13C shows a structure for a molecular cerium-oxide nanocluster core of cerium nuclearity 24 ($Ce_{24}$), demonstrating the flourite structure.

FIGS. 15A-15B shows bond valence sums (BVS) calculations for an embodiment of a molecular cerium-oxide nanocluster of cerium nuclearity 24 ($Ce_{24}$).

FIG. 17A depicts coordination numbers and BVS calculations for embodiment of a molecular cerium-oxide nanocluster of cerium nuclearity 38 ($Ce_{38}$).

FIG. 17B depicts coordination numbers and BVS calculations for embodiment of a molecular cerium-oxide nanocluster of cerium nuclearity 38 ($Ce_{38}$).

FIG. 18A shows BVS calculations for an embodiment of a molecular cerium-oxide nanocluster of cerium nuclearity 38 ($Ce_{38}$).

FIG. 18B shows BVS calculations for an embodiment of a molecular cerium-oxide nanocluster of cerium nuclearity 38 ($Ce_{38}$).

FIG. 19A illustrates a synthesis reaction for synthesizing a molecular cerium-oxide nanocluster of cerium nuclearity 38 ($Ce_{38}$).

FIG. 19B depicts a structure for a molecular cerium-oxide nanocluster of cerium nuclearity 38 ($Ce_{38}$).

FIG. 19C shows a structure for a molecular cerium-oxide nanocluster core of cerium nuclearity 38 ($Ce_{38}$), demonstrating the flourite structure.

FIG. 20A illustrates a synthesis reaction for synthesizing a molecular cerium-oxide nanocluster of cerium nuclearity 38 ($Ce_{38}$).

FIG. 20B depicts a structure for a molecular cerium-oxide nanocluster of cerium nuclearity 38 ($Ce_{38}$).

FIG. 20C shows a structure for a molecular cerium-oxide nanocluster core of cerium nuclearity 38 ($Ce_{38}$), demonstrating the flourite structure.

FIG. 22A shows coordination numbers and oxidation states for an embodiment of $Ce_{38}$.

FIG. 22B shows coordination numbers and oxidation states for an embodiment of $Ce_{38}$.

FIG. 23A depicts coordination numbers and BVS calculations for an embodiment of $Ce_{40}$.

FIG. 23B depicts coordination numbers and BVS calculations for an embodiment of $Ce_{40}$.

FIG. 24A shows bond valence sums of $Ce^{3+}$ and $Ce^{4+}$ for a cerium-oxide nanocluster of nuclearity 40 ($Ce_{40}$).

FIG. 24B shows bond valence sums of $Ce^{3+}$ and $Ce^{4+}$ for a cerium-oxide nanocluster of nuclearity 40 ($Ce_{40}$).

FIG. 29A shows coordination numbers and oxidation states for an embodiment of a $Ce_{40}$ molecular cerium-oxide nanocluster.

FIG. 29B shows coordination numbers and oxidation states for an embodiment of a $Ce_{40}$ molecular cerium-oxide nanocluster.

FIGS. 38A-38C show the full structure of complex 1 (FIG. 38A), core of complex 1 (FIG. 38B) and core in facet view (FIG. 39C). Color code: $Ce^{IV}$ gold, O red, protonated O (i.e. $OH^-$) purple, C grey. H atoms have been omitted for clarity, except for water protons (black). Green surfaces represent the (111) facet.

FIGS. 40A-40C show the full structure of complex 3 (FIG. 40A), core of complex 3 (FIG. 40B) and core in facet view (FIG. 40C). Color code: $Ce^{IV}$ gold, $Ce^{III}$ light blue, O red, protonated O (i.e. $OH^-$) purple, C grey. H atoms have been omitted for clarity. Green surfaces represent the (111) facet and blue surfaces represent the (100) facet.

FIGS. 41A-41C show the full structure of complex 5 (FIG. 41A), core of complex 5 (FIG. 41B) and core in facet view (FIG. 41C). Color code: $Ce^{IV}$ gold, $Ce^{III}$ light blue, O red, protonated O (i.e. $OH^-$) purple, C grey. H atoms have been omitted for clarity. Green surfaces represent the (111) facet and blue surfaces represent the (100) facet.

FIG. 44A is an EPR spectra of the DMPO spin-trap adduct generated from the reaction between $H_2O_2$ (10 mM), $FeCl_2$ (10 mM), and DMPO (0.5 M) in the absence (control) and presence of 1 mM 1 ($Ce_6$). FIG. 44B represents the same conditions as for FIG. 44A but using 1 mM 5 ($Ce_{40}$). FIG. 44C shows plots of signal intensity of the second peak (at ~3506 G) of the DMPO spin-trap adduct vs. time in the absence (control) and presence of 1-7.

DETAILED DESCRIPTION

Figure 1A:
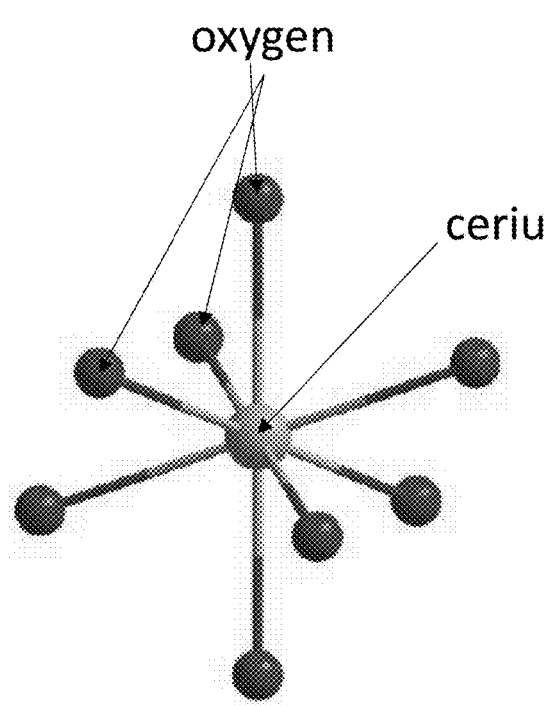
FIGS. 1A-1D depicts illustrations of various aspects of the "fluorite structure" with atoms of cerium (Ce) and oxygen (O).

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of organic and inorganic chemistry which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in atmosphere. Standard temperature and pressure are defined as 25° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Definitions

Unless otherwise defined, all technical and scientific terms used herein have the same meaning as commonly understood by one of ordinary skill in the art of molecular biology, medicinal chemistry, and/or organic chemistry.

Although methods and materials similar or equivalent to those described herein can be used in the practice or testing of the present disclosure, suitable methods and materials are described herein.

As used in the specification and the appended claims, the singular forms "a," "an," and "the" may include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

The term "substituted" refers to any one or more hydrogen atoms on the designated atom (e.g., a carbon atom) that can be replaced with a selection from the indicated group (e.g., halide, hydroxyl, alkyl, and the like), provided that the designated atom's normal valence is not exceeded.

As used herein, an "analog", or "analogue" of a chemical compound is a compound that, by way of example, resembles another in structure but is not necessarily an isomer (e.g., 5-fluorouracil is an analog of thymine).

As used herein, a "derivative" of a compound refers to a chemical compound that may be produced from another compound of similar structure in one or more steps, as in replacement of H by an alkyl, acyl, or amino group.

As used herein, "aliphatic" or "aliphatic group" refers to a saturated or unsaturated, linear or branched, cyclic (non-aromatic) or heterocyclic (non-aromatic), hydrocarbon or hydrocarbon group and encompasses alkyl, alkenyl, and alkynyl groups, and alkanes, alkene, alicyclic groups, and alkynes, for example.

As used herein, "alkane" refers to a saturated aliphatic hydrocarbon which can be straight or branched, having 1 to 40, 1 to 20, 1 to 10, or 1 to 5 carbon atoms, where the stated range of carbon atoms includes each intervening integer individually, as well as sub-ranges. Examples of alkane include, but are not limited to methane, ethane, propane, butane, pentane, and the like. Reference to "alkane" includes unsubstituted and substituted forms of the hydrocarbon.

As used herein, "alkyl" or "alkyl group" refers to a saturated aliphatic hydrocarbon radical which can be straight or branched, having 1 to 40, 1 to 20, 1 to 10, or 1 to 5 carbon atoms, where the stated range of carbon atoms includes each intervening integer individually, as well as sub-ranges. Examples of alkanes include, but are not limited to methyl, ethyl, n-propyl, i-propyl, n-butyl, s-butyl, t-butyl, n-pentyl, and s-pentyl. Reference to "alkyl" or "alkyl group" includes unsubstituted and substituted forms of the hydrocarbon group.

As used herein, "alkene" refers to an aliphatic hydrocarbon which can be straight or branched, containing at least one carbon-carbon double bond, having 2 to 40, 2 to 20, 2 to 10, or 2 to 5 carbon atoms, where the stated range of carbon atoms includes each intervening integer individually, as well as sub-ranges. Examples of alkene groups include, but are not limited to, ethene, propene, and the like. Reference to "alkene" includes unsubstituted and substituted forms of the hydrocarbon.

As used herein, "alkenyl" or "alkenyl group" refers to an aliphatic hydrocarbon radical which can be straight or branched, containing at least one carbon-carbon double bond, having 2 to 40, 2 to 20, 2 to 10, or 2 to 5 carbon atoms, where the stated range of carbon atoms includes each intervening integer individually, as well as sub-ranges. Examples of alkenyl groups include, but are not limited to, ethenyl, propenyl, n-butenyl, i-butenyl, 3-methylbut-2-enyl, n-pentenyl, heptenyl, octenyl, decenyl, and the like. Reference to "alkyl" or "alkyl group" includes unsubstituted and substituted forms of the hydrocarbon group.

As used herein, "alkyne" refers to straight or branched chain hydrocarbon groups having 2 to 40, 2 to 20, 2 to 10, or 2 to 5 carbon atoms and at least one triple carbon to carbon bond. Reference to "alkyne" includes unsubstituted and substituted forms of the hydrocarbon.

As used herein, "alkynyl" or "alkynyl group" refers to straight or branched chain hydrocarbon groups having 2 to 40, 2 to 20, 2 to 10, or 2 to 5 carbon atoms and at least one triple carbon to carbon bond, such as ethynyl. Reference to "alkynyl" or "alkynyl group" includes unsubstituted and substituted forms of the hydrocarbon group.

As used herein, "aromatic" or "aromatic group" refers to a monocyclic or multicyclic ring system of 6 to 20 or 6 to 10 carbon atoms having alternating double and single bonds between carbon atoms. Exemplary aromatic groups include benzene, naphthalene, and the like. Reference to "aromatic" includes unsubstituted and substituted forms of the hydrocarbon.

As used herein, "aryl" or "aryl group" refers to an aromatic monocyclic or multicyclic ring system of 6 to 20 or 6 to 10 carbon atoms. The aryl is optionally substituted with one or more $C_1$-$C_{20}$ alkyl, alkylene, alkoxy, or haloalkyl groups. Exemplary aryl groups include phenyl or naphthyl, or substituted phenyl or substituted naphthyl. Reference to "aryl" or "aryl group" includes unsubstituted and substituted forms of the hydrocarbon group.

The term "arylalkyl" refers to an arylalkyl group wherein the aryl and alkyl are as herein described. Examples of arylalkyl include, but are not limited to, -phenylmethyl, phenylethyl, -phenylpropyl, -phenylbutyl, and -phenylpentyl.

The term "substituted," as in "substituted alkyl", "substituted aryl," "substituted heteroaryl" and the like, means that the substituted group may contain in place of one or more hydrogens a group such as alkyl, hydroxy, amino, halo, trifluoromethyl, cyano, alkoxy, alkylthio, or carboxy. A carboxy group or carboxylate can have the formula $RCO_2$— where R=various.

As used herein, "halo", "halogen", "halide", or "halogen radical" refers to a fluorine, chlorine, bromine, iodine, and astatine, and radicals thereof. Further, when used in compound words, such as "haloalkyl" or "haloalkenyl", "halo" refers to an alkyl or alkenyl radical in which one or more hydrogens are substituted by halogen radicals. Examples of haloalkyl include, but are not limited to, trifluoromethyl, trichloromethyl, pentafluoroethyl, and pentachloroethyl.

As used herein, "cyclic" hydrocarbon refers to any stable 4, 5, 6, 7, 8, 9, 10, 11, or 12 membered, (unless the number of members is otherwise recited), monocyclic, bicyclic, or tricyclic cyclic ring.

As used herein, "heterocycle" refers to any stable 4, 5, 6, 7, 8, 9, 10, 11, or 12 membered, (unless the number of members is otherwise recited), monocyclic, bicyclic, or tricyclic heterocyclic ring that is saturated or partially unsaturated, and which includes carbon atoms and 1, 2, 3, or 4 heteroatoms independently selected from the group consisting of N, O, and S. If the heterocycle is defined by the number of carbons atoms, then from 1, 2, 3, or 4 of the listed carbon atoms are replaced by a heteroatom. If the heterocycle is bicyclic or tricyclic, then at least one of the two or three rings must contain a heteroatom, though both or all three may each contain one or more heteroatoms. The N group may be N, NH, or N-substituent, depending on the chosen ring and if substituents are recited. The nitrogen and sulfur heteroatoms optionally may be oxidized (e.g., S, S(O), S(O)$_2$, and N—O). The heterocycle may be attached to its pendant group at any heteroatom or carbon atom that results in a stable structure. The heterocycles described herein may be substituted on carbon or on a heteroatom if the resulting compound is stable.

"Heteroaryl" refers to any stable 5, 6, 7, 8, 9, 10, 11, or 12 membered, (unless the number of members is otherwise recited), monocyclic, bicyclic, or tricyclic heterocyclic ring that is aromatic, and which consists of carbon atoms and 1, 2, 3, or 4 heteroatoms independently selected from the group consisting of N, O, and S. If the heteroaryl is defined by the number of carbons atoms, then 1, 2, 3, or 4 of the listed carbon atoms are replaced by a heteroatom. If the heteroaryl group is bicyclic or tricyclic, then at least one of the two or three rings must contain a heteroatom, though both or all three may each contain one or more heteroatoms. If the heteroaryl group is bicyclic or tricyclic, then only one of the rings must be aromatic. The N group may be N, NH, or N-substituent, depending on the chosen ring and if substituents are recited. The nitrogen and sulfur heteroatoms may optionally be oxidized (e.g., S, S(O), S(O)$_2$, and N—O). The heteroaryl ring may be attached to its pendant group at any heteroatom or carbon atom that results in a stable structure. The heteroaryl rings described herein may be substituted on carbon or on a nitrogen atom if the resulting compound is stable.

The term "heteroatom" means for example oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring).

The term "bicyclic" represents either an unsaturated or saturated stable 7- to 12-membered bridged or fused bicyclic carbon ring. The bicyclic ring may be attached at any carbon atom which affords a stable structure. The term includes, but is not limited to, naphthyl, dicyclohexyl, dicyclohexenyl, and the like.

As used herein, the term "purified" and like terms (such as "isolated") relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

As used herein, the term "nuclearity" relates to the number of central metal atoms in a coordination compound (or nanocluster as used herein).

As used herein, the term "cerium source" denotes any composition containing cerium in the +3 and/or +4 oxidation state, and can be a salt with a counter ion such as nitrade, halide, or similar.

As used herein, "crystallization agent" can refer to any composition which can aid in the formation of crystals of a given composition.

As used herein, a "nitrate group" is a chemical group containing NO$_3$.

As used herein, a "neutral organic molecule" can be a molecule or moiety having zero net electrical charge, optionally having both cationic and anionic groups.

The term "alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. The term "lower alkoxy" means an alkoxy group having less than 10 carbon atoms.

The term "carbocycles" refers to a monocyclic or multicyclic ring system of about 3 to about 14 carbon atoms, preferably of about 6 to about 10 carbon atoms. In an embodiment, carbocycle can refer to an aryl group. Exemplary carbocycles can refer to functional groups.

The term "cycloalkyl" refers to a non-aromatic mono- or multicyclic ring system of about 3 to about 10 carbon atoms, preferably of about 5 to about 10 carbon atoms. Preferred ring sizes of rings of the ring system include about 5 to about 6 ring atoms. Exemplary monocyclic cycloalkyl include cyclopentyl, cyclohexyl, cycloheptyl, and the like. Exemplary multicyclic cycloalkyl include 1-decalin, norbornyl, adamant-(1- or 2-)yl, and the like. Reference to a cycloalkyl group includes substituted and unsubstituted cycloalkyl groups.

The term "cycloalkenyl" refers to a non-aromatic mono- or multicyclic ring system of about 3 to about 10 carbon atoms, preferably of about 5 to about 10 carbon atoms, and which contains at least one carbon-carbon double bond. Preferred ring sizes of rings of the ring system include about 5 to about 6 ring atoms. Exemplary monocyclic cycloalkenyl include cyclopentenyl, cyclohexenyl, cycloheptenyl, and the like. An exemplary multicyclic cycloalkenyl is norbornylenyl. Reference to a cycloalkyl group includes substituted and unsubstituted cycloalkyl groups. Reference to a cycloalkenyl group includes substituted and unsubstituted cycloalkenyl groups.

"Aralkyl" and "heteroaralkyl" refer to aryl and heteroaryl moieties, respectively, that are linked to a main structure by an intervening alkyl group, e.g., containing one or more methylene groups.

The term "fluorobenzyl" refers to a benzyl group wherein the phenyl moiety is substituted with one or more fluorine atoms, including 2, 3, 4 and 5 fluorine atom substituents.

Similarly, "halobenzyl" refers to benzyl substituted with one or more different halogens, including fluorine, chlorine, bromine, and iodine (not astatine).

The terms "sulfide" and "thioether" as used herein, alone or in combination, refer to a sulfur atom covalently linked to two atoms; the formal oxidation state of said sulfur is (II). These terms may be used interchangeably.

The term "sulfanyl" as used herein, alone or in combination, refers to the —S—R group, wherein R may be a group such as: alkyl, alkenyl, alkynyl, aryl, alicyclic, heterocyclic, aryl, heteroaryl, arylalkyl and heteroarylalkyl, wherein the alkyl, alkenyl, alkynyl, aryl, alicyclic, heterocyclic, aryl, heteroaryl, arylalkyl and heteroarylalkyl groups may be optionally substituted. Non-limiting examples of sulfanyl groups include methylsulfanyl (—SCH$_3$) and iso-propylsulfanyl (—SCH(CH$_3$)$_2$) and the like.

The term "unit dosage form," as used herein, refers to physically discrete units suitable as unitary dosages for human and/or animal subjects, each unit containing a predetermined quantity of a compound (e.g., compositions or pharmaceutical compositions, as described herein) calculated in an amount sufficient to produce the desired effect in association with a pharmaceutically acceptable diluent, carrier or vehicle. The specifications for unit dosage forms depend on the particular compound employed, the route and frequency of administration, and the effect to be achieved, and the pharmacodynamics associated with each compound in the subject.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use. "A pharmaceutically acceptable excipient, diluent, carrier and/or adjuvant" as used in the specification and claims includes one and more such excipients, diluents, carriers, and adjuvants.

As used herein, a "pharmaceutical composition" is meant to encompass a composition or pharmaceutical composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, intravenous, buccal, rectal, parenteral, intraperitoneal, intradermal, intracheal, intramuscular, subcutaneous, inhalational and the like.

The term "therapeutically effective amount" as used herein refers to that amount of an embodiment of the composition or pharmaceutical composition being administered that will relieve to some extent one or more of the symptoms of the disease, i.e., infection, being treated, and/or that amount that will prevent, to some extent, one or more of the symptoms of the disease, i.e., infection, that the subject being treated has or is at risk of developing.

"Pharmaceutically acceptable salt" refers to those salts that retain the biological effectiveness and optionally other properties of the free bases and that are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like.

In the event that embodiments of the disclosed compounds in the composition or pharmaceutical composition form salts, these salts are within the scope of the present disclosure. Reference to a compound used in the composition or pharmaceutical composition of any of the formulas herein is understood to include reference to salts thereof, unless otherwise indicated. The term "salt(s)", as employed herein, denotes acidic and/or basic salts formed with inorganic and/or organic acids and bases. In addition, when a compound contains both a basic moiety and an acidic moiety, zwitterions ("inner salts") may be formed and are included within the term "salt(s)" as used herein. Pharmaceutically acceptable (e.g., non-toxic, physiologically acceptable) salts are preferred, although other salts are also useful, e.g., in isolation or purification steps which may be employed during preparation. Salts of the compounds of a compound may be formed, for example, by reacting the compound with an amount of acid or base, such as an equivalent amount, in a medium such as one in which the salt precipitates or in an aqueous medium followed by lyophilization.

Embodiments of the compounds of the composition or pharmaceutical composition of the present disclosure that contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Embodiments of the compounds of the composition or pharmaceutical composition of the present disclosure that contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine, and the like.

Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Solvates of the compounds of the composition or pharmaceutical composition of the present disclosure are also contemplated herein.

To the extent that the disclosed the compounds of the composition or pharmaceutical composition of the present disclosure, and salts thereof, may exist in their tautomeric form, all such tautomeric forms are contemplated herein as part of the present disclosure.

All stereoisomers of the compounds of the composition or pharmaceutical composition of the present disclosure, such as those that may exist due to asymmetric carbons on the various substituents, including enantiomeric forms (which may exist even in the absence of asymmetric carbons) and diastereomeric forms are contemplated within the scope of this disclosure. Individual stereoisomers of the compounds of the disclosure may, for example, be substantially free of other isomers, or may be admixed, for example, as racemates or with all other, or other selected, stereoisomers. The stereogenic centers of the compounds of the present disclosure can have the S or R configuration as defined by the IUPAC 1974 Recommendations.

The term "prodrug" refers to an inactive precursor of the compounds of the composition or pharmaceutical composition of the present disclosure that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Harper, N.J. (1962). Drug Latentiation in Jucker, ed. Progress in Drug Research, 4:221-294; Morozowich et al. (1977). Application of Physical Organic Principles to Prodrug Design in E. B. Roche ed. Design of Biopharmaceutical Properties through Prodrugs and Analogs, APhA; Acad. Pharm. Sci.; E. B. Roche, ed. (1977). Bioreversible Carriers in Drug in Drug Design, Theory and Application, APhA; H. Bundgaard, ed. (1985) Design of Prodrugs, Elsevier; Wang et al. (1999) Prodrug approaches to the improved delivery of peptide drug, Curr. Pharm. Design. 5(4):265-287; Pauletti et al. (1997). Improvement in peptide bioavailability: Peptidomimetics and Prodrug Strategies, Adv. Drug. Delivery Rev. 27:235-256; Mizen et al. (1998). The Use of Esters as Prodrugs for Oral Delivery of β-Lactam antibiotics, Pharm. Biotech. 11,:345-365; Gaignault et al. (1996). Designing Prodrugs and Bioprecursors I. Carrier Prodrugs, Pract. Med. Chem. 671-696; M. Asgharnejad (2000). Improving Oral Drug Transport Via Prodrugs, in G. L. Amidon, P. I. Lee and E. M. Topp, Eds., Transport Processes in Pharmaceutical Systems, Marcell Dekker, p. 185-218; Balant et al. (1990) Prodrugs for the improvement of drug absorption via different routes of administration, Eur. J. Drug Metab. Pharmacokinet., 15(2): 143-53; Balimane and Sinko (1999). Involvement of multiple transporters in the oral absorption of nucleoside analogues, Adv. Drug Delivery Rev., 39(1-3): 183-209; Browne (1997). Fosphenytoin (Cerebyx), Clin. Neuropharmacol. 20(1): 1-12; Bundgaard (1979). Bioreversible derivatization of drugs—principle and applicability to improve the therapeutic effects of drugs, Arch. Pharm. Chemi. 86(1): 1-39; H. Bundgaard, ed. (1985) Design of Prodrugs, New York: Elsevier; Fleisher et al. (1996). Improved oral drug delivery: solubility limitations overcome by the use of prodrugs, Adv. Drug Delivery Rev. 19(2): 115-130; Fleisher et al. (1985). Design of prodrugs for improved gastrointestinal absorption by intestinal enzyme targeting, Methods Enzymol. 112: 360-81; Farquhar D, et al. (1983). Biologically Reversible Phosphate-Protective Groups, J. Pharm. Sci., 72(3): 324-325; Han, H. K. et al. (2000). Targeted prodrug design to optimize drug delivery, AAPS PharmSci., 2(1): E6; Sadzuka Y. (2000). Effective prodrug liposome and conversion to active metabolite, Curr. Drug Metab., 1(1): 31-48; D. M. Lambert (2000) Rationale and applications of lipids as prodrug carriers, Eur. J. Pharm. Sci., 11 Suppl 2: S15-27; Wang, W. et al. (1999) Prodrug approaches to the improved delivery of peptide drugs. Curr. Pharm. Des., 5(4): 265-87.

The term "administration" refers to introducing a composition of the present disclosure into a subject. One preferred route of administration of the composition is oral administration. Another preferred route is intravenous administration. However, any route of administration, such as topical, subcutaneous, peritoneal, intraarterial, inhalation, vaginal, rectal, nasal, introduction into the cerebrospinal fluid, or instillation into body compartments can be used.

As used herein, "treat", "treatment", "treating", and the like refer to acting upon a condition (e.g., an infection), a disease or a disorder with a composition to affect the condition, disease or disorder by improving or altering it. The improvement or alteration may include an improvement in symptoms or an alteration in the physiologic pathways associated with the condition, disease, or disorder. "Treatment," as used herein, covers one or more treatments of an infection, a condition or a disease in a subject (e.g., a mammal, typically a human or non-human animal of veterinary interest), and includes: (a) reducing the risk of occurrence of the infection, condition, or a disease in a subject determined to be predisposed to the condition or disease but not yet diagnosed with it (b) impeding the development of the infection, and/or (c) relieving the infection, e.g., causing regression of the infection and/or relieving one or more infection symptoms.

As used herein, the terms "prophylactically treat" or "prophylactically treating" refers completely or partially preventing (e.g., about 50% or more, about 60% or more, about 70% or more, about 80% or more, about 90% or more, about 95% or more, or about 99% or more) a condition (e.g., infection), a disease, or a symptom thereof and/or may be therapeutic in terms of a partial or complete cure for an infection, and/or adverse effect attributable to the infection.

As used herein, the term "subject," or "patient," includes humans, mammals (e.g., mice, rats, pigs, cats, dogs, and horses), and birds. Typical subjects to which compounds of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. The term "living subject" refers to a subject noted above or another organism that is alive. The term "living subject" refers to the entire subject or organism and not just a part excised (e.g., a liver or other organ) from the living subject.

DISCUSSION

Embodiments of the present disclosure provide for compositions and methods relating to molecular nanoclusters. Discussed herein are embodiments of compositions of molecular nanoclusters in addition to embodiments of methods for the synthesis of such compounds.

Figure 1B:
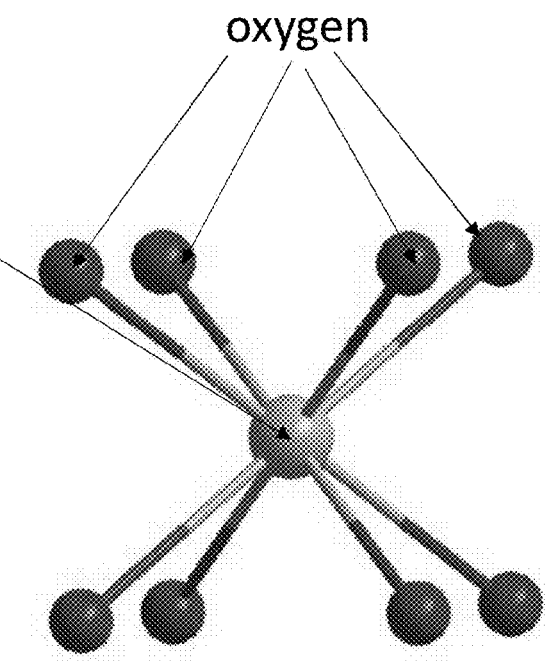
Figure 1C:
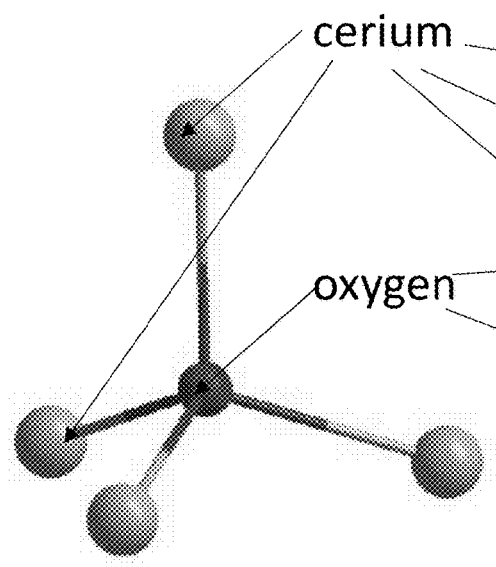
Figure 1D:
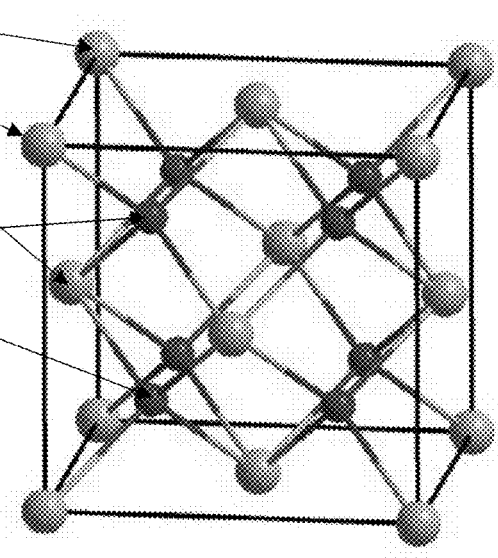

Cerium is the most abundant of the rare earth elements (more abundant than Pb and Sn). It is stable in both $Ce^{3+}$ and $Ce^{4+}$ oxidation states, and is most commonly employed in its bulk form: $CeO_2$. $CeO_2$ displays the solid-state structure known as the Fluorite structure, wherein each Ce ion is coordinated to 8 O atoms (FIGS. 1A-1B) in a perfect cube (FIG. 1D) and each O is coordinated to 4 Ce atoms in a tetrahedral arrangement (FIG. 1C). Cerium oxide (ceria, $CeO_2$) is of importance to many different areas, including industrial catalysis of organic and inorganic reactions, advanced materials, environmental remediation (e.g., of power station wastewater, stream and rivers, etc.), automobile exhaust scrubbing (deNOx, deSOx), polishing materials, and others. These diverse fields stem primarily from the $Ce^{3+}/Ce^{4+}$ redox couple capability (ability to easily switch between the trivalent 3+ and tetravalent$^{4+}$ oxidation states) and the relatively low cost of Ce. Unfortunately, many of these applications have to be carried out at high temperatures for significant activity, e.g., the catalysis applications.

In the last decade, study of ceria nanoparticles has seen explosive growth owing to the much greater activity they exhibit, and at lower temperatures, in comparison to the bulk material. This has also opened up various applications of ceria nanoparticles in biomedicine, including protection from reactive radicals to therapies for a variety of disorders. As the size of these nanoparticles decreases, the reactivity has been found to increase, but synthesizing a homogenous composition of small ceria nanoparticles without a significant size distribution and/or variation is nearly impossible and hampers detailed study of activity vs size. It has also been found that the $Ce^{3+}/Ce^{4+}$ ratio is a parameter related to the reactivity, but determining the exact $Ce^{3+}/Ce^{4+}$ composition in nanoparticles is challenging. Additionally, bulk $CeO_2$ is difficult to reduce and therefore has a low $Ce^{3+}$ concentration, whereas ceria nanoparticles have an increase in $Ce^{3+}$ concentration with decreasing particle size.

Molecular cerium-oxide clusters would provide an important alternative route to ultra-small ceria nanoparticles of finite dimensions. Such clusters could bring along all of the advantages of molecular chemistry, such as solubility, crystallinity, and monodispersity (single-size), allowing (i) the exact size, shape, surface ligation, surface protonation level, and $Ce^{3+}/Ce^{4+}$ ratio to be determined by X-ray crystallography and spectroscopic techniques; and (ii) the reactivity to be investigated as a function of size, $Ce^{3+}/Ce^{4+}$ ratio, etc., in a more controlled manner than the nanoparticles. This could be a major advantage in understanding of the mechanism by which nano-ceria can function as effective catalysts in biomedical, industrial, and environmental applications, and provide a means to optimize their activity and efficiency in applications. This novel molecular approach to cerium-oxide chemistry is an area with immense room for exploration.

Existing cerium-oxide products are all currently based on the nanoparticle form or bulk form of this material. Molecular cerium-oxide clusters represent a new molecular approach to obtaining ultra-small cerium-oxide nanoparticles, which are difficult to achieve using traditional nanoparticle synthesis methods. As mentioned above, the size of nanoparticles has been shown to have dramatic effects on the activity, with the smaller nanoparticles usually showing the highest activity. However, it is very difficult to establish these size-to-activity relationships with nanoparticles since they always possess some size distribution and it cannot be ensured that all nanoparticles are identical with respect to surface features. The concentration of $Ce^{3+}$ is also extremely difficult to determine with accuracy in nanoparticles.

Synthetic methods as described herein have been developed for the synthesis of molecular $Ce/O/RCO_2$-clusters of various nuclearities (e.g., $Ce_{19}$, $Ce_{24}$, $Ce_{38}$, and $Ce_{40}$) using simple carboxylates ($RCO_2$—; R=various). These clusters can have a Ce/O core surrounded by the carboxylates on the outside. Embodiments of the clusters are molecular versions of $CeO_2$ as they can have the same arrangement of Ce and O atoms as in bulk $CeO_2$ (the so-called fluorite structure, which can be described as alternating layers of Ce and oxides where Ce ions are linked by tetrahedral oxides), without the disadvantages of bulk $CeO_2$. Each Ce—O cluster can exhibit the fluorite structure of bulk $CeO_2$, and the core of Ce clusters can possess one or more $Ce^{3+}$ ions on the edge surfaces, similar to $CeO_2$ nanoparticles. These clusters can be capable of allowing study of their general properties and activity in various catalytic and biomedical systems as a function of the nuclearity, size, $Ce^{3+}/Ce^{4+}$ ratio, and other mentioned parameters as described herein. Embodiments of the molecular $Ce/O/RCO_2$-clusters behave like the nanoparticles, without their disadvantages, so the molecular $Ce/O/RCO_2$-clusters have broad applicability and can be utilized in many of the same applications. Additionally, the molecular $Ce/O/RCO_2$-clusters are stable with respect to reduction as indicated by large potentials required to observe any electrochemical activity.

Various molecules as described herein can be synthesized that allow the study of the reactivity as a function of exact size of the molecule. The exact $Ce^{3+}/Ce^{4+}$ ratio that each molecule possesses, which has been shown to affect the activity and is also extremely difficult to determine in nanoparticles, can be selected. These molecules may be more reactive than the nanoparticles due to their small size, therefore increasing the efficiency of the processes and applications which currently use cerium-oxide nanoparticles to perform various functions. Additionally, embodiments of the molecular $Ce/O/RCO_2$-clusters as described herein may help improve the efficiency of the nanoparticles by revealing the mechanisms by which they are able to carry out various reactions allowing for specific tuning of the synthetic procedures to attain desired properties.

Molecular cerium-nanoclusters and methods as described herein provide single-size nanocusters of which nanoclusters of a given species are identical to one an another. Nanoclusters as described herein are much more active than previously described ceria compositions because they do not suffer problems such as, from agglomeration (nanoparticles sticking together). These points can be important especially for medical applications, since they affect activity, toxicity, etc.

Embodiments of the molecular $Ce/O/RCO_2$-clusters are identical and monodisperse in a composition. In addition, the molecular $Ce/O/RCO_2$-clusters can be crystallized allowing for complete structural characterization, which is advantageous to determine how to use the molecular $Ce/O/RCO_2$-clusters. Embodiments of the molecular $Ce/O/RCO_2$-clusters are soluble in common solvents such as water or common organic solvents such as alcohols, ketones, MeCN and similar. Further, the molecular $Ce/O/RCO_2$-clusters can use different organic ligands, which allows the characteristics of the molecular $Ce/O/RCO_2$-clusters to be designed for particular applications.

Embodiments of the molecular $Ce/O/RCO_2$-clusters can have a smallest size region (i.e., smallest dimension, which can be a length, width, diameter, circumference, radius, etc.) of about 1-2 nm. In this range the molecular $Ce/O/RCO_2$-clusters have significant activity and reactivity, but when compared to nanoparticles of a similar size, the synthesis of single-size nanoparticles is the most difficult to control. In an embodiment, the size of the molecular $Ce/O/RCO_2$-clusters can be controlled, at least in part, by selection of the organic acid used in the synthesis. Smaller size not only imparts improved activity, but has other advantages over larger particles, such as lower toxicity and side effects in biological applications.

In an embodiment, the molecular $Ce/O/RCO_2$-clusters can be prepared to have a homogenous size, nuclearity, or other properties, individually or in combination, which cannot be easily, if at all, accomplished with nanoparticles.

Embodiments of the molecular $Ce/O/RCO_2$-clusters have components that are covalently bound (for example organic acid constituents). Also, in an embodiment, the molecular $Ce/O/RCO_2$-clusters do not aggregate together to form larger clusters as nanoparticles often do. In this regard, the molecular $Ce/O/RCO_2$-clusters are non-aggregated.

Embodiments of the molecular $Ce/O/RCO_2$-clusters can be used in place of ceria nanoparticles, but in contrast, the size, shape, surface ligation, $Ce^{3+}/Ce^{4+}$ ratio, surface protonation, and the like, of the molecular $Ce/O/RCO_2$-clusters of the present disclosure can be controlled and designed. In this regard, embodiments of the molecular $Ce/O/RCO_2$-clusters can be used in: industrial and petrochemical catalysis (e.g., the water-gas shift reaction, preferential oxidation of carbon monoxide, soot combustion, three-way catalytic converters in automobiles, cracking of heavy petroleum fractions, and others), solid-oxide fuel cells (e.g., as an electrolyte), UV absorbers; chemical mechanical polishing (e.g., used to produce a transparent surface for optical elements), biomedicine (e.g., as either pro- or anti-oxidants and demonstrate activity at low temperatures (potential for use in diseases where reactive oxygen species can cause cell damage and death, such as stroke and Alzheimers disease), photocatalysts for wastewater remediation treatments and water oxidation, cosmetics, and destruction of chemical warfare agents.

Figure 2A:
FIG. 2A illustrates a prior synthesis reaction for synthesizing a molecular cerium-oxide nanocluster of low cerium nuclearity (cerium nuclearity 6, $Ce_6$).
Figure 2A:
Figure 2A:
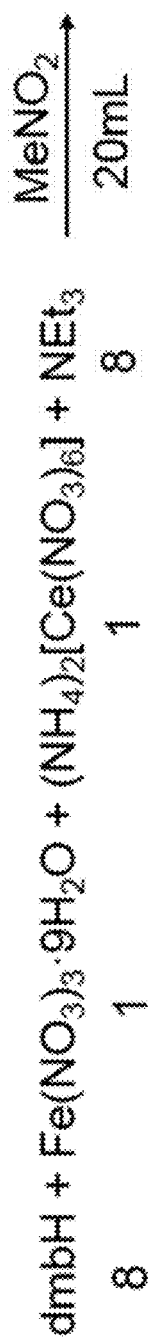
Figure 2C:
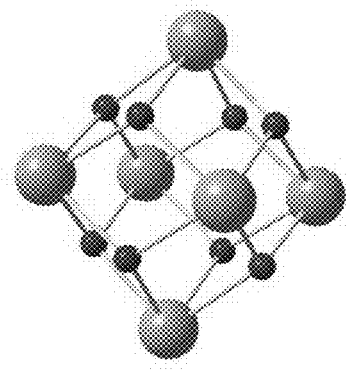
FIG. 2C shows a structure for a molecular cerium-oxide nanocluster core of low cerium nuclearity (cerium nuclearity 6, $Ce_6$), which has an $[Ce_6(O)_4(OH)_4]^{12+}$ octahedron, demonstrating a flourite structure.
Figure 2B:
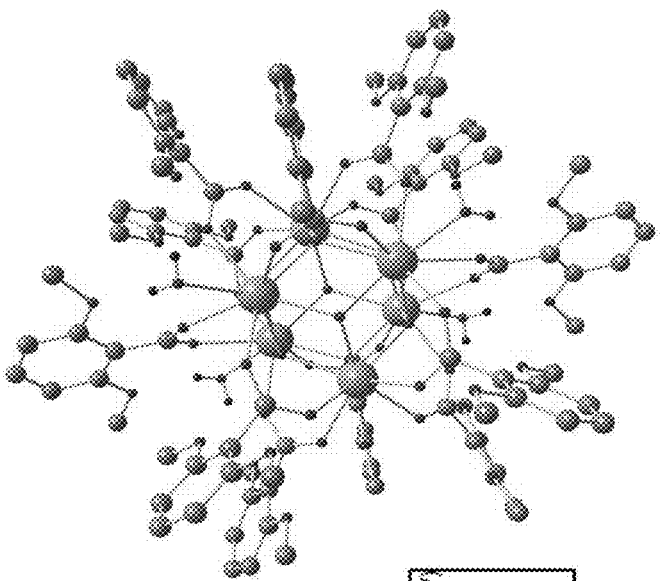
FIG. 2B depicts a structure for a molecular cerium-oxide nanocluster of low cerium nuclearity (cerium nuclearity 6, $Ce_6$).
Figure 2B:
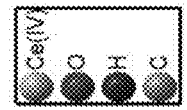
Figure 4C:
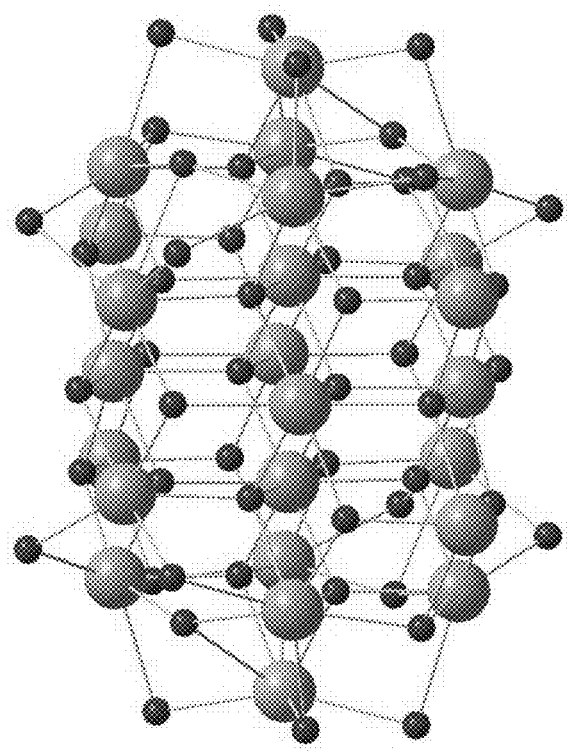
FIG. 4C shows a structure for a molecular cerium-oxide nanocluster core ($[Ce_{24}O_{28}(OH)_8]^{30+}$) of cerium nuclearity 24 ($Ce_{24}$), demonstrating a flourite structure. It is noted two $Ce^{3+}$ ions on the outside of the core, as found in $CeO_2$ nanoparticles where surface $Ce^{4+}$ ions can be reduced to $Ce^{3+}$ FIG. 5A demonstrates a cube arrangement of the fluorite structure.
Figure 4A:
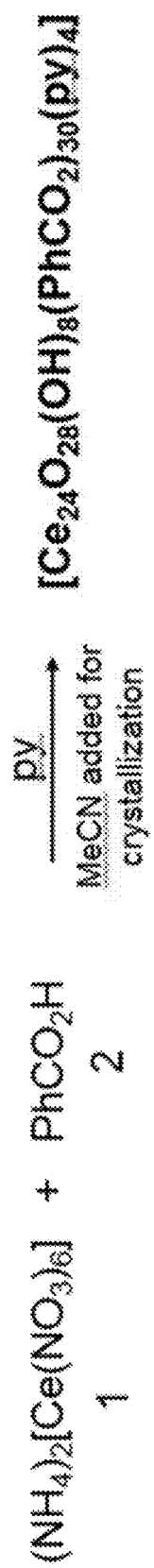
FIG. 4A illustrates a prior synthesis reaction for synthesizing a molecular cerium-oxide nanocluster of cerium nuclearity 24 ($Ce_{24}$).
Figure 4B:
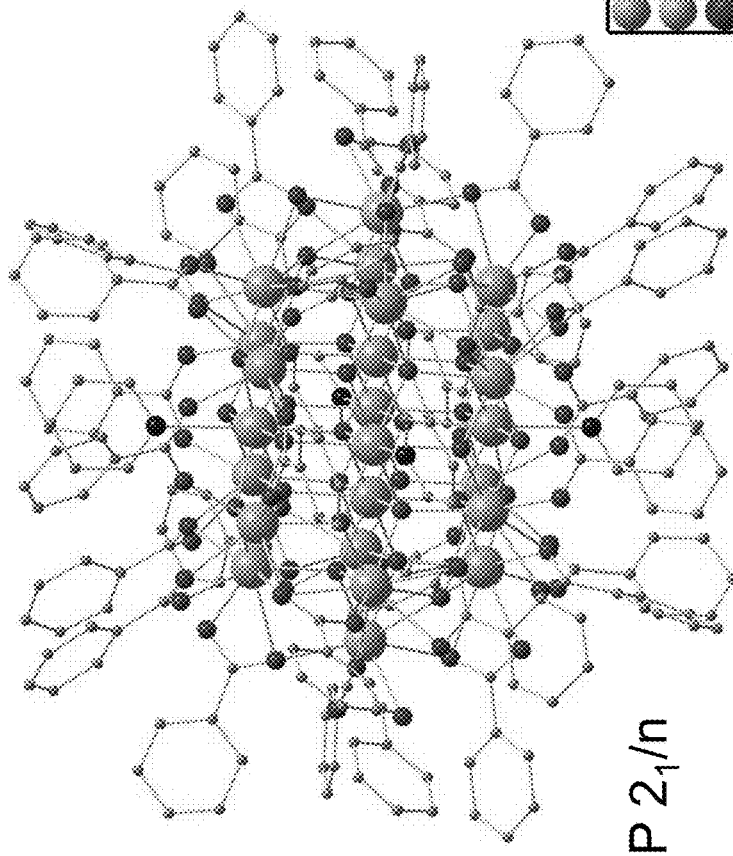
FIG. 4B depicts a structure for a molecular cerium-oxide nanocluster of cerium nuclearity 24 ($Ce_{24}$).
Figure 6A:
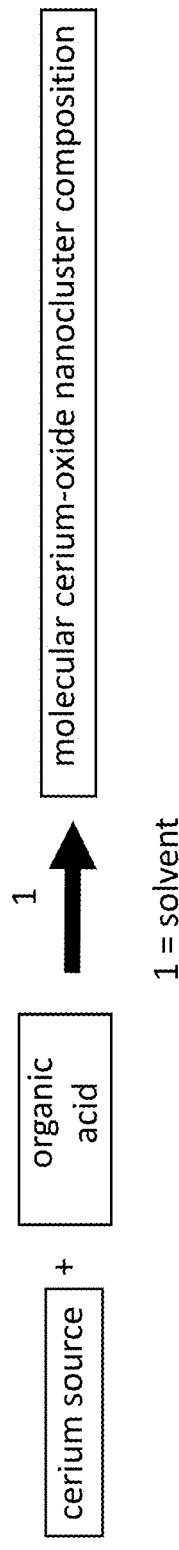
FIG. 6A shows an embodiment of a reaction scheme for synthesis of cerium-oxide nanoclusters using a cerium source and an organic acid.
Figure 6B:
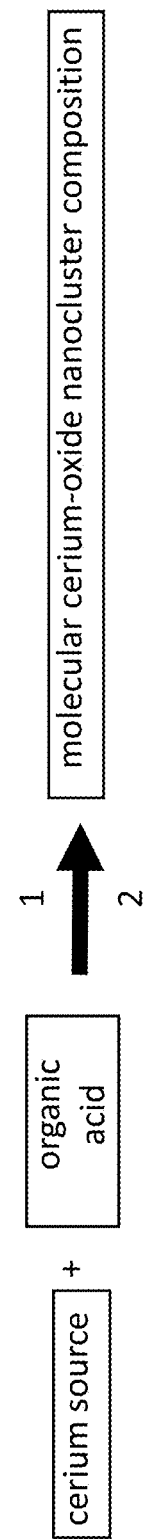
FIG. 6B shows an embodiment of a reaction scheme for synthesis of cerium-oxide nanoclusters using a cerium source, an organic acid, and a crystallization agent.
Figure 7A:
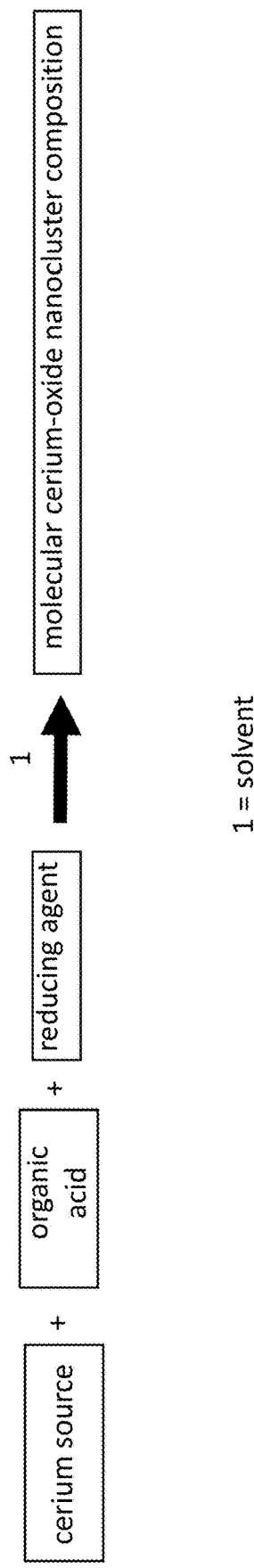
FIG. 7A shows an embodiment of a reaction scheme for synthesis of cerium-oxide nanoclusters using a cerium source, an organic acid, and a reducing agent.
Figure 7B:
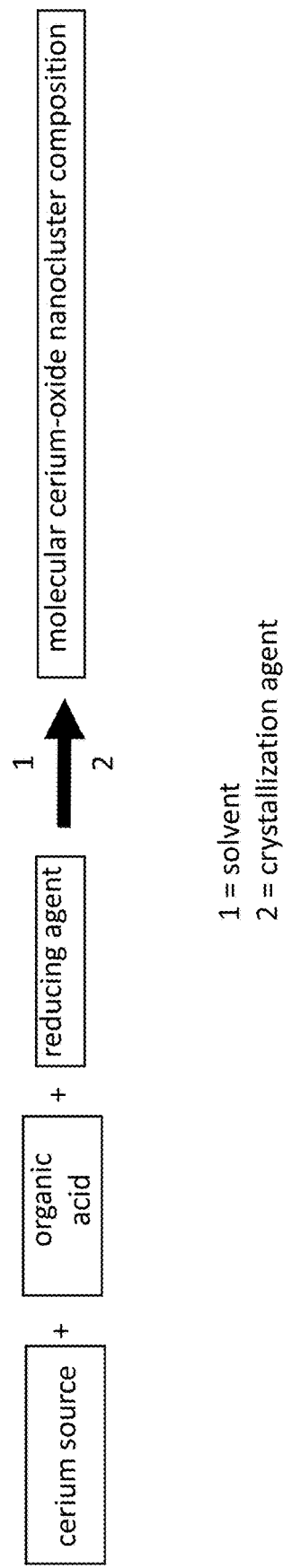
FIG. 7B shows an embodiment of a reaction scheme for synthesis of cerium-oxide nanoclusters using a cerium source, an organic acid, a reducing agent, and a crystallization agent.
Figure 8A:
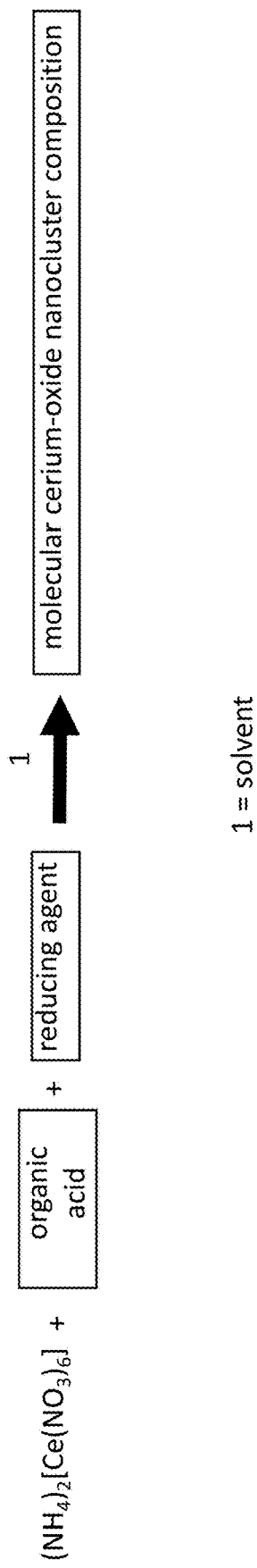
FIG. 8A illustrates an embodiment of a reaction mechanism for synthesizing molecular cerium-oxide nanoclusters according to the present disclosure.
Figure 8B:
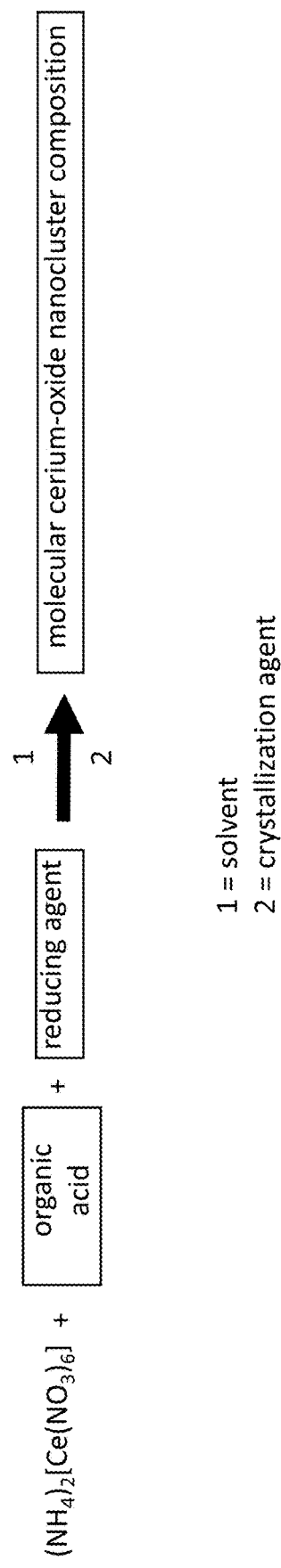
FIG. 8B illustrates an embodiment of a reaction mechanism for synthesizing molecular cerium-oxide nanoclusters according to the present disclosure.

Molecular cerium-oxide nanoclusters of cerium nuclearity 6 ($Ce_6$), 16 ($Ce_{16}$), and 24 ($Ce_{24}$) have previously been demonstrated. FIG. 2A demonstrates a synthesis reaction for a $Ce_6$ nanocluster with structure $[Ce_6O_4(OH)_4(dmb)_{12}(H_2O)_4]\cdot 4H_2O\cdot 6MeCN$, the structure of and the core of are shown in FIGS. 2B and 2C respectively. FIG. 3A demonstrates a synthesis reaction for a $Ce_{16}$ nanocluster with structure $[Ce_{16}O_{17}(OH)_6(O_2CPh)_{24}(HO_2CPh)_3(H_2O)]$, the structure of and the core of are shown in FIGS. 3B and 3C respectively. FIG. 4A demonstrates a synthesis reaction for a $Ce_{24}$ nanocluster with structure $[Ce_{24}O_{28}(OH)_8(PhCO_2)_{30}(py)_4]$, the structure of and the core of are shown in FIGS. 4B and 4C respectively. Cores of these molecular cerium-oxide nanoclusters ($Ce_6$ in FIG. 5C, $Ce_{16}$ in FIG. 5D, $Ce_{24}$ in FIG. 5E) demonstrate the fluorite structure (fluorite cube structure shown in FIG. 5A) and similarity to structure of bulk $CeO_2$ (FIG. 5B).

However, larger molecular Ce/O/$RCO_2$-clusters are formed using an additional reducing agent, which provides electrons and allows for more favorable products of larger molecular Ce/O/$RCO_2$-clusters and/or at higher yields.

In an embodiment, the molecular Ce/O/$RCO_2$-clusters can have a general formula of $[Ce_xO_y(OH)_w(H_2O)_l(RCO_2)_z(L)_m]^n$, $[Ce_xO_y(OH)_w(H_2O)_l(RPO_2)_z(L)_m]^n$, or $[Ce_xO_y(OH)_w(H_2O)_l(RPO_3)_z(L)_m]^n$, where l, m, n, w, x, y, z=0 or ± an integer number, and L=pyridine (py), MeCN or similar neutral organic molecule, or an ion such as $F^-$, $C^-$, $Br^-$, $I^-$, or similar inorganic ion such as $CN^-$, $N_3^-$, $NCO^-$, or similar. $RCO_2$, $RPO_2$, and $RPO_3$ in the above formulas can be derived from any of the organic acids described in more detail below.

In an embodiment, R can be alkyl group (such as $CH_3$, $C_2H_5$, $C_3H_7$, $C_4H_9$, $C_5H_{11}$, and longer chains, and their branched analogs, and derivatives of both types with one or more H atoms replaced by other atoms such as a halide (F, Cl, Br, I), OR' or SR' (R'=H or any alkyl group as listed)), or an aromatic group comprising one or more phenyl or similar aromatic rings, each of which can be unsubstituted or substituted at one or more H positions with an alkyl, halide or other group as described. In an embodiment, the molecular Ce/O/$RCO_2$-clusters can have the formula $[Ce_{19}O_{18}(OH)_9(PhCO_2)_{27}(py)_3(H_2O)]$.

Compositions of molecular cerium-oxide nanoclusters are described herein. A composition can be a homogenous composition comprised of similar clusters. A composition can be a non-homogenous composition that comprises clusters of the same nuclearity but different surface properties due to shifts in locations of protons. Clusters of a particular nuclearity can have different atomic configurations but retain similar shapes and properties as each other.

In an embodiment, the molecular Ce/O/$RCO_2$-cluster can be a $Ce_{19}$ cluster and have the formula $Ce_{19}O_{18}(OH)_{9-x}(H_2O)_x(PhCO_2)_{27}(py)_3$. The core can comprise or consist of 15 or 14 $Ce^{4+}$ ions and four or five $Ce^{3+}$ ions, respectively, based on BVS calculations. There can be 18 bridging O ions in the core along with 9 other atoms that can exist as $OH^-$ ions or $H_2O$ groups. While the crystallographic studies can locate the position of each atom, protons can be difficult to identify, especially for high nuclearity clusters with metals that have a large electron density. The remaining ligation can be provided by 27 $PhCO_2^-$ ligands and three terminal py ligands. The core itself (Ce—Ce) can have a diameter of 1.02 nm at its widest point and the arrangement of Ce ions and O atoms in the core displays the fluorite structure and is a molecular piece of $CeO_2$.

In an embodiment, the molecular Ce/O/$RCO_2$-cluster can be a $Ce_{24}$ cluster and have the formula $Ce_{24}O_{28}(OH)_{8-x}(H_2O)_x(PhCO_2)_{30}(py)_4$. The core of $Ce_{24}$ can comprise or consist of 21 $Ce^{4+}$ ions and three $Ce^{3+}$ ions as determined from BVS calculations. There can be 28 bridging $O^{2-}$ ions in the core that were identified based on BVS calculations along with 8-x $OH^-$ and $xH_2O$. While the crystallographic studies can locate the position of each atom, protons can be difficult to identify, especially for high nuclearity clusters with metals that have a large electron density. The remaining ligation can be provided by 30 $PhCO_2^-$ ligands along with four terminal py ligands. The core itself (Ce—Ce) can have a diameter of 1.15 nm at its widest point and the arrangement of Ce ions and O atoms in the core displays the fluorite structure and is a molecular piece of $CeO_2$.

In an embodiment, the molecular Ce/O/$RCO_2$-cluster can be a $Ce_{38}$ cluster and have the formula $Ce_{38}O_{62-x-y}(OH)_x(H_2O)_y(CH_3CH_2CO_2)_{36}(py)_8$. The core of $Ce_{38}$ again displays a fluorite structure similar to $CeO_2$. The core can comprise or consist of 38 $Ce^{4+}$ ions, based on BVS calculations arranged in an almost perfect sphere. $Ce_{38}$ can exist with another $Ce_{38}$ in the composition of asymmetric units and while both clusters are the same in terms of nuclearitity, they can be slightly different in their surface groups. While the crystallographic studies can locate the position of each atom, protons can be difficult to identify, especially for high nuclearity clusters with metals that have a large electron density. It is at this size range that the surface can become more similar to a nanoparticle surface in which the protons may be at various locations that are unidentifiable by crystallography and for BVS calculations only an average of the proton location may be observed. Protons could shuttle to various positions along the negatively charged surface with the numerous O atoms. Therefore, a generic molecular formula for this $Ce_{38}$ cluster is provided since it is clear that there are two $Ce_{38}$ molecules that can exist,. The remaining ligation can be provided by 36 $CH_3CH_2CO_2^-$ ligands, 12 can be coordinated in their familiar $\eta^1$: $\eta^1$:μ-mode and 24 can be chelating and bridging, and eight terminal py ligands. The core itself (Ce—Ce) can have a diameter of 1.18 nm at its widest point placing this molecule on the size regime of some of the smallest CNPs that have been studied to this point.

In an embodiment, the molecular Ce/O/$RCO_2$-cluster can be a $Ce_{40}$ cluster and have the formula $Ce_{40}O_{56}(OH)_x(H_2O)_{2-x}(CH_3CO_2)_{46-y}(py)_4(MeCN)_y$. The core of $Ce_{40}$ can comprise or consist of 38 $Ce^{4+}$ ions and two $Ce^{3+}$ ions as determined from BVS calculations. $Ce_{40}$ may not be as symmetric as $Ce_{38}$, and can take on more of an oval shape, but not only due to the addition of the outer $Ce^{3+}$ ions; the number of Ce ions in each Ce layer can be the same as in $Ce_{38}$ with the addition of the $Ce^{3+}$ ions in the middle two layers (7 Ce ions on the bottom layer followed by 14, 14 and 7), but can be offset or shifted with respect to the layers of $Ce_{38}$. There are 56 bridging $O_2-$ ions in the core that were identified based on BVS calculations along with 2 $OH^-$. Similar to $Ce_{38}$ there are also two molecules in the asymmetric unit that can contain the same number of Ce ions, but the ligation of the two molecules differs.. For one cluster, the remaining ligation can be provided by 46 $CH_3CO_2^-$ ligands, 14 can be coordinated in their familiar $\eta^1$: $\eta^1$:μ-mode, 20 can be chelating and bridging, eight can be in a rare $\eta^1$:$\eta^1$:$\mu_3$-mode, and four can be chelating along with four terminal py ligands. For the other cluster, the remaining ligation can be provided by 44 $CH_3CO_2^-$ ligands, 18 can be in their $\eta^1:\eta^1:\mu$-mode, 18 can be chelating and bridging, six can be in a rare $\eta^1:\eta^1:\eta^1:\mu_3$-mode, and two can be chelating along with four terminal py ligands and two bound acetonitrile ligands. This gigantic cluster is now the largest known homometallic Ce—O cluster synthesized to date and can have a diameter (Ce—Ce) of 1.60 nm at its widest point. The acetate ligands can allow this cluster to be water soluble and can provide the opportunity for studies of this cluster in aqueous media for biological applications.

Provided herein are compositions of molecular Ce/O/ $RCO_2$-clusters or molecular cerium-oxide nanoclusters. As used herein, molecular cerium-oxide nanoclusters (also referred to herein as cerium-oxide nanoclusters, nanoclusters, or clusters) can refer to individual nanoclusters and can also refer to a composition of a plurality of molecular cerium-oxide nanoclusters. Molecular cerium-oxide nanoclusters as described herein can have a crystalline structure. Molecular cerium-oxide nanoclusters as described herein can have a crystalline structure similar to the Fluorite structure.

Compositions of molecular cerium-oxide nanoclusters as described herein can be a homogenous composition, where nanoclusters of the composition have the same cerium nuclearities, similar sizes, and/or $Ce^{3+}/Ce^{4+}$ ratios. In certain embodiments, each cluster of a particular nuclearity has exactly the same size as other clusters of that same nuclearity.

As used herein, cerium nuclearity is the number of central cerium atoms in a molecular nanocluster. Cerium-oxide nanoclusters as described herein can have a cerium nuclearity of about 6 to 100 or about 19 to 40. In particular embodiments, cerium-oxide nanoclusters as described herein can have a cerium nuclearity of 19, 24, 38, and/or 40. A composition of molecular cerium-oxide nanoclusters can contain nanoclusters with the same or similar cerium nuclearity, for example a composition of molecular cerium-oxide nanoclusters can contain nanoclusters with a cerium nuclearity of 19, 24, 38, or 40.

Molecular cerium-oxide nanoclusters may also contain $Ce^{3+}$ ions positioned around the outside of the core, similar to what is observed in cerium nanoparticles. Last, a local buildup of protons can occur near areas of $Ce^{3+}$ sites in molecular cerium-oxide nanoparticles, which are also typically not surrounded by as many oxide ions as $Ce^{4+}$ sites.

As used herein, a size of a nanocluster can be an average size of a molecular cerium-oxide nanocluster, and can be a longest dimension. A longest dimension as used herein can be a longest dimension (a longest dimension can be a length, width, diameter, circumference, radius, or other such dimension) between atoms of a nanocluster or a longest dimension between cerium atoms of a nanocluster. Molecular cerium-oxide nanoclusters as described herein can have a size of about 1.1 to 4 nm or about 1.18 or 1.6 nm.

As described herein, molecular cerium-oxide nanoclusters can have a $Ce^{3+}/Ce^{4+}$ ratio of about 0 to 0.5, about 0.01 to 0.5, about 0.1 to 0.21, or about 0 to 0.21 as calculated by bond valence sums (BVS) as the number of $Ce^{3+}$ ions divided by the number of $Ce^{4+}$ ions. In an aspect, only $Ce^{3+}$ is present and in another aspect only $Ce^{4+}$ present.

In certain aspects, molecular cerium-oxide nanoclusters (or cerium nanoclusters or cerium-oxide nanoclusters) as described herein have the formula $Ce_6O_4(OH)_4(H_2O)_4(dmb)_{12}$, $Ce_{16}O_{17}(OH)_6(O_2CPh)_{24}(HO_2CPh)_3(H_2O)$, $Ce_{19}O_{18}(OH)_{10}(O_2CPh)_{26}(H_2O)(py)_3$, $Ce_{24}O_{27}(OH)_9(O_2CPh)_{30}(py)_4$, $Ce_{24}O_{28}(OH)_8(PhCO_2)_{30}(py)_4$, $Ce_{38}O_{54}(OH)_8(EtCO_2)_{36}(py)_8$, or $Ce_{40}O_{56}(OH)_2(MeCO_2)_{44}(MeCO_2H)_{2/0}(MeCN)_{0/2}(py)_4$.

Provided herein are methods of synthesis of molecular cerium-oxide nanoclusters and/or molecular cerium-oxide nanoclusters. Methods as described herein can synthesize homogenous compositions of molecular cerium-oxide nanoclusters. Methods as described herein can synthesize homogenous compositions of crystalline molecular cerium-oxide nanoclusters. FIGS. 6A-6B, 7A-7B, and 8A-8B depict embodiments of synthesis methods for embodiments of molecular cerium-oxide nanoclusters as described herein.

Methods as described herein can utilize a cerium source (such as ceric ammonium nitrate $[(NH_4)_2[Ce(NO_3)_6]$ or cerium nitrate, $Ce(NO_3)_3$) and an organic acid to synthesize cerium-oxide nanoclusters. The method can additionally include a reducing agent for the synthesis of cerium-oxide nanoclusters. The method can include a cerium source, an organic acid, a reducing agent, and a solvent. The organic acid can be a carboxylic acid or carboxylate. Organic acids can impart carboxylate groups in a nanocluster that can contribute to the regulation of nanocluster size, shape, and/or solubility.

The cerium source can contain cerium and a nitrate group. The cerium source can be ceric ammonium nitrate $(NH_4)_2[Ce(NO_3)_6]$, tetrabutylammonium cerium nitrate $(TBA)_2[Ce(NO_3)_6]$, or cerium nitrate, $Ce(NO_3)_3$. The cerium source can contain Ce in the +3 and/or +4 oxidation state as a salt with a counter ion such as nitrate, halide or similar, that is soluble in organic solvents such as pyridine with or without the addition of water.

The organic acid can be of the formula $X_1CO_2H$ or $X_1Y_1PO_2H$ or $X_1PO_3H$ or $RCO_2H$, $RPO_2H$ or $RPO_3H$, wherein $X_1$, $Y_1$, and R can each independently selected from: aromatic (e.g., phenyl (Ph), substituted phenyls, more than one connected phenyls), linear, or branched aliphatic, alicyclic or combinations of aromatic and aliphatic (e.g., alkyl group). $X_1$ and $Y_1$ can be phenyl (Ph), $CH_3$, $CH_3CH_2$, $CH(CH_3)_2$ The organic acid can be an O-containing acid such as $PhCO_2H$, $CH_3CO_2H$, $CH_3CH_2CO_2H$, $PH_2PO_2H$ or $PhPO_3H$, or other organic acids. The organic acid provides oxygen atoms that are covalently bound to the nanocluster surface helping to stabilize the structure of the core and the energetically favorable growth of the core, and can play a role in regulating molecular nanocluster size, which will be determined by varying $X_1$ and/or $Y_1$. The organic acid can be benzoic acid or benzoic acid derivatives, such as 2-methylbenzoic acid, 3-methyl-benzoic acid, or 4-methylbenzoic acid. The organic acid can also be a weaker one such as an alcohol or polyol, or a multifunctional chelate ligand with a mixture of acid and alcohol groups. The organic acid can be acetic acid or propionic acid. In certain embodiments, R is Ph, $CH_3$, or $CH_3CH_2$.

The reducing agent can contain Iodine (I). The reducing agent can be of the formula $X_2I$. $X_2$ can be Li, Na, K, Cs, Be, Mg, Ca, Sr, Ba, $PR_4$ or $NR_4$ (R=H, $CH_3$, $C_2H_5$, $C_3H_7$, $C_4H_9$, Ph, $CH_2Ph$, and similar, and combinations thereof), and the like. The reducing agent can also be sulfur-based, for example hydrazine sulfate $(H_6N_2O_4S)$, or other soluble organic or metal-based reducing agents, and including peroxide- and superoxide-containing species.

The cerium source and the organic acid can be mixed in a solvent to create a reaction mixture in a ratio of about 1 to about 2 or about 1 to about 4. In an embodiment, the ratio is about 1 to about 2. In another embodiment, the ratio is about 1 to about 4. The solvent can comprise pyridine (py) and water in a ratio of about 5:1 v/v to about 10:1 v/v. In an embodiment, the amount of water can be less than 2 mL, and if the amount of water is more than 2 mL insoluble products can form without desirable crystalline products. In an embodiment the amount of water can be about 10 mL. In an embodiment, the amount of water can be about 2 mL to about 10 mL. The mixture can optionally be stirred. The reaction can progress at a temperature of about 25° C. to about 100° C., a pressure of about 1atm to about 3 atm, and a time of about 10 mins to about 24 hours.

In an aspect, the cerium source, the organic acid, and the reducing agent can be mixed in a solvent to create a reaction mixture in a ratio of about 1 to about 2 to about 1 or about 1 to about 4 to about 1. In an embodiment, the ratio is about 1 to about 2 to about 1. In another embodiment, the ratio is about 1 to about 4 to about 1. The solvent can comprise pyridine (py) and water in a ratio of about 5:1 v/v to about 10:1 v/v. In an embodiment, the amount of water can be less than 2 mL, and if the amount of water is more than 2 mL insoluble products can form without desirable crystalline products. The mixture can optionally be stirred. The reaction can progress at a temperature of about 25° C. to about 100° C., a pressure of about 1 atm to about 3 atm, and a time of about 10 mins to about 24 hours.

A crystallization agent can be added to the reaction. The crystallization agent can contain one or more methyl groups. The crystallization agent can be of the formula $X_3Y$. $X_3$ can be a methyl group. Y can be $NO_2$ or CN. The crystallization agent can aid in the formation of crystals of the molecular cerium-oxide nanoclusters.

After the reaction has processed, crystalline solid of molecular cerium-oxide nanoclusters can be isolated with an isolation method, such as filtration through filter paper or a glass frit.

Described herein are methods of scavenging free radicals. As used herein radical scavenging can mean reducing the absolute number of free radicals, reducing the concentration of free radicals, or reducing the half-life of free radicals. Methods as described herein can reduce free radicals from a first level to a second level, wherein a first level can be an absolute number, concentration, or half-life that is greater than a second level, which can be an absolute number, concentration, or half-life.

Methods as described herein can scavenge free radicals by the administration of compositions comprising molecular cerium-oxide nanoclusters as described herein. Methods of scavenging free radicals can include one or more of reducing the number or concentration of free radicals in an environment (such as a fluid), reducing the half-life of free radicals in an environment, preventing the generation of free radicals, or accelerating the rate of free radical decay. Free radicals can be reactive oxygen species, such as hydroxide and superoxide radicals, or other radicals, such as reactive nitrogen species.

Methods as described herein can reduce the absolute number of free radicals from a first level (or number) to a second level (i.e. number), wherein the second level is lower than the first. Methods as described herein can reduce the concentration of free radicals from a first level (i.e. concentration) to a second level (i.e. concentration), wherein the second level is lower than the first. Methods as described herein can reduce the half-life of free radicals from a first level to a second level, wherein the second level is a shorter duration of time (seconds, milliseconds, etc) than the first. Methods as described herein can reduce combinations of the above.

Methods as described herein can scavenge free radicals by the administration of compositions comprising molecular cerium-oxide nanoclusters as described herein, and can accelerate physiological and non-physiological rates of free radical decay, wherein free radical decay is a reduction in one or more of free radical amount, concentration, or half-life over time. Compositions and methods as described herein can reduce one or more of the amount, concentration, or half-life of one or more free radical species at a faster rate than the free radical species would decay without compositions and methods as described herein.

Also described herein is a method of scavenging reactive oxygen species (ROS) or other physiological or non-physiological intra-cellular or extra-cellular free radicals. In embodiments of methods as described herein, a composition containing one or more cerium-oxide nanoclusters can be introduced into an environment containing reactive oxygen species, and the composition can reduce the amount of reactive oxygen species from a first level to a second level, the first level being higher than the second. In certain aspects, an exemplary embodiment of an ROS which can be scavenged is a hydroxyl radical (OH·) or superoxide radical ($O_2$·). One of skill in the art would recognize that although embodiments as described herein are directed to reactive oxygen species, compositions and methods as described herein are not limited to reactive oxygen species, and can relate to other radical species, such as reactive nitrogen species, for example.

In certain embodiments, a composition containing one or more cerium-oxide nanoclusters can be administered to a subject in need thereof. A subject in need thereof can be a subject (i.e., a cell, a rodent, a human, etc.) containing one or more living cells which may be subject to cellular or sub-cellular damage caused by reactive oxygen species or other intra-cellular or extra-cellular radical species. The composition administered to a subject in need thereof can reduce reactive oxygen species in or around the subject from a first level to a second level, where the first level is higher than the first. The composition administered to a subject in need thereof can reduce half-life of reactive oxygen species in or around the subject from a first level to a second level, where the second level is a shorter duration of time than the first level. The composition administered to a subject in need thereof can otherwise scavenge radicals in the subject.

In certain embodiments, the method includes treating a subject (i.e. a subject in need thereof) having undergoing or subject to oxidative stress. Such subjects can have an increased level of reactive oxygen species or radical species or can be subject to a risk of such and can be treated or prophylactically treated by the administration of a pharmaceutical composition to the subject in need thereof. Pharmaceutical compositions as described herein can comprise one or more molecular cerium-oxide nanoclusters as described herein and one or more pharmaceutically acceptable carriers (described in further detail below).

Methods of treatment as described herein can reduce the level of reactive oxygen species or radical species in the subject from a first level to a second level, wherein the second level is lower than the first. Methods of treatment as described herein can reduce the level of reactive oxygen species or radical species in or around one or more cells of the subject from a first level to a second level, wherein the second level is lower than the first. Methods of treatment as described herein can reduce the half-life of reactive oxygen species or other radical species in the subject from a first level to a second level, wherein the second level is a shorter duration of time than the first. Methods of treatment as described herein can reduce the half-life of reactive oxygen species or other radicals in or around one or more cells of the subject from a first level to a second level, wherein the second level is a shorter duration of time than the first. Methods as described herein can scavenge reactive oxygen species or radical species in a subject in need thereof.

A subject can be a subject, as defined herein, in need of treatment. A subject in need thereof can be a subject with a total level of free radicals or reactive oxygen species higher (absolute numbers, concentrations, half-life, numbers of species, or other factors) than a normal level as a result of a diseased state and/or an increased level of oxidative stress on the cellular level. A subject in need thereof can be a subject with a level of free radicals or reactive oxygen species in one or more populations of cells or organs (such as the brain, heart, lungs, etc) higher than a normal level as a result of a diseased state and/or an increased level of oxidative stress on the cellular level.

As described, a subject in need thereof can be a subject under conditions of oxidative stress (in aspects in one or more cells or one or more populations of cells), an imbalance is created in which over-abundant reactive oxygen species (ROS) overwhelm cellular defenses—typically regulated and protected by antioxidants—and thus damage biological cells. There are many pathological conditions in which oxidative stress plays an important role in the pathogenesis of the condition, such as cancer, stroke, Alzheimer's, inflammation, or neurodegeneration.

In certain embodiments, oxidative stress and/or an increased level of reactive oxygen species or other free radicals can be caused in subjects by one or more of cancer, stroke, Alzheimer's, inflammation, or neurodegeneration.

The methods as described herein can include delivering to a subject in need thereof, a pharmaceutical composition that includes a therapeutically effective amount of a compound (e.g., compounds A-D), or a pharmaceutically acceptable salt of the compound, and a pharmaceutically acceptable carrier, to treat the subject with an increased level of reactive oxygen species (i.e. scavenge excess reactive oxygen species) or other free radicals. As used herein, a therapeutically effective amount of a compound can be an amount of compound effective to reduce the level of free radicals or reactive oxygen species from a first level to a second level, where the first level is higher than the second. As used herein, a therapeutically effective amount of a compound can be an amount of compound effective to reduce the half-life of free radicals or reactive oxygen species from a first level to a second level, where the second level is a shorter duration of time than the first. Examples of concentrations which can comprise an effective amount are described below in the examples section and figures.

It should be noted that the therapeutically effective amount to result in uptake of the compound into the subject can depend upon a variety of factors, including for example, the age, body weight, general health, sex, and diet of the subject; the time of administration; the route of administration; the rate of excretion of the specific compound employed; the duration of the treatment; the existence of other drugs used in combination or coincidental with the specific composition employed; the type(s) of bacteria; and like factors well known in the medical arts.

Preparation of embodiments of the compounds is described in the Example.

Pharmaceutical Formulations and Routes of Administration

Embodiments of the present disclosure include a compound (comprising one or more molecular cerium nanoclusters) as identified herein and formulated with one or more pharmaceutically acceptable excipients, diluents, carriers and/or adjuvants. In addition, embodiments of the present disclosure include a compound formulated with one or more pharmaceutically acceptable auxiliary substances. In particular the compound can be formulated with one or more pharmaceutically acceptable excipients, diluents, carriers, and/or adjuvants to provide an embodiment of a composition of the present disclosure.

A wide variety of pharmaceutically acceptable excipients are known in the art. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In an embodiment of the present disclosure, the compound can be administered to the subject using any means capable of resulting in the desired effect. Thus, the compound can be incorporated into a variety of formulations for therapeutic administration. For example, the compound can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, the compound may be administered in the form of its pharmaceutically acceptable salts, or a subject active composition may be used alone or in appropriate association, as well as in combination, with other pharmaceutically active compounds. The following methods and excipients are merely exemplary and are in no way limiting.

For oral preparations, the compound can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Embodiments of the compound can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Embodiments of the compound can be utilized in aerosol formulation to be administered via inhalation. Embodiments of the compound can be formulated into pressurized acceptable propellants such as dichlorodifluoromethane, propane, nitrogen and the like.

Furthermore, embodiments of the compound can be made into suppositories by mixing with a variety of bases such as emulsifying bases or water-soluble bases. Embodiments of the compound can be administered rectally via a suppository. The suppository can include vehicles such as cocoa butter, carbowaxes and polyethylene glycols, which melt at body temperature, yet are solidified at room temperature.

Unit dosage forms for oral or rectal administration, such as syrups, elixirs, and suspensions, may be provided wherein each dosage unit, for example, teaspoonful, tablespoonful, tablet or suppository, contains a predetermined amount of the composition containing one or more compositions. Similarly, unit dosage forms for injection or intravenous administration may comprise the compound in a composition as a solution in sterile water, normal saline or another pharmaceutically acceptable carrier.

Embodiments of the compound can be formulated in an injectable composition in accordance with the disclosure. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles in accordance with the present disclosure.

In an embodiment, the compound can be formulated for delivery by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

Mechanical or electromechanical infusion pumps can also be suitable for use with the present disclosure. Examples of such devices include those described in, for example, U.S. Pat. Nos. 4,692,147; 4,360,019; 4,487,603; 4,360,019; 4,725,852; 5,820,589; 5,643,207; 6,198,966; and the like. In general, delivery of the compound can be accomplished using any of a variety of refillable, pump systems. Pumps provide consistent, controlled release over time. In some embodiments, the compound can be in a liquid formulation in a drug-impermeable reservoir, and is delivered in a continuous fashion to the individual.

In one embodiment, the drug delivery system is an at least partially implantable device. The implantable device can be implanted at any suitable implantation site using methods and devices well known in the art. An implantation site is a site within the body of a subject at which a drug delivery device is introduced and positioned. Implantation sites include, but are not necessarily limited to, a subdermal, subcutaneous, intramuscular, or other suitable site within a subject's body. Subcutaneous implantation sites are used in some embodiments because of convenience in implantation and removal of the drug delivery device.

Drug release devices suitable for use in the disclosure may be based on any of a variety of modes of operation. For example, the drug release device can be based upon a diffusive system, a convective system, or an erodible system (e.g., an erosion-based system). For example, the drug release device can be an electrochemical pump, osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, etc.

Drug release devices based upon a mechanical or electromechanical infusion pump can also be suitable for use with the present disclosure. Examples of such devices include those described in, for example, U.S. Pat. Nos. 4,692,147; 4,360,019; 4,487,603; 4,360,019; 4,725,852, and the like. In general, a subject treatment method can be accomplished using any of a variety of refillable, non-exchangeable pump systems. Pumps and other convective systems are generally preferred due to their generally more consistent, controlled release over time. Osmotic pumps are used in some embodiments due to their combined advantages of more consistent controlled release and relatively small size (see, e.g., PCT published application no. WO 97/27840 and U.S. Pat. Nos. 5,985,305 and 5,728,396). Exemplary osmotically-driven devices suitable for use in the disclosure include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like.

In some embodiments, the drug delivery device is an implantable device. The drug delivery device can be implanted at any suitable implantation site using methods and devices well known in the art. As noted herein, an implantation site is a site within the body of a subject at which a drug delivery device is introduced and positioned. Implantation sites include, but are not necessarily limited to a subdermal, subcutaneous, intramuscular, or other suitable site within a subject's body.

In some embodiments, an active agent (e.g., compounds A-D) can be delivered using an implantable drug delivery system, e.g., a system that is programmable to provide for administration of the agent. Exemplary programmable, implantable systems include implantable infusion pumps. Exemplary implantable infusion pumps, or devices useful in connection with such pumps, are described in, for example, U.S. Pat. Nos. 4,350,155; 5,443,450; 5,814,019; 5,976,109; 6,017,328; 6,171,276; 6,241,704; 6,464,687; 6,475,180; and 6,512,954. A further exemplary device that can be adapted for the present disclosure is the Synchromed infusion pump (Medtronic).

Suitable excipient vehicles for the compound are, for example, water, saline, dextrose, glycerol, ethanol, or the like, and combinations thereof. In addition, if desired, the vehicle may contain minor amounts of auxiliary substances such as wetting or emulsifying agents or pH buffering agents. Methods of preparing such dosage forms are known, or will be apparent upon consideration of this disclosure, to those skilled in the art. See, e.g., Remington's Pharmaceutical Sciences, Mack Publishing Company, Easton, Pennsylvania, 17th edition, 1985. The composition or formulation to be administered will, in any event, contain a quantity of the compound adequate to achieve the desired state in the subject being treated.

Compositions of the present disclosure can include those that comprise a sustained-release or controlled release matrix. In addition, embodiments of the present disclosure can be used in conjunction with other treatments that use sustained-release formulations. As used herein, a sustained-release matrix is a matrix made of materials, usually polymers, which are degradable by enzymatic or acid-based hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Illustrative biodegradable matrices include a polylactide matrix, a polyglycolide matrix, and a polylactide co-glycolide (co-polymers of lactic acid and glycolic acid) matrix.

In another embodiment, the pharmaceutical composition of the present disclosure (as well as combination compositions) can be delivered in a controlled release system. For example, the compound may be administered using intravenous infusion, an implantable osmotic pump, a transdermal patch, liposomes, or other modes of administration. In one embodiment, a pump may be used (Sefton (1987). CRC Crit. Ref. Biomed. Eng. 14:201; Buchwald et al. (1980). Surgery 88:507; Saudek et al. (1989). N. Engl. J. Med. 321:574). In another embodiment, polymeric materials are used. In yet another embodiment a controlled release system is placed in proximity of the therapeutic target thus requiring only a fraction of the systemic dose. In yet another embodiment, a controlled release system is placed in proximity of the therapeutic target, thus requiring only a fraction of the systemic. Other controlled release systems are discussed in the review by Langer (1990). Science 249:1527-1533.

In another embodiment, the compositions of the present disclosure (as well as combination compositions separately or together) include those formed by impregnation of the compound described herein into absorptive materials, such as sutures, bandages, and gauze, or coated onto the surface of solid phase materials, such as surgical staples, zippers and catheters to deliver the compositions. Other delivery systems of this type will be readily apparent to those skilled in the art in view of the instant disclosure.

Dosages

Embodiments of the compound can be administered to a subject in one or more doses. Those of skill will readily appreciate that dose levels can vary as a function of the specific the compound administered, the severity of the symptoms and the susceptibility of the subject to side effects. Preferred dosages for a given compound are readily determinable by those of skill in the art by a variety of means.

In an embodiment, multiple doses of the compound are administered. The frequency of administration of the compound can vary depending on any of a variety of factors, e.g., severity of the symptoms, and the like. For example, in an embodiment, the compound can be administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid). As discussed above, in an embodiment, the compound is administered continuously.

The duration of administration of the compound analogue, e.g., the period of time over which the compound is administered, can vary, depending on any of a variety of factors, e.g., patient response, etc. For example, the compound in combination or separately, can be administered over a period of time of about one day to one week, about two weeks to four weeks, about one month to two months, about two months to four months, about four months to six months, about six months to eight months, about eight months to 1 year, about 1 year to 2 years, or about 2 years to 4 years, or more.

Routes of Administration

Embodiments of the present disclosure provide methods and compositions for the administration of the active agent (e.g., the compound) to a subject (e.g., a human) using any available method and route suitable for drug delivery, including in vivo and ex vivo methods, as well as systemic and localized routes of administration.

Routes of administration include intranasal, intramuscular, intratracheal, subcutaneous, intradermal, topical application, intravenous, rectal, nasal, oral, and other enteral and parenteral routes of administration. Routes of administration may be combined, if desired, or adjusted depending upon the agent and/or the desired effect. An active agent (e.g., the compound) can be administered in a single dose or in multiple doses.

Embodiments of the compound can be administered to a subject using available conventional methods and routes suitable for delivery of conventional drugs, including systemic or localized routes. In general, routes of administration contemplated by the disclosure include, but are not limited to, enteral, parenteral, or inhalational routes.

Parenteral routes of administration other than inhalation administration include, but are not limited to, topical, transdermal, subcutaneous, intramuscular, intraorbital, intracapsular, intraspinal, intrasternal, and intravenous routes, i.e., any route of administration other than through the alimentary canal. Parenteral administration can be conducted to effect systemic or local delivery of the compound. Where systemic delivery is desired, administration typically involves invasive or systemically absorbed topical or mucosal administration of pharmaceutical preparations.

In an embodiment, the compound can also be delivered to the subject by enteral administration. Enteral routes of administration include, but are not limited to, oral and rectal (e.g., using a suppository) delivery.

Methods of administration of the compound through the skin or mucosa include, but are not limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" that deliver their product continuously via electric pulses through unbroken skin for periods of several days or more.

While embodiments of the present disclosure are described in connection with the Examples and the corresponding text and figures, there is no intent to limit the disclosure to the embodiments in these descriptions. On the contrary, the intent is to cover all alternatives, modifications, and equivalents included within the spirit and scope of embodiments of the present disclosure.

ABBREVIATIONS

Ph: phenyl; Me: methyl; py: pyridine; BVS: bond valence sums; Ce: cerium.

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

A molecular cerium-oxide nanocluster having a nuclearity of 19 ($Ce_{19}$) can be synthesized according to the following reaction mechanism with a yield of about 25% or greater:

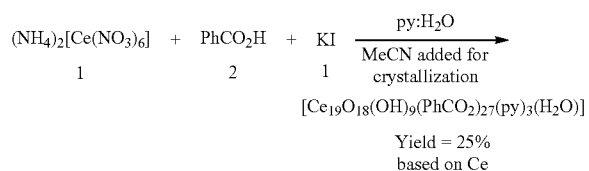

$[Ce_{19}O_{18}(OH)_9(PhCO_2)_{27}(py)_3(H_2O)]$

Yield = 25% based on Ce

Figure 9A:
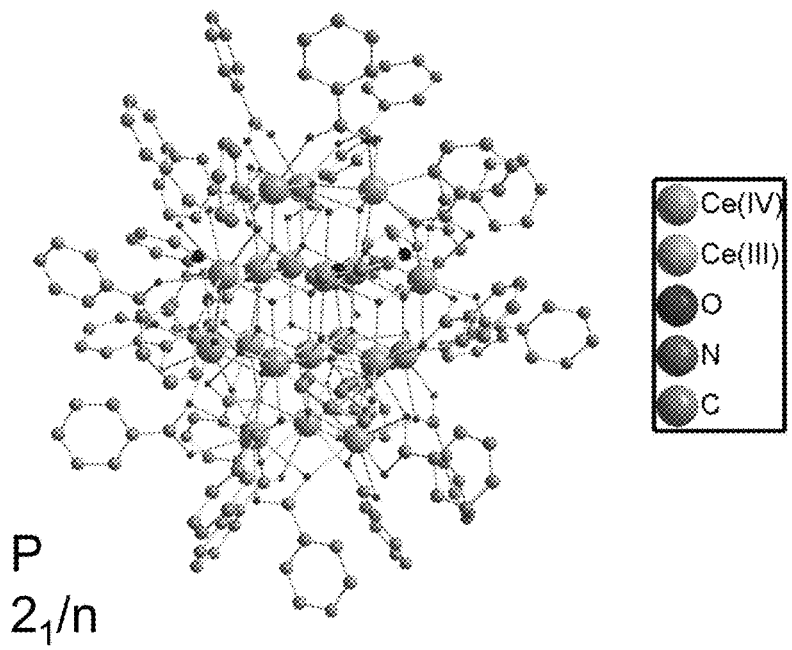
FIG. 9A shows the structure of an embodiment of a molecular cerium-oxide nanocluster with cerium nuclearity 19 ($Ce_{19}$) according to the present disclosure.
Figure 9B:
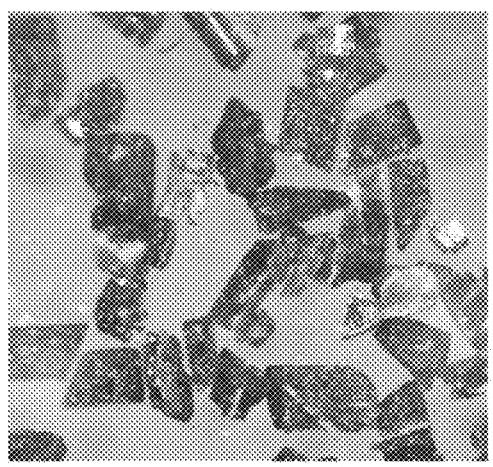
FIG. 9B is a picture of $Ce_{19}$ crystals according to compositions and methods the present disclosure.
Figure 9C:
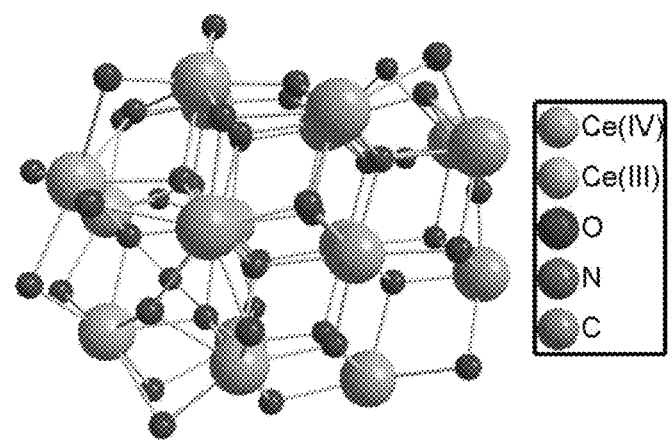
FIG. 9C depicts the structure of an embodiment of a molecular cerium-oxide nanocluster with cerium nuclearity 19 ($Ce_{19}$) core according to the present disclosure, highlighting the flourite structure within.
Figures 10A, 10B:
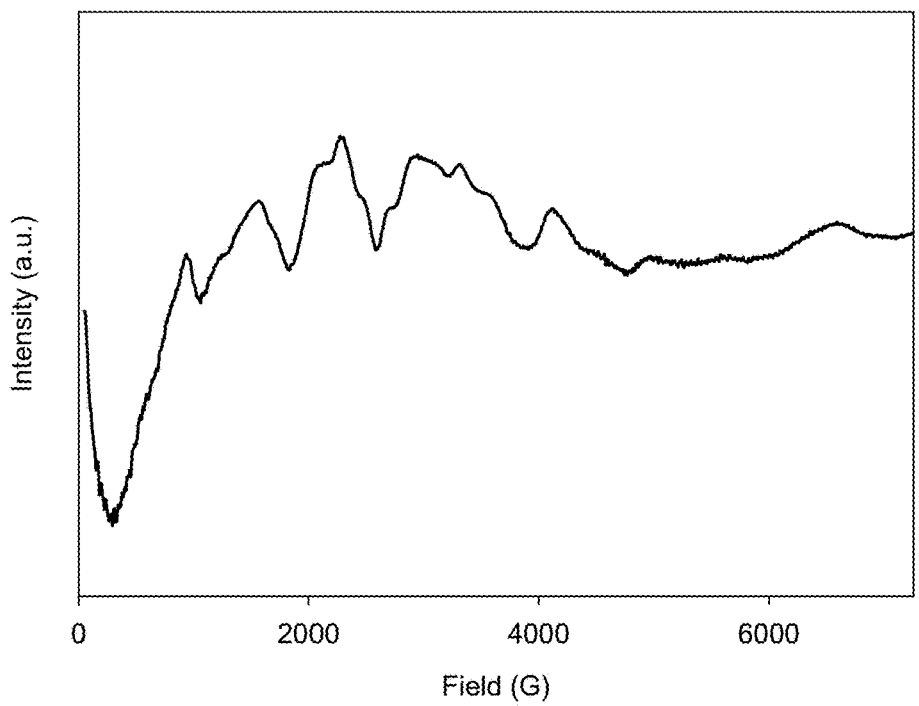
FIG. 10A shows electron paramagnetic resonance (EPR) measurements which illustrate a high $Ce^{3+}:Ce^{4+}$ ratio for an embodiment of of a molecular cerium-oxide nanocluster with cerium nuclearity 19 ($Ce_{19}$).
FIG. 10B show bond valence sums of $Ce^{3+}$ and $Ce^{4+}$ for cerium-oxide nanoclusters of various nuclearities.
Figures 10C, 10D:
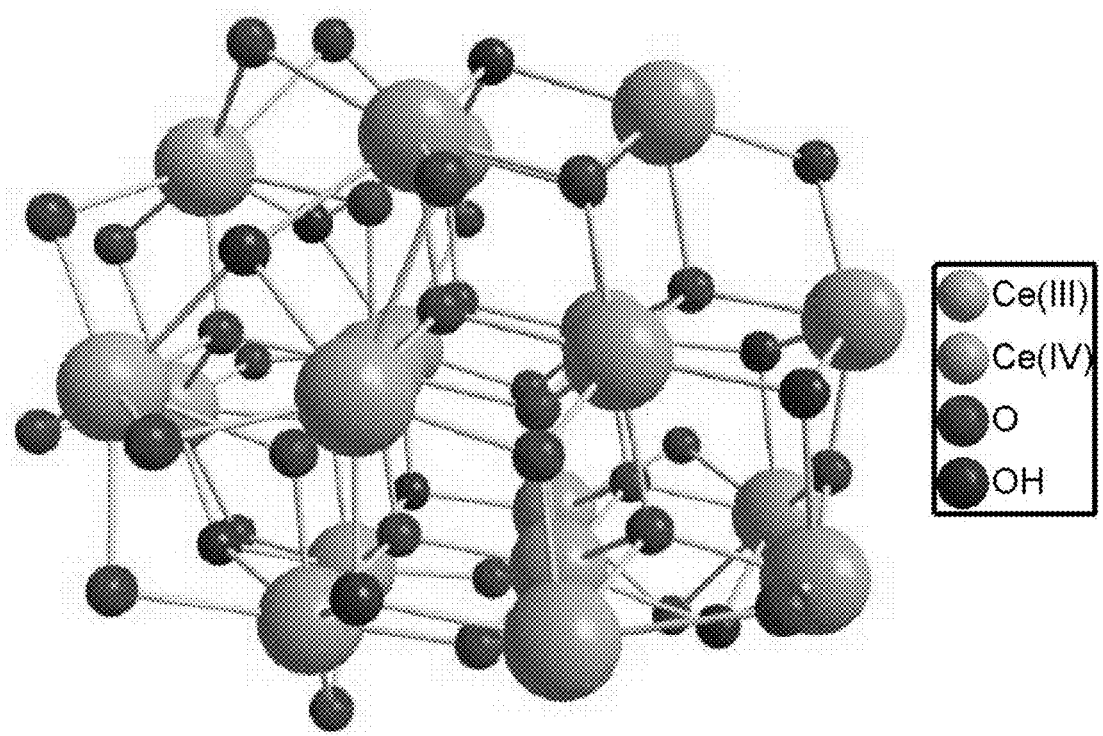
FIG. 10C shows localization of OH groups in a $Ce_{19}$ nanocluster.
FIG. 10D demonstrates oxidation states and coordination numbers for some of the Ce ions in the $Ce_{19}$ nanocluster.

The numbers 1 and 2 in the above reaction can denote proportions or ratios. An illustration of a structure of a molecular $Ce_{19}$ cluster can be seen in FIG. 9A and $Ce_{19}$ crystals are shown in the picture of FIG. 9B. An illustration of a structure of a core of a molecular $Ce_{19}$ cluster can be seen in FIG. 9C. FIG. 10A shows EPR measurements, and the EPR spectrum confirms the presence of unpaired electrons from $Ce^{3+}$ (S=1/2, I=0, $^2F_{5/2}$) ions. EPR measurements were collected on a crystalline power at 5 K in the 0 to 7000 G field range in perpendicular mode. $Ce_{19}$ can have a high $Ce^{3+}:Ce^{4+}$ ratio as shown in FIGS. 10A and 10B. Additionally, FIG. 10C shows localization of OH groups in a $Ce_{19}$ nanocluster and FIG. 10D demonstrates oxidation states and coordination numbers for some of the Ce ions in $Ce_{19}$.

Example 2

A molecular cerium-oxide nanocluster having a nuclearity of 19 ($Ce_{19}$) can be synthesized according to the following reaction mechanism with a yield of about 25% or greater (based on Ce):

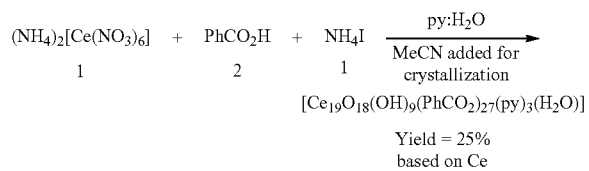

$[Ce_{19}O_{18}(OH)_9(PhCO_2)_{27}(py)_3(H_2O)]$

Yield = 25% based on Ce

The numbers 1 and 2 in the above reaction can denote proportions or ratios. An illustration of a structure of a molecular $Ce_{19}$ cluster can be seen in FIG. 9A and $Ce_{19}$ crystals are shown in the picture of FIG. 9B. An illustration of a structure of a core of a molecular $Ce_{19}$ cluster can be seen in FIG. 9C. $Ce_{19}$ can have a high $Ce^{3+}:Ce^{4+}$ ratio as shown in FIGS. 10A and 10B. Additionally, FIG. 10C shows localization of OH groups in a $Ce_{19}$ nanocluster and FIG. 10D demonstrates oxidation states and coordination numbers for some of the Ce ions in $Ce_{19}$.

Example 3

A molecular cerium-oxide nanocluster having a nuclearity of 38 ($Ce_{38}$) can be synthesized according to the following reaction mechanism:

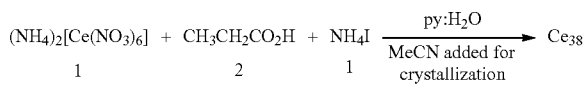

Figure 11A:
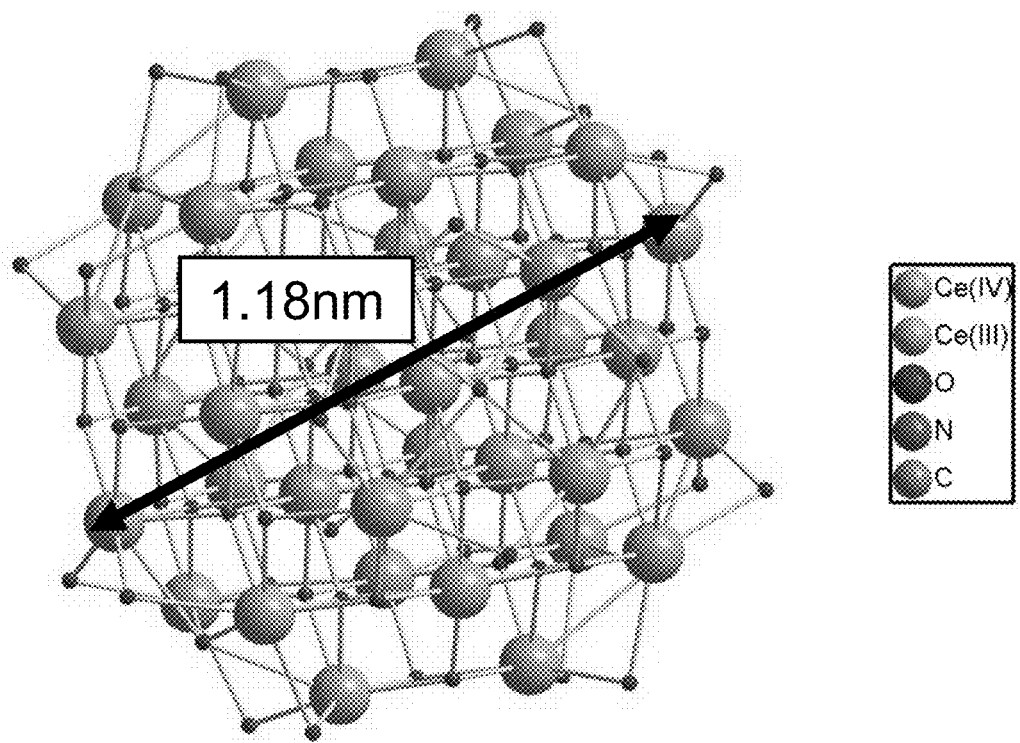
FIG. 11A illustrates the structure of an embodiment of a molecular cerium-oxide nanocluster with cerium nuclearity 38 ($Ce_{38}$) according to the present disclosure, as well as its size.
Figure 11B:
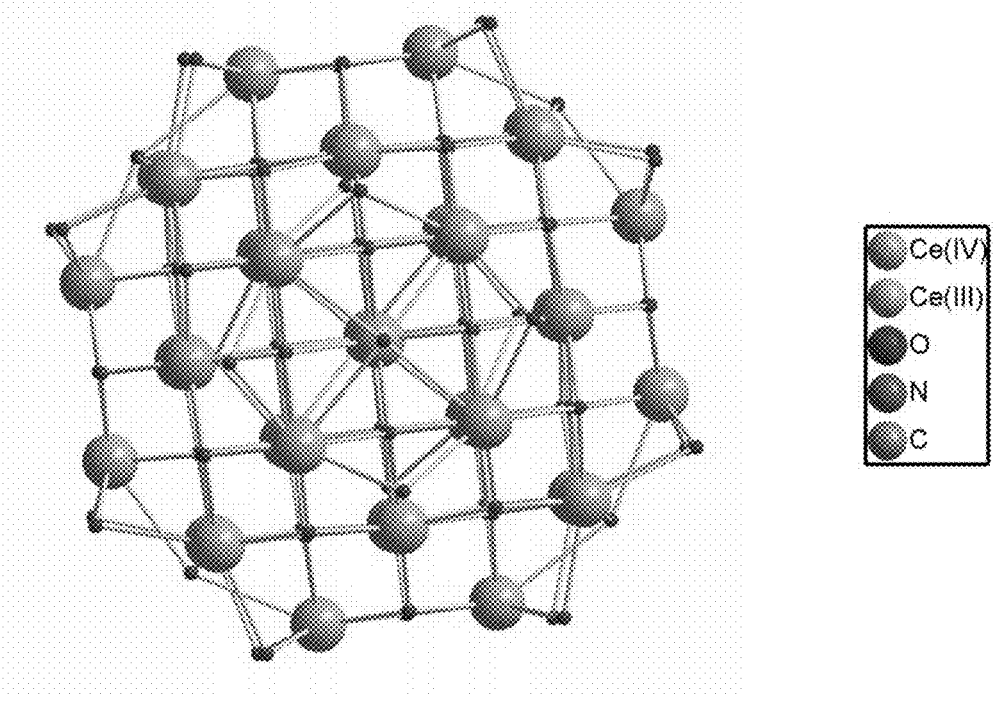
FIG. 11B demonstrates the structure of an embodiment of a molecular cerium-oxide nanocluster with cerium nuclearity 38 ($Ce_{38}$) core according to the present disclosure, highlighting the flourite structure within.

The numbers 1 and 2 in the above reaction can denote proportions or ratios. An illustration of a structure of a molecular $Ce_{38}$ cluster can be seen in FIG. 19B. An illustration of a structure of a core of a molecular $Ce_{38}$ cluster can be seen in FIG. 19C. $Ce_{38}$ can have a longest dimension between Ce atoms of about 1.18 nm as shown in FIG. 11A.

Example 4

A molecular cerium-oxide nanocluster having a nuclearity of 40 ($Ce_{40}$) can be synthesized according to the following reaction mechanism:

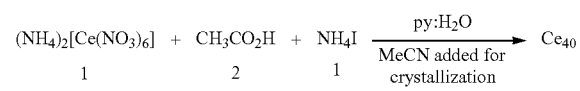

Figure 12A:
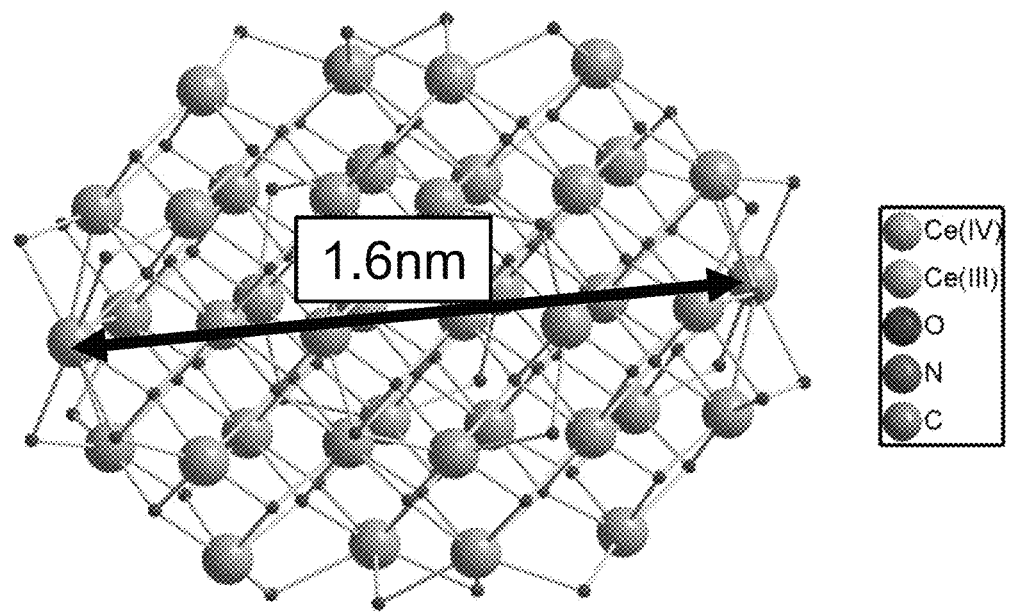
FIG. 12A shows the structure of an embodiment of a molecular cerium-oxide nanocluster with cerium nuclearity 40 ($Ce_{40}$) according to the present disclosure, as well as its size.
Figure 12B:
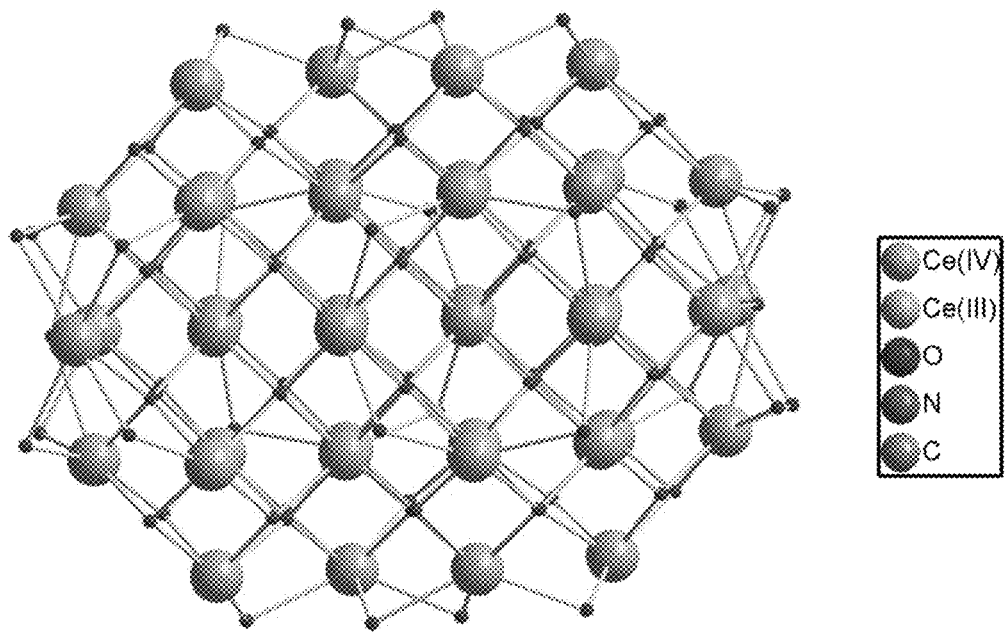
FIG. 12B depicts the structure of an embodiment of molecular cerium-oxide nanocluster with cerium nuclearity 40 ($Ce_{40}$) core according to the present disclosure, highlighting the flourite structure within.
Figure 25A:
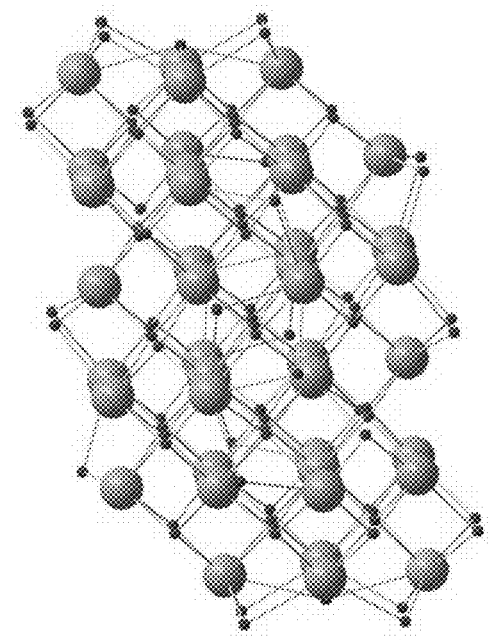
FIG. 25A illustrates a synthesis reaction for synthesizing a molecular cerium-oxide nanocluster of cerium nuclearity 40 ($Ce_{40}$).
Figure 25C:
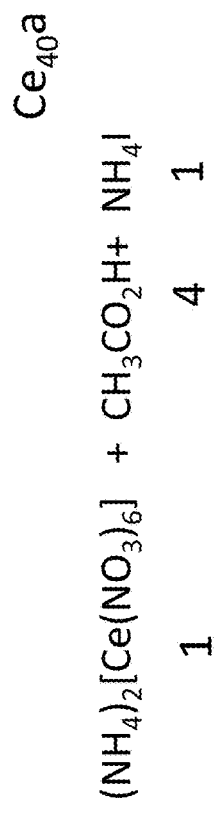
FIG. 25C shows a structure for a molecular cerium-oxide nanocluster core of cerium nuclearity 40 ($Ce_{40}$), demonstrating the flourite structure.
Figure 25B:
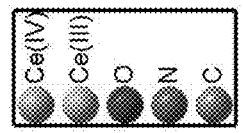
FIG. 25B depicts a structure for a molecular cerium-oxide nanocluster of cerium nuclearity 40 ($Ce_{40}$).
Figure 25B:
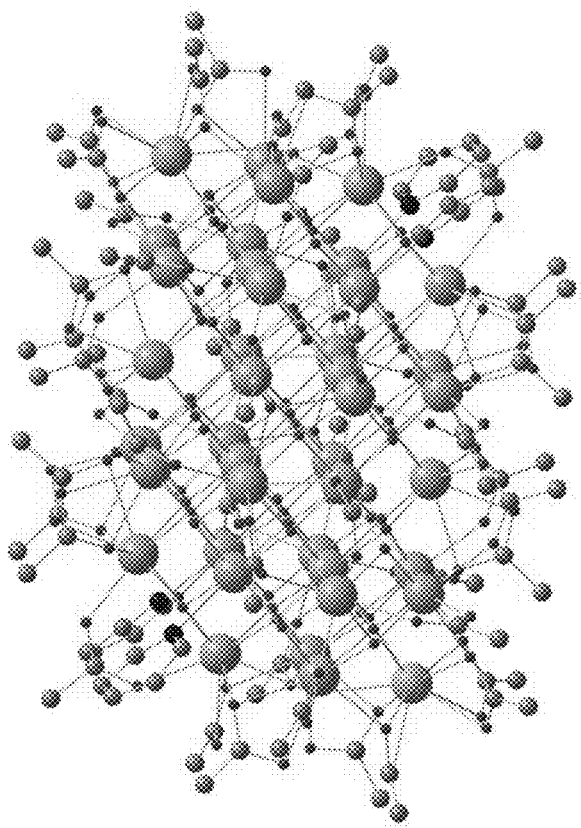
Figure 25B:

The numbers 1 and 2 in the above reaction can denote proportions or ratios. An illustration of a structure of a molecular $Ce_{40}$ cluster can be seen in FIG. 25B. An illustration of a structure of a core of a molecular $Ce_{40}$ cluster can be seen in FIG. 25C. $Ce_{40}$ can have a longest dimension between Ce atoms of about 1.6 nm as shown in FIG. 12A.

Example 5

Figures 14A, 14B:
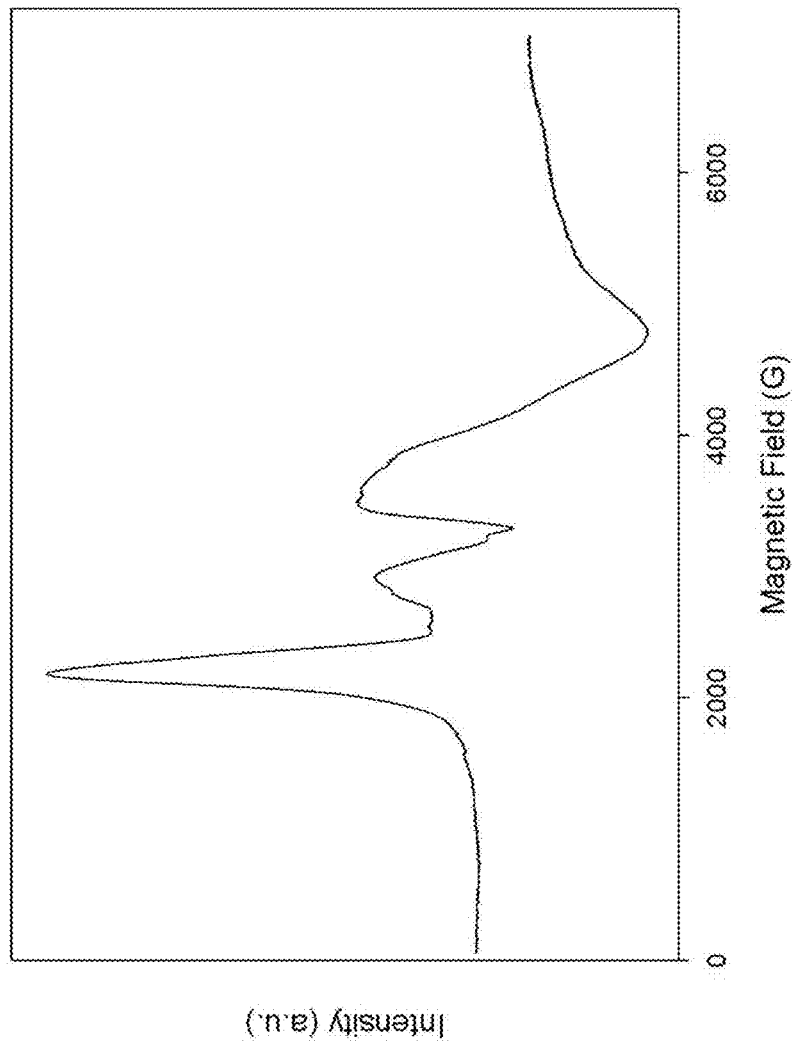
FIG. 14A shows an EPR spectrum of an embodiment of a $Ce_{24}$ nanocluster.
FIG. 14B shows bond valence sums of $Ce^{3+}$ and $Ce^{4+}$ for a cerium-oxide nanocluster of nuclearity 24 ($Ce_{24}$).
Figure 16:
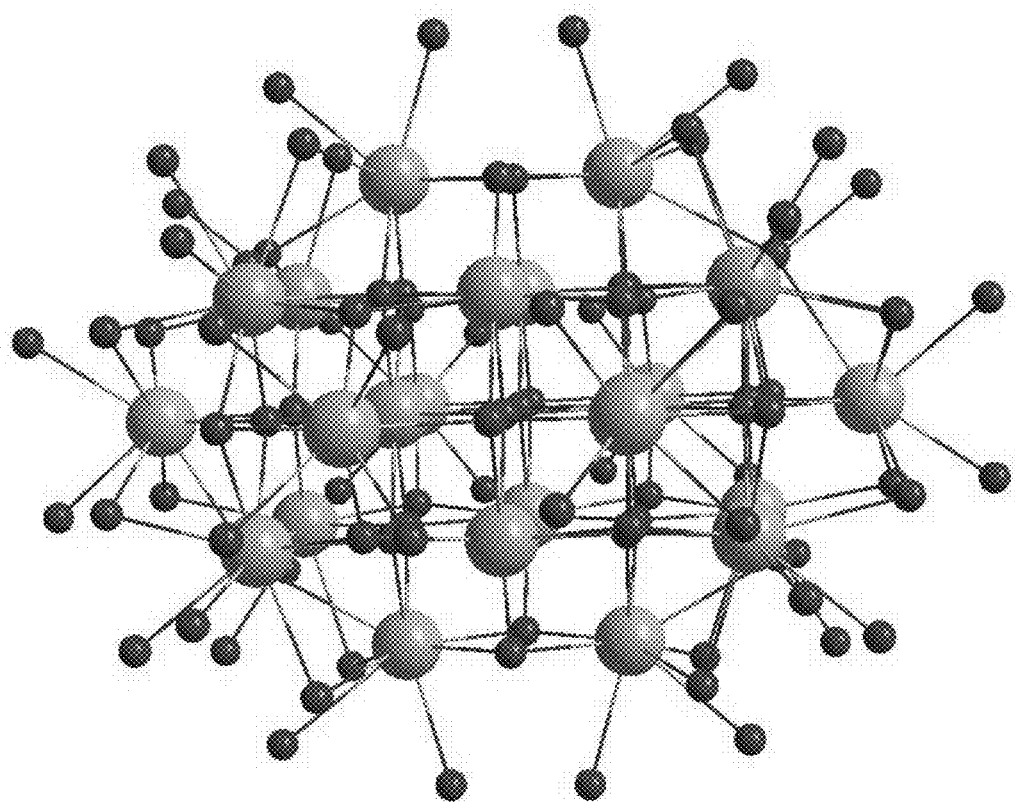
FIG. 16 illustrates the flourite structure of an embodiment of a cerium-oxide nanocluster, $Ce_{24}$.

Embodiments of molecular cerium-oxide nanoclusters of nuclearity 24 ($Ce_{24}$) are synthesized according to the embodiment of the reaction mechanism shown in FIG. 13A. An illustration of a structure of a molecular $Ce_{24}$ cluster can be seen in FIG. 13B. An illustration of a structure of a core of a molecular $Ce_{24}$ cluster can be seen in FIG. 13C. FIG. 14A shows an EPR spectrum of $Ce_{24}$. The EPR spectrum confirms the presence of unpaired electrons from $Ce^{3+}$ (S=1/2, I=0, $^2F_{5/2}$) ions. EPR measurements were collected on a crystalline power at 10K in the 0 to 7000 G field range. FIGS. 14B, 15A, and 15B show BVS values for $Ce_{24}$. FIG. 16 shows a depiction of the fluorite structure of $Ce_{24}$.

Example 6

Figure 21:
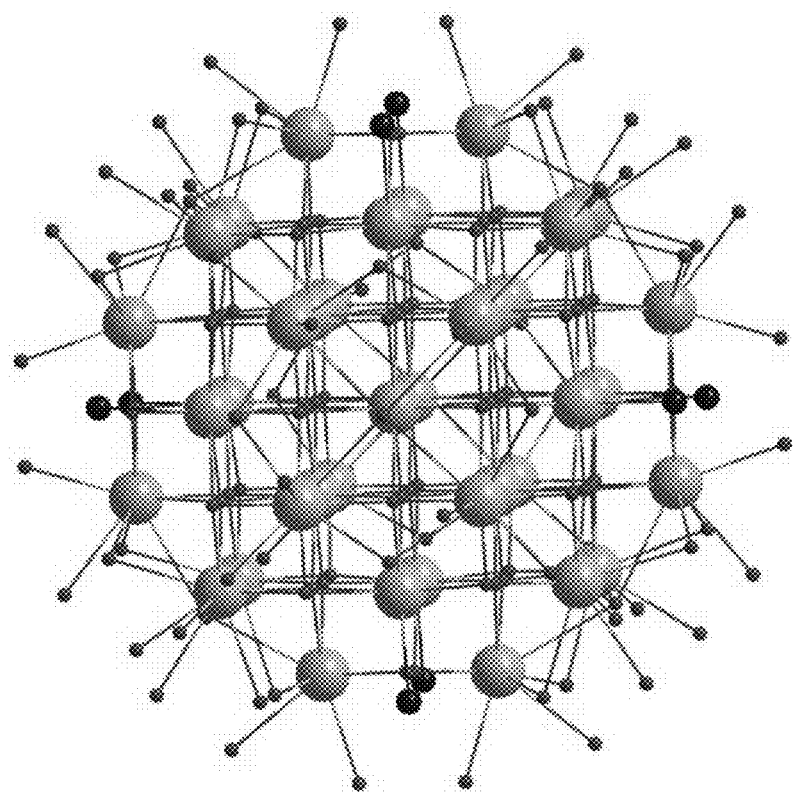
FIG. 21 depicts the flourite structure of molecular cerium-oxide nanocluster core of cerium nuclearity 38 ($Ce_{38}$).

Embodiments of molecular cerium-oxide nanoclusters of nuclearity 38 ($Ce_{38}a$ and $Ce_{38}b$) are synthesized. FIGS. 17A and 17B show coordination numbers and BVS calculations for $Ce_{38}a$ and $Ce_{38}b$ respectively. FIGS. 18A and 18B show BVS values for $Ce_{38}a$ and $Ce_{38}b$ respectively. An embodiment of a molecular cerium-oxide nanocluster having a nuclearity of 38 ($Ce_{38}$, or $Ce_{38}a$ for this particular embodiment) can be synthesized according to the embodiment of the reaction mechanism shown in FIG. 19A. An illustration of a structure of a molecular $Ce_{38}$ cluster can be seen in FIG. 19B. An illustration of a structure of a core of a molecular $Ce_{38}$ cluster can be seen in FIG. 19C. An additional embodiment of a molecular cerium-oxide nanocluster having a nuclearity of 38 ($Ce_{38}$, or $Ce_{38}b$ for this particular embodiment) can be synthesized according to the embodiment of the reaction mechanism shown in FIG. 20A. An illustration of a structure of a molecular $Ce_{40}$ cluster can be seen in FIG. 20B. An illustration of a structure of a core of a molecular $Ce_{40}$ cluster can be seen in FIG. 20C. FIG. 21 depicts the flourite structure of a molecular cerium-oxide nanocluster core of cerium nuclearity 38 ($Ce_{38}$). FIGS. 22A and 22B show coordination numbers and oxidation states for $Ce_{38}a$ and $Ce_{38}b$ respectively.

Example 7

Figure 26A:
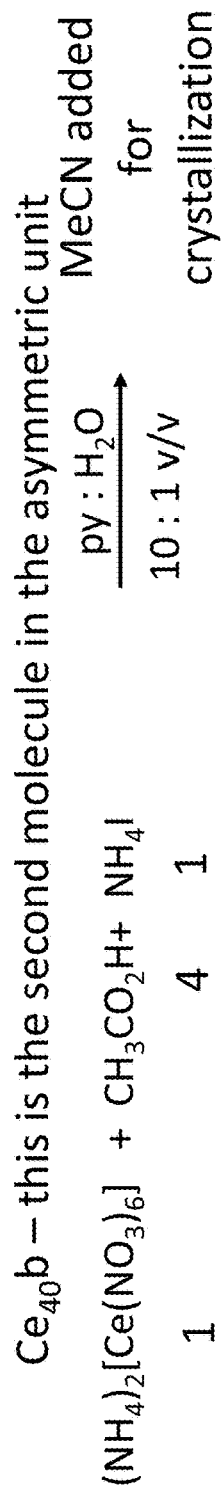
FIG. 26A illustrates a synthesis reaction for synthesizing a molecular cerium-oxide nanocluster of cerium nuclearity 40 ($Ce_{40}$).
Figure 26C:
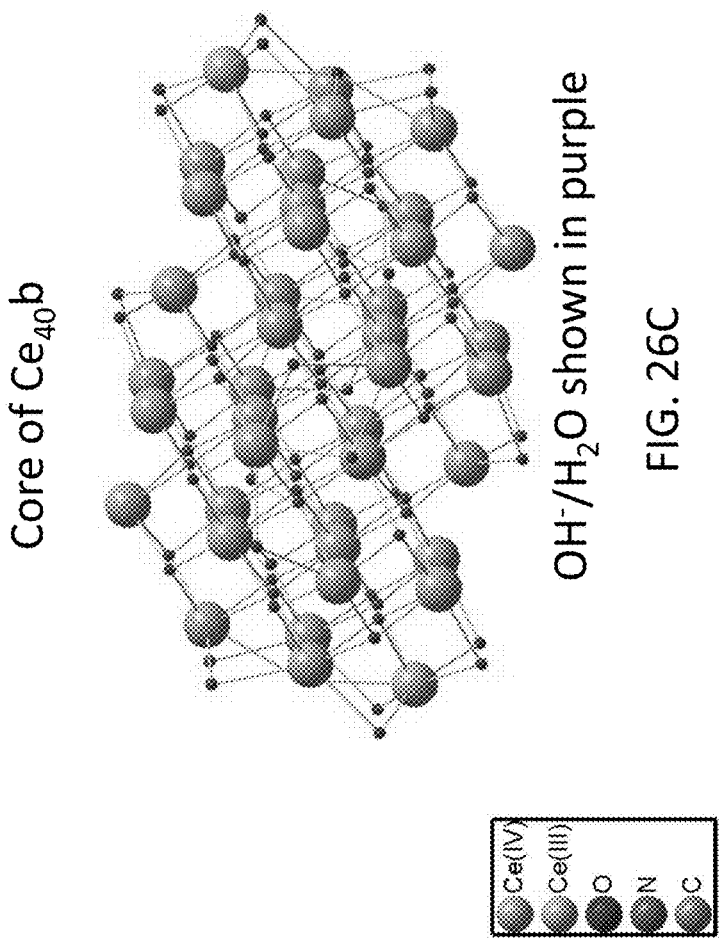
FIG. 26C shows a structure for a molecular cerium-oxide nanocluster core of cerium nuclearity 40 ($Ce_{40}$), demonstrating the flourite structure.
Figure 26B:
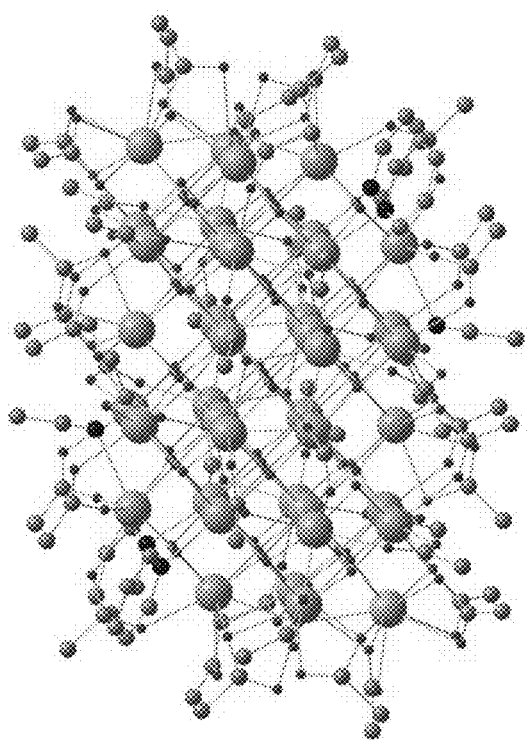
FIG. 26B depicts a structure for a molecular cerium-oxide nanocluster of cerium nuclearity 40 ($Ce_{40}$).
Figure 26B:
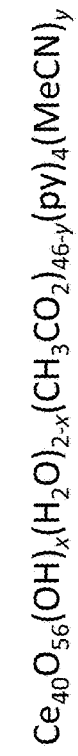
Figure 27:
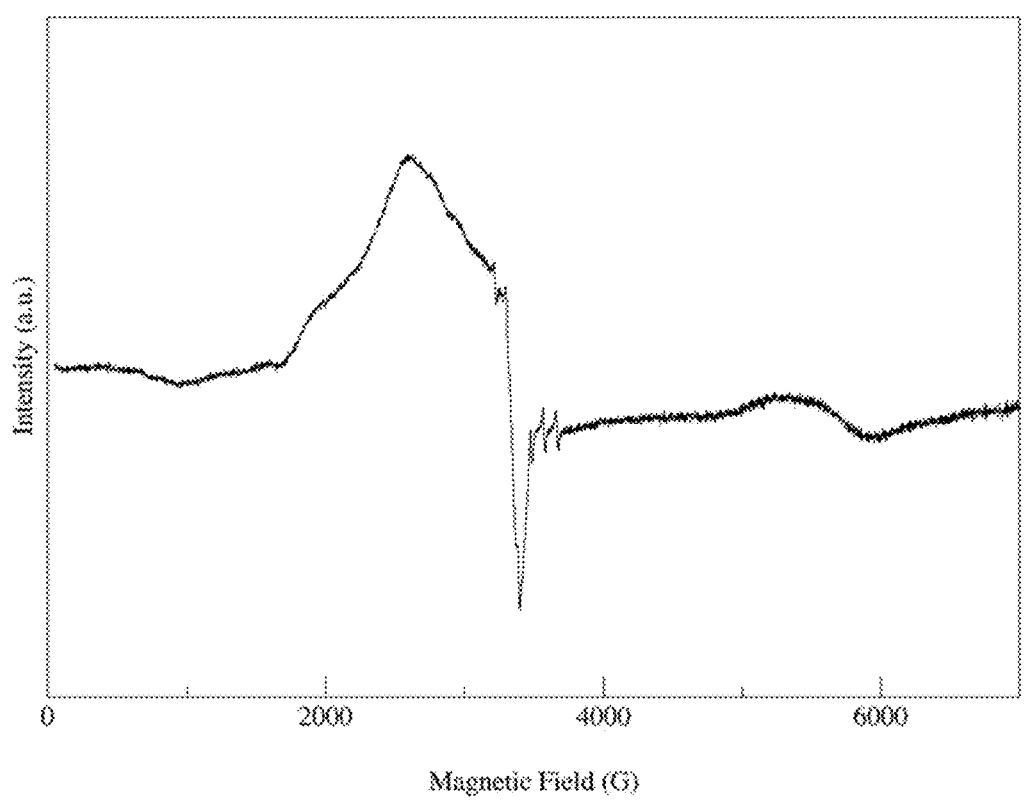
FIG. 27 is an EPR spectrum for a $Ce_{40}$ molecular cerium-oxide nanocluster.
Figure 28:
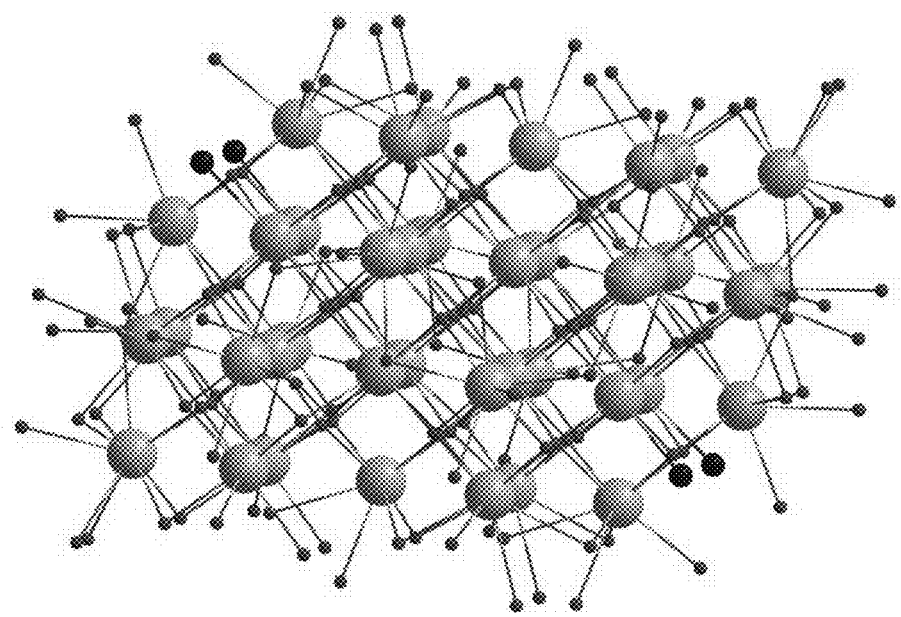
FIG. 28 depicts the flourite structure of a molecular cerium-oxide nanocluster of cerium nuclearity 40 ($Ce_{40}$).

Embodiments of molecular cerium-oxide nanoclusters of nuclearity 40 ($Ce_{40}$ a and $Ce_{40}b$) are synthesized. FIGS. 23A and 23B show coordination numbers and BVS calculations for $Ce_{40}a$ and $Ce_{40}b$ respectively. FIGS. 24A and 24B show additional BVS values for $Ce_{40}a$ and $Ce_{40}b$ respectively. An embodiment of a molecular cerium-oxide nanocluster having a nuclearity of 40 ($Ce_{40}$, or $Ce_{40}a$ for this particular embodiment) can be synthesized according to the embodiment of the reaction mechanism shown in FIG. 25A. An illustration of a structure of a molecular $Ce_{40}a$ cluster can be seen in FIG. 25B. An illustration of a structure of a core of a molecular $Ce_{40}a$ cluster can be seen in FIG. 25C. An additional embodiment of a molecular cerium-oxide nanocluster having a nuclearity of 40 ($Ce_{40}$, or $Ce_{40}b$ for this particular embodiment) can be synthesized according to the embodiment of the reaction mechanism shown in FIG. 26A. An illustration of a structure of a molecular $Ce_{40}b$ cluster can be seen in FIG. 26B. An illustration of a structure of a core of a molecular $Ce_{40}b$ cluster can be seen in FIG. 26C. FIG. 27 is an EPR spectrum for a $Ce_{40}$ molecular cerium-oxide nanocluster. FIG. 28 depicts the flourite structure of a molecular cerium-oxide nanocluster core of cerium nuclearity 40 ($Ce_{40}$). FIGS. 29A and 29B show coordination numbers and oxidation states for $Ce_{40}a$ and $Ce_{40}b$ respectively.

Example 8

An example of a general reaction and isolation method:

To a stirred solution of water/pyridine (1:10 mL v/v) was added $(NH_4)_2[Ce(NO_3)_6]$ (0.548 g, 1.00 mmol) and a carboxylic acid (2.00-4.00 mmol) followed by $NH_4I$ (0.144 g, 1.00 mmol). The golden yellow solution was stirred for 30 minutes, followed by the addition of 20 mL of MeCN to the solution. The solution was then left to sit for three days, during which time X-ray quality yellow square plates formed. The crystals were maintained in mother liquor for the X-ray crystallographic analysis, and collected by filtration, washed with acetonitrile, and dried under vacuum for other solid state studies.

Example 9

Figure 30A:
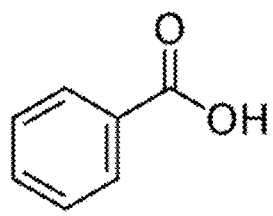
FIGS. 30A-30D shows embodiments of organic acids that can be used to synthesize cerium-oxide nanoclusters, including benzoic acid (FIG. 28A) and related derivatives 4-methylbenzoic acid (FIG. 28B), 3-methylbenzoic acid (FIG. 28C), and 2-methylbenzoic acid (FIG. 28D).
Figure 30B:
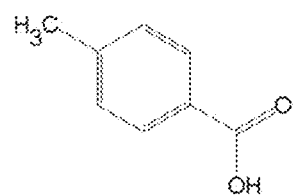
Figure 30C:
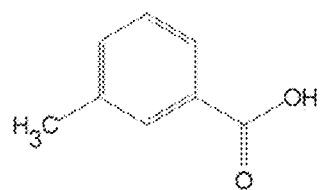
Figure 30D:
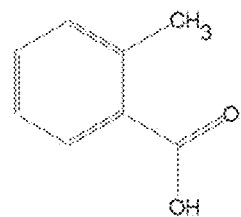

Example 9 shows embodiments of organic used that can be used to synthesize molecular cerium-oxide nanoclusters according to methods herein. FIG. 30A depicts the structure of benzoic acid, whereas FIG. 30B shows 4-methylbenzoic acid, FIG. 30C shows 3-methylbenzoic acid, and FIG. 30D shows 2-methylbenzoic acid. Without intending to be limiting, other benzoic acid derivatives can be used with substitutions on the ring such as: halogens (Cl, Br for example), nitrogen dioxide ($NO_2$), hydroxyl groups (OH), and linear, branched, saturated/unsaturated or substituted aliphatic groups.

Example 10

Figure 31A:
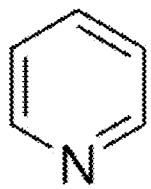
FIGS. 31A-31C show embodiments of reagents that can be used for cerium-oxide nanocluster synthesis according to methods herein. Pyridine (FIG. 29A), 4-methylpyridine (FIG. 29B), and 2,6-dimethylpyridine (FIG. 29C) are shown.
Figure 31B:
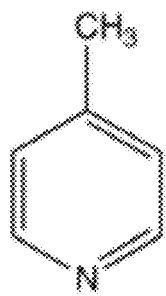
Figure 31C:
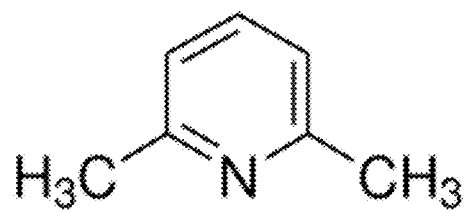
Figure 32:
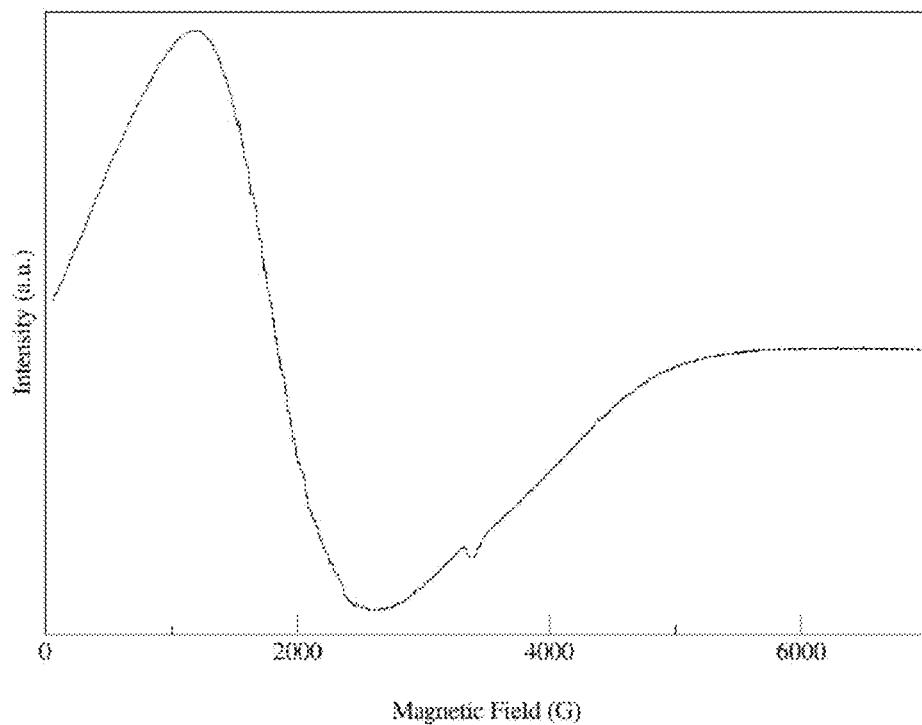
FIG. 32 shows an EPR spectrum of $Ce_{24}$ nanocluster 1 as a microcrystalline powder at 5.0 K in the 0 to 7000 G field range. The signal around 3500 G is from a Cu impurity present in the resonator.
Figure 33:
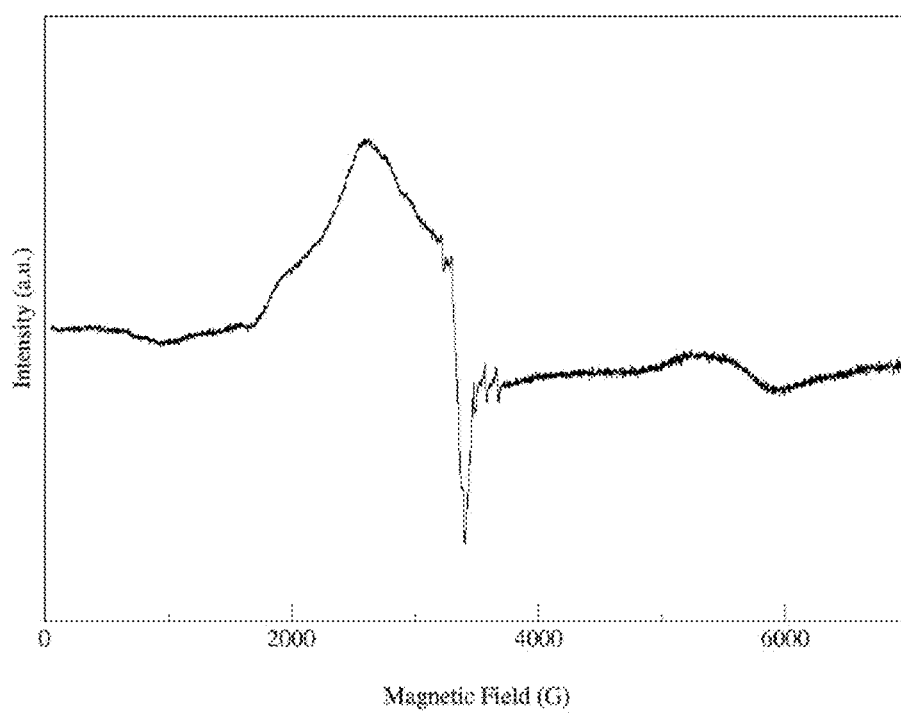
FIG. 33 shows EPR spectrum of $Ce_{40}$ nanocluster 3 as a microcrystalline powder at 5.0 K in the 0 to 7000 G field range. The large signal around 3500 G is from a Cu impurity present in the resonator.
Figure 34:
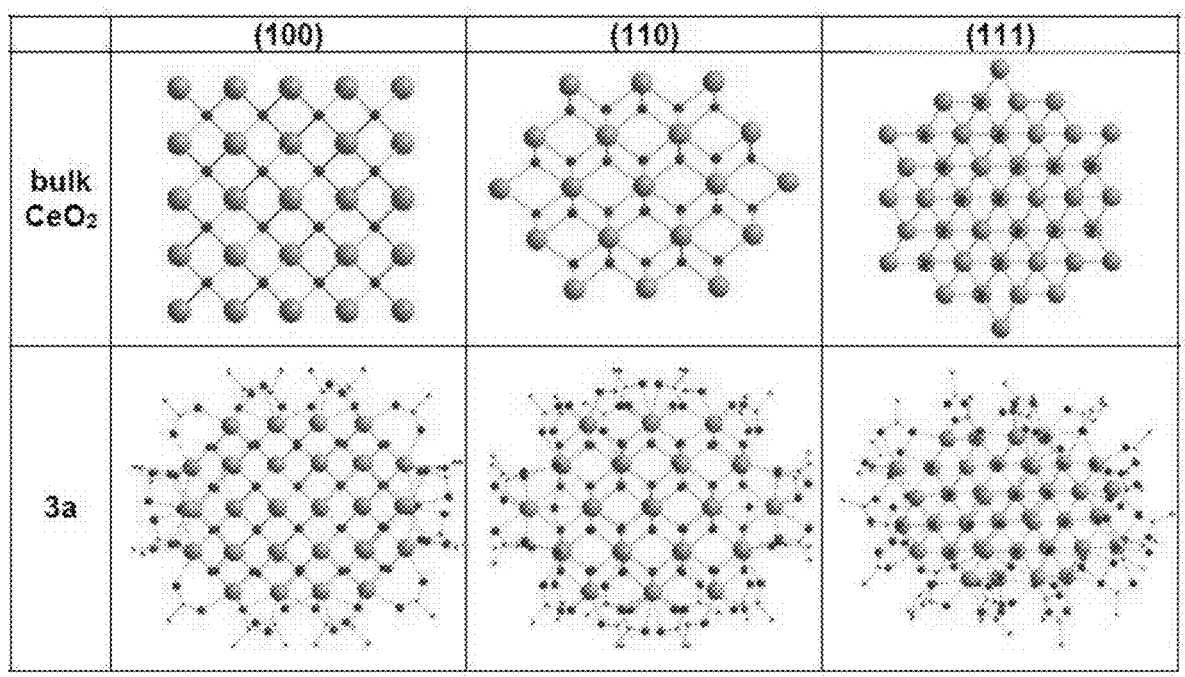
FIG. 34 illustrates a comparison of the core faces of $Ce_{40}$ nanocluster 3a with those of bulk $CeO_2$. Three views of 3a showing the correspondence with the (100), (110), and (111) faces of $CeO_2$. Colour code: $Ce^{4+}$ gold, $Ce^{3+}$ sky-blue, O red, C grey.
Figure 35A:
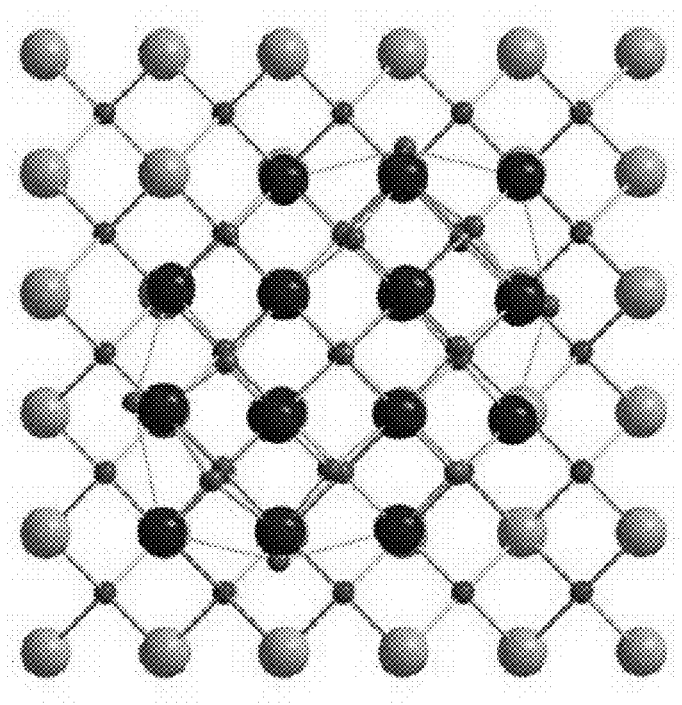
FIGS. 35A-35C show overlays of the Ce/O cores of 1 (FIG. 35A), 2 (FIG. 35B), and 3 (FIG. 35C; Ce blue, O green) on the $CeO_2$ structure (Ce gold, O red) showing only a small deviation of the nanocluster core atoms from their positions in bulk $CeO_2$.
Figure 35B:
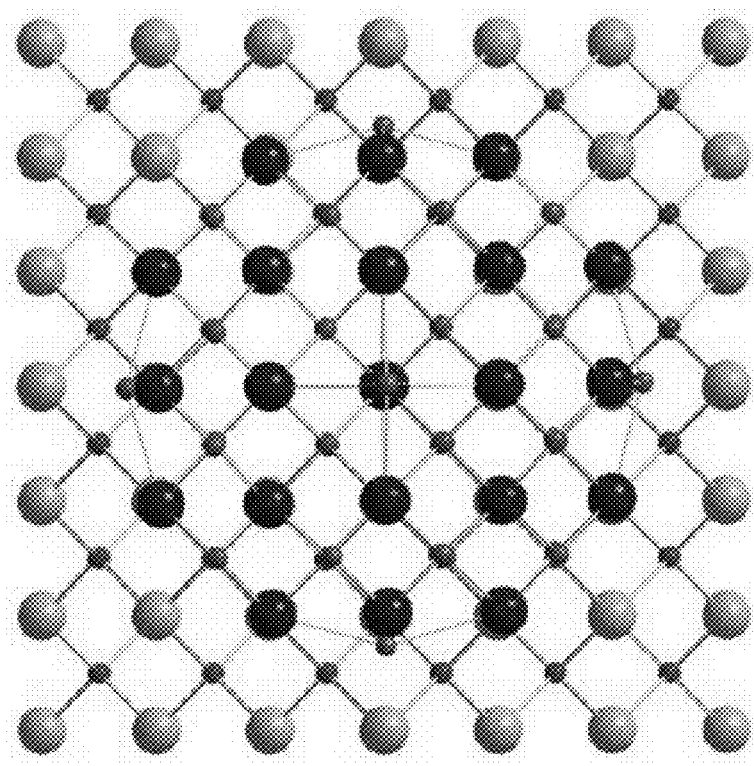
Figure 35C:
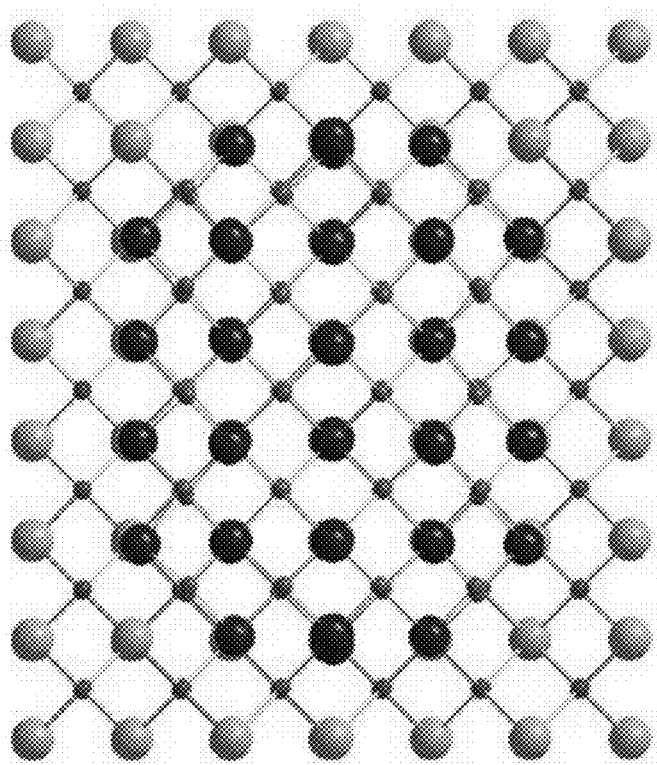
Figure 36A:
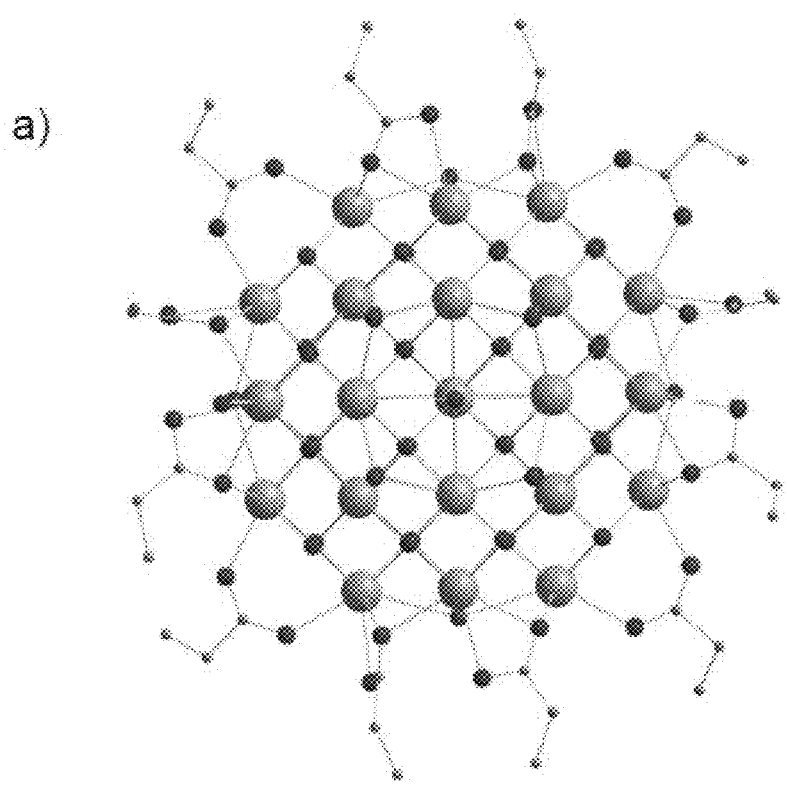
FIG. 36A-36B are slices from the structures of a) $Ce_{38}$ 2 and b) $Ce_{40}$ 3a (FIGS. 36A and 36B, respectively), chosen to emphasize how the versatile and flexible binding modes of carboxylates allow them to accommodate points of high surface curvature, as well as binding to either Ce2 or Ce3 units with differing metal separations.
Figure 36B:
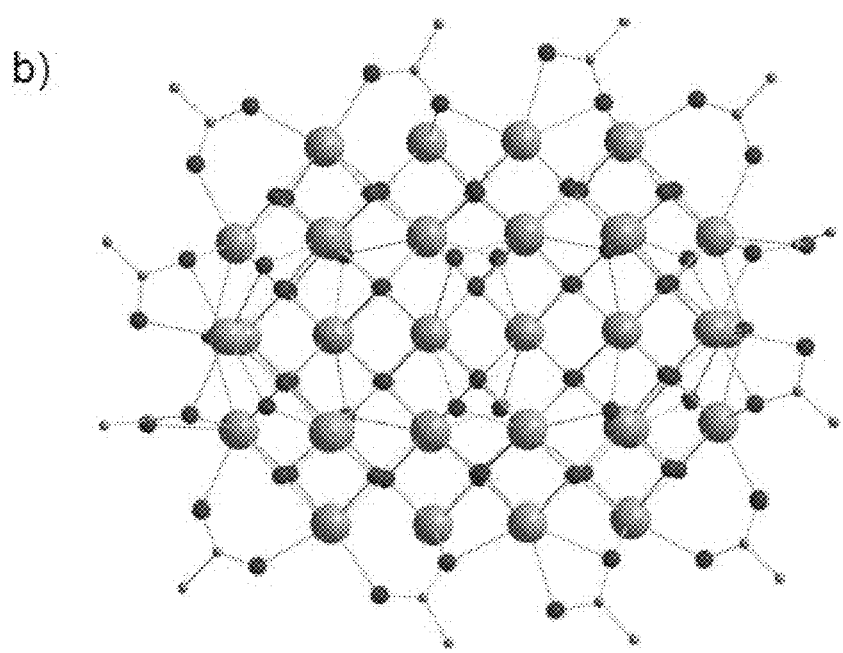
Figure 37A:
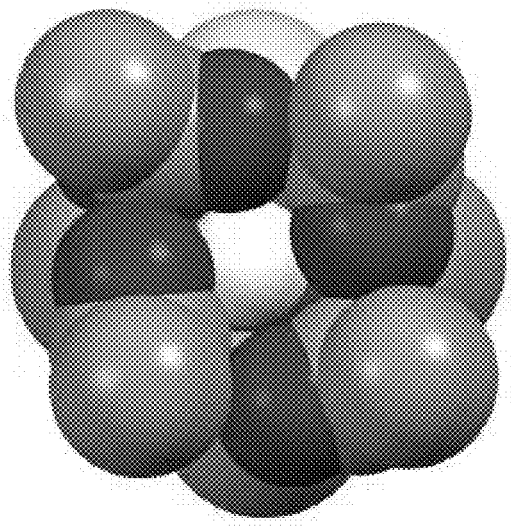
FIG. 37A-FIG. 37B are space-filling representations of (a) the $\{Ce_3+Ce_{4+3}(\mu_4\text{-OH})\}$ unit of $Ce_{24}$ nanocluster 1 (FIG. 37A), and (b) one $\{Ce_{4+4}(\mu_4\text{-OH})\}$ unit of $Ce_{38}$ nanocluster 2 (FIG. 37B). Both are viewed approximately perpendicular to the $Ce_4$ planes, emphasizing the $\mu_4$-OH— at the centre and the surrounding carboxylate ligands; for clarity in 1, only the carboxylate and ipso C atoms of the benzoate phenyl rings are shown. Colour code: $Ce_{4+}$ gold, $Ce_{3+}$ sky-blue, $\mu_4$-O violet, other O red, C grey, H white.
Figure 37B:
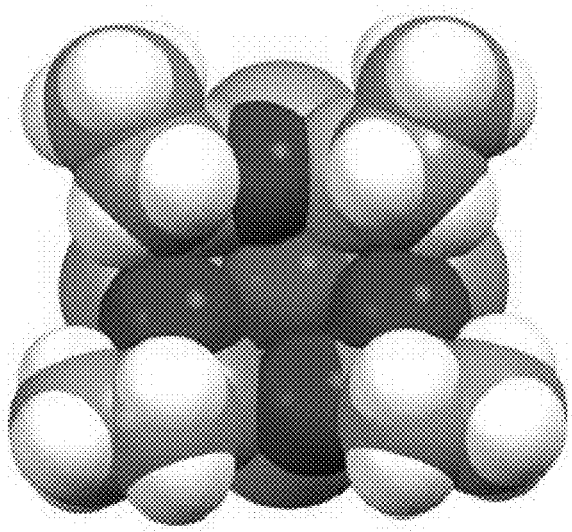

As shown in previous examples, pyridine (FIG. 31A) can be used in molecular cerium-oxide nanocluster synthesis, but other pyridine derivatives, such as 4-methylpyridine (FIG. 31B) and 2,6-dimethylpyridine (FIG. 31C) can be used as well. Additional substitutions can be made on the carbon ring of pyridine as well.

Example 11

All the syntheses below have been reproduced many times, giving yields in a range within a few percent of the quoted yield. The $NH_4I$ was added to provide a weak reducing agent to readily allow formation of $Ce^{3+}$, should the reaction product so desire. The yields may benefit from further optimization: at this stage, reaction conditions as described herein are targeted at well-formed crystalline solids from slow crystallizations to allow definitive characterization by single-crystal X-ray crystallography, rather than faster precipitation of products as powders.

$[Ce_{24}O_{28}(OH)_8(PhCO_2)_{30}(py)_4]$ (1; also referred to as $Ce_{24}$). To a stirred solution of pyridine (10 mL) was added $(NH_4)_2[Ce(NO_3)_6]$ (0.55 g, 1.0 mmol) and $PhCO_2H$ (0.25 g, 2.0 mmol). The golden yellow solution was stirred for 30 minutes, followed by the addition of 20 mL of MeCN. The solution was then left to sit for one week, during which time X-ray quality yellow square plates of 1·9py formed. They were collected by filtration, washed with MeCN, and dried in vacuum. The yield was 14% based on Ce. Anal. Calcd (Found) for dried 1·2py ($C_{240}H_{188}Ce_{24}N_6O_{96}$): C, 35.79 (35.63); H, 2.35 (2.00); N, 1.04 (0.98). Selected IR data (cm−1): 3435 (b), 3059 (w), 1594 (m), 1534 (s), 1492 (w), 1447 (w), 1402 (s), 1307 (w), 1178 (m), 1069 (m), 1025 (m), 849 (w), 717 (s), 688 (w), 672 (w), 565 (m), 506 (m), 431 (s).

$[Ce_{38}O_{54}(OH)_8(EtCO_2)_{36}(py)_8]$ (2; also referred to as $Ce_{38}$). To a stirred solution of aqueous pyridine (11 mL, 10:1 v/v) was added $(NH_4)_2[Ce(NO_3)_6]$ (0.55 g, 1.0 mmol) and propionic acid (0.30 mL, 4.0 mmol) followed by $NH_4I$ (0.15 g, 1.0 mmol). The golden yellow solution was stirred for 30 minutes, followed by the addition of 20 mL of MeCN. The solution was then left to sit for four weeks, during which time X-ray quality yellow square plates of 2·16MeCN formed. They were collected by filtration, washed with MeCN, and dried in vacuum. The yield was 49% based on Ce. Anal. Calcd (Found) for 2·7H$_2$O ($C_{148}H_{242}Ce_{38}N_8O_{141}$): C, 18.30 (17.90); H, 2.51 (2.36); N, 1.15 (1.05). Selected IR data (cm−1): 3570 (w), 3432 (b), 3175 (b), 2975 (m), 2940 (m), 2879 (w), 1575 (w), 1537 (s), 1465 (m), 1415 (s), 1371 (m), 1295 (m), 1277 (m), 1078 (m), 1056 (w), 1005 (w), 891 (m), 814 (m), 698 (w), 567 (w), 492 (s). Although 2 contains no $Ce^{3+}$, the $NH_4I$ was essential to yield pure product.

$[Ce_{40}O_{56}(OH)_2(MeCO_2)_{44}(MeCO_2H)_{2/0}(MeCN)_{0/2}(py)_4]$ (3; also referred to as $Ce_{40}$). To a stirred solution of aqueous pyridine (11 mL, 10:1 v/v) was added $(NH_4)_2[Ce(NO_3)_6]$ (0.55 g, 1.0 mmol) and acetic acid (0.23 mL, 4.0 mmol) followed by $NH_4I$ (0.15 g, 1.0 mmol). The golden yellow solution was stirred for 30 minutes, followed by the addition of 20 mL of MeCN. The solution was then left to sit for four weeks, during which time X-ray quality yellow square rods of 3·48MeCN formed. They were collected by filtration, washed with MeCN, and dried in vacuum. The yield was 35% based on Ce. Anal. Calcd (Found) for 3·8H$_2$O ($C_{112}H_{177}Ce_{40}N_5O_{156}$): C, 13.88 (13.79); H, 1.84 (1.78); N, 0.72 (0.76). The indicated atomic composition of 3 is calculated using the average of the 3a and 3b formulas. Selected IR data (cm−1): 3408 (b), 3171 (b), 1540 (s), 1400 (s), 1385 (s), 1335 (m), 1050 (w), 1019 (w), 940 (w), 671 (w), 613 (w), 513 (s), 434 (m).

Single-Crystal X-Ray Crystallography

Crystallographic information files have been deposited at the Cambridge Crystallographic Data Centre with deposition codes CCDC 1529955-1529957 for 1-3, respectively. Crystal structure data for 1·9py: X-Ray Intensity data for 1 were collected on a Bruker DUO diffractometer using CuKα radiation (λ=1.54178 Å), from an ImuS power source, and an APEXII CCD area detector. The asymmetric unit comprises a half $Ce_{24}$ cluster and four and a half pyridine solvent molecules. Two of the pyridines are hydrogen-bonded to the cluster (one of them is refined with 50% occupancy) but the other three were significantly disordered and could not be modeled properly. Thus program SQUEEZE[1] a part of the PLATON[2] package of crystallographic software, was used to calculate the solvent disorder area and remove its contribution to the overall intensity data. Four of the O atoms (of the asymmetric half cluster) were protonated and their H atoms were located from a difference Fourier map. Two of them, H12 and H15 were refined riding on their parent atoms while the other two, H14 and H16, were refined freely. There are six disordered phenyl rings and each one was refined in two parts and constrained to maintain an ideal hexagonal geometry. Carbon atoms on one disordered phenyl ring, on C51', had their displacement parameters kept equivalent using command equivalent anisotropic displacement parameters (EADP) in the SHELX refinement. Similarly, the disordered pyridine solvent was refined in two positions with 60/40% occupancy and idealized geometry as well as constrained displacement parameters using the EADP command.

Crystal structure data for 2·16MeCN: X-Ray Intensity data for 2 were collected on a Bruker DUO diffractometer using MoKα radiation (λ=0.71073 Å) and an APEXII CCD area detector. The asymmetric unit comprises two ¼ $Ce_{38}$ clusters and eight MeCN solvent molecules. The solvent molecules were disordered and could not be modeled properly, thus program SQUEEZE,[1] a part of the PLATON[2] package of crystallographic software, was used to calculate the solvent disorder area and remove its contribution to the overall intensity data. Each of the clusters is located on independent 2/m symmetry sites. At the intersection of each cluster, and specifically at the side with four Ce centers forming a square, there are four propionate ligands disordered over eight positions. Similar disordered regions are found in regions 90° from the previous disorders. Application of similar distances, Sequence Analysis Distance measures (SADI), was implemented in three ligands and EADP to two sets of bonded atoms.

Crystal structure data for 3·48MeCN: X-Ray Intensity data for 3 were collected on a Bruker DUO diffractometer using MoKα radiation (λ=0.71073 Å) and an APEXII CCD area detector. The asymmetric unit comprises two 4 $Ce^{40}$ clusters and twelve acetonitrile solvent molecules. The solvent molecules were disordered and could not be modeled properly, thus program SQUEEZE,[1] a part of the PLATON[2] package of crystallographic software, was used to calculate the solvent disorder area and remove its contribution to the overall intensity data. Each of the clusters is located on independent 2/m symmetry sites. At the intersection of each cluster, and specifically at the side with four Ce centers forming a square, there are four acetate ligands disordered over eight positions. Similar disordered regions are found in regions 90° from the previous disorders. A major difference between the two independent clusters is that one has two bound MeCN ligands replacing two acetic acid ligands. Application of similar distances, SADI, was implemented in five ligands.

Supplementary Note 1

When studying/analyzing large clusters containing heavy atoms such as cerium, the intensity of reflections is usually dominated by the heavy metal atoms. Thus information about light atoms is usually of lower quality than those of the core of the metal cluster. A higher effect is also observed in the positions of disordered light atom solvents. In all of these structures, larger-than-usual observed residual positive electron density is always observed at the end of the full refinement. Data truncation can also be a major contributor to observing larger residual positive electron density. Supplementary tables 1-8 below contain data with additional characterization of structures and methods relating to structures 1 ($Ce_{24}$), 2 ($Ce_{38}$), and 3 ($Ce_{40}$) as described above.

SUPPLEMENTARY TABLE 1

| Crystal Data and Structure Refinement Parameters for 1, 2, and 3. | | | |
|---|---|---|---|
| | 1 · 9py | 2 · 16MeCN | 3 · 48MeCN |
| formula[a] | $C_{230}H_{178}Ce_{24}N_4O_{96}$ | $C_{148}H_{228}Ce_{38}N_8O_{134}$ | $C_{112}H_{161}Ce_{40}N_5O_{148}$[b] |
| Fw · g mol$^{-1}$ | 7896.77 | 9587.92 | 9550.20 |
| space group | P2$_1$/n | C2/m | P2/m |
| a, Å | 21.2942(6) | 29.205(2) | 17.4795(7) |
| b, Å | 25.0588(7) | 28.175(2) | 21.0019(9) |
| c, Å | 25.4417(7) | 29.809(2) | 38.6269(16) |
| α, deg | 90 | 90 | 90 |
| β, deg | 91.9276(14) | 92.2675(15) | 98.254(1) |
| γ, deg | 90 | 90 | 90 |
| V, Å$^3$ | 13568.2(7) | 24509(3) | 14033.2(10) |
| Z | 2 | 4 | 1 |
| T, K | 100(2) | 108(2) | 100(2) |
| λ, Å[c] | 1.54178 Å | 0.71073 | 0.71073 |
| $\rho_{calc}$, g cm$^{-3}$ | 2.030 | 2.596 | 2.492 |
| μ, mm$^{-1}$ | 31.111 | 6.988 | 6.433 |
| R1[d,e] | 0.0554 | 0.0768 | 0.0626 |
| wR2[f] | 0.1580 | 0.1956 | 0.1884 |

[a]Excluding solvent molecules of crystallization.
[b]Average of the formulas of 3a and 3b.
[c]Graphite monochromator.
[d]I > 2σ(I).
[e]R1 = 100Σ(||F$_o$| − |F$_c$||)/Σ|F$_o$|.
[f]wR2 = 100[Σ[w(F$_o^2$ − F$_c^2$)$^2$]/Σ[w(F$_o^2$)$^2$]]$^{1/2}$, w = 1/Σ$^2$(F$_o^2$) + [(ap)$^2$ + bp], where p = [max(F$_o^2$, 0) + 2F$_c^2$]/3.

SUPPLEMENTARY TABLE 2

Bond Valence Sums and Coordination Numbers (CN) for Ce Atoms in 1, 2, and 3.[a,b]

| | 1 | | | | 2a[c] | | | | 3a | | | | 2b[c] | | | | 3b | | |
|---|---|---|---|---|---|---|---|---|---|---|---|---|---|---|---|---|---|---|---|
| Atom | CN | $CE^{III}$ | $Ce^{IV}$ | Atom | CN | $CE^{III}$ | $Ce^{IV}$ | Atom | CN | $CE^{III}$ | $Ce^{IV}$ | Atom | CN | $CE^{III}$ | $Ce^{IV}$ | Atom | CN | $CE^{III}$ | $Ce^{IV}$ |
| Ce1 | 9 | 4.33 | 3.81 | Ce1 | 9 | 4.29 | 3.76 | Ce1 | 9 | 4.39 | 3.86 | Ce21 | 9 | 4.19 | 3.68 | Ce21 | 8 | 4.41 | 3.87 |
| Ce2 | 9 | 4.28 | 3.76 | Ce2 | 8 | 4.45 | 3.91 | Ce2 | 8 | 4.37 | 3.84 | Ce22 | 9 | 4.45 | 3.91 | Ce22 | 7 | 4.24 | 3.73 |
| Ce3 | 9 | 4.46 | 3.92 | Ce3 | 9 | 4.39 | 3.86 | Ce3 | 9 | 4.39 | 3.85 | Ce23 | 9 | 4.35 | 3.82 | Ce23 | 9 | 4.34 | 3.81 |
| Ce4 | 10 | 3.01 | 2.65 | Ce4 | 8 | 4.61 | 4.06 | Ce4 | 8 | 4.46 | 3.92 | Ce24 | 9 | 4.18 | 3.67 | Ce24 | 8 | 4.06 | 3.56 |
| Ce5 | 8 | 4.28 | 3.76 | Ce5 | 8 | 4.62 | 4.06 | Ce5 | 8 | 4.63 | 4.07 | Ce25 | 8 | 4.50 | 3.95 | Ce25 | 8 | 4.66 | 4.09 |
| Ce6 | 8 | 4.54 | 3.99 | Ce6 | 9 | 4.36 | 3.83 | Ce6 | 9 | 4.43 | 3.89 | Ce26 | 8 | 4.64 | 4.07 | Ce26 | 8 | 4.31 | 3.78 |
| Ce7 | 9 | 4.29 | 3.77 | Ce7 | 9 | 4.39 | 3.85 | Ce7 | 8 | 4.31 | 3.79 | Ce27 | 9 | 4.51 | 3.96 | Ce27 | 8 | 4.14 | 3.64 |
| Ce8 | 8 | 4.46 | 3.91 | Ce8 | 9 | 4.27 | 3.75 | Ce8 | 9 | 4.33 | 3.81 | Ce28 | 8 | 4.50 | 3.95 | Ce28 | 8 | 4.23 | 3.71 |
| Ce9 | 9 | 4.30 | 3.77 | Ce9 | 9 | 4.33 | 3.80 | Ce9 | 9 | 4.58 | 4.02 | Ce29 | 8 | 4.55 | 4.00 | Ce29 | 8 | 4.47 | 3.93 |
| Ce10 | 8 | 4.37 | 3.84 | Ce10 | 8 | 4.43 | 3.89 | Ce10 | 8 | 4.25 | 3.74 | Ce30 | 9 | 4.52 | 3.97 | Ce30 | 9 | 4.39 | 3.86 |
| Ce11 | 8 | 4.24 | 3.72 | Ce11 | 9 | 4.71 | 4.13 | Ce11 | 8 | 4.21 | 3.70 | Ce31 | 9 | 4.54 | 3.98 | Ce31 | 10 | 3.20 | 2.81 |
| | | | | | | | | Ce12 | 7 | 4.36 | 3.83 | Ce32 | 9 | 4.84 | 4.25 | Ce32 | 8 | 4.46 | 3.91 |
| | | | | | | | | Ce13 | 10 | 2.81 | 2.47 | Ce33 | 9 | 4.87 | 4.27 | Ce33 | 9 | 4.49 | 3.95 |

[a] The bold values are the ones closest to the charge for which they were calculated; the oxidation state is thus the nearest integer to the bold value.
[b] CN = coordination number.
[c] The formulas of 2a and 2b are identical.

SUPPLEMENTARY TABLE 3

Bond Valence Sums and Assignments for the O Atoms[a] in 1.

| 1 Atom | BVS | Assignment |
|---|---|---|
| O1 | 1.89 | $O^{2-}$ |
| O2 | 1.94 | $O^{2-}$ |
| O3 | 1.88 | $O^{2-}$ |
| O4 | 2.09 | $O^{2-}$ |
| O5 | 2.15 | $O^{2-}$ |
| O6 | 1.94 | $O^{2-}$ |
| O7 | 2.17 | $O^{2-}$ |
| O8 | 1.81 | $O^{2-}$ |
| O9 | 2.08 | $O^{2-}$ |
| O10 | 2.09 | $O^{2-}$ |
| O11 | 2.11 | $O^{2-}$ |
| O12 | 0.71 | $\mu_4\text{-OH}^{-b,c}$ |
| O13 | 1.94 | $O^{2-}$ |
| O14 | 0.69 | $\mu_4\text{-OH}^{-b,c}$ |
| O15 | 1.21 | $\mu_3\text{-OH}^{-b}$ |
| O16 | 1.21 | $\mu_3\text{-OH}^{-b}$ |
| O17 | 1.94 | $O^{2-}$ |
| O19 | 1.71 | $O^{2-}$ |

[a] An oxygen BVS in the ~1.8-2.0, ~0.9-1.2 and ~0.2-0.4 ranges is indicative of non-, single- and double- protonation, respectively.
[b] Two by symmetry.
[c] Square pyramidal O geometry.

SUPPLEMENTARY TABLE 4

Bond Valence Sums and Assignments for the non-Carboxylate O Atoms[a] in 2.

| 2a Atom | BVS | Assignment | 2b Atom | BVS | Assignment |
|---|---|---|---|---|---|
| O1 | 1.93 | $O^{2-}$ | O42 | 0.52 | $\mu_4\text{-OH}^{-b,d}$ |
| O3 | 1.86 | $O^{2-}$ | O45 | 2.12 | $O^{2-}$ |
| O4 | 2.14 | $O^{2-}$ | O49 | 1.65 | $O^{2-c,e}$ |
| O7 | 0.57 | $\mu_4\text{-OH}^{-b,d}$ | O50 | 2.12 | $O^{2-}$ |
| O9 | 2.13 | $O^{2-}$ | O54 | 2.11 | $O^{2-}$ |
| O10 | 2.11 | $O^{2-}$ | O59 | 1.86 | $O^{2-}$ |
| O11 | 2.00 | $O^{2-}$ | O60 | 1.72 | $O^{2-c,e}$ |
| O12 | 2.04 | $O^{2-}$ | O63 | 2.03 | $O^{2-}$ |
| O13 | 2.11 | $O^{2-}$ | O64 | 0.57 | $\mu_4\text{-OH}^{-b,d}$ |
| O14 | 1.96 | $O^{2-}$ | O69 | 1.91 | $O^{2-}$ |
| O15 | 2.11 | $O^{2-}$ | O70 | 2.15 | $O^{2-}$ |
| O16 | 1.90 | $O^{2-}$ | O71 | 2.10 | $O^{2-}$ |
| O17 | 2.12 | $O^{2-}$ | O72 | 1.99 | $O^{2-}$ |
| O18 | 1.71 | $O^{2-b,e}$ | O73 | 2.12 | $O^{2-}$ |
| O27 | 0.57 | $\mu_4\text{-OH}^{-c,d}$ | O74 | 1.96 | $O^{2-}$ |
| O28 | 2.10 | $O^{2-}$ | O75 | 0.58 | $\mu_4\text{-OH}^{-b,d}$ |
| O29 | 1.86 | $O^{2-}$ | O79 | 1.89 | $O^{2-}$ |
| O30 | 1.91 | $O^{2-}$ | | | |
| O39 | 1.52 | $O^{2-b,e}$ | | | |

[a] An oxygen BVS in the ~1.8-2.0, ~0.9-1.2 and ~0.2-0.4 ranges is indicative of non-, single- and double- protonation, respectively.
[b] Two by symmetry.
[c] Four by symmetry.
[d] Square pyramidal O geometry.
[e] Possible partial occupancy by $OH^-$.

SUPPLEMENTARY TABLE 5

Bond Valence Sums and Assignments for the O Atoms[a] in 3.

| 3a Atom | BVS | Assignment | 3b Atom | BVS | Assignment |
|---|---|---|---|---|---|
| O1 | 2.14 | $O^{2-}$ | O41 | 1.95 | $O^{2-}$ |
| O2 | 2.09 | $O^{2-}$ | O42 | 2.09 | $O^{2-}$ |
| O4 | 0.64 | $\mu_4\text{-OH}^{-b}$ | O43 | 2.07 | $O^{2-}$ |
| O5 | 2.00 | $O^{2-}$ | O44 | 2.00 | $O^{2-}$ |
| O6 | 1.98 | $O^{2-}$ | O45 | 2.00 | $O^{2-}$ |
| O7 | 1.88 | $O^{2-}$ | O46 | 2.00 | $O^{2-}$ |
| O8 | 2.06 | $O^{2-}$ | O47 | 2.07 | $O^{2-}$ |
| O9 | 2.10 | $O^{2-}$ | O48 | 2.18 | $O^{2-}$ |
| O10 | 2.06 | $O^{2-}$ | O49 | 1.90 | $O^{2-}$ |
| O11 | 2.01 | $O^{2-}$ | O50 | 1.97 | $O^{2-}$ |
| O12 | 1.88 | $O^{2-}$ | O51 | 1.85 | $O^{2-}$ |
| O13 | 1.99 | $O^{2-}$ | O52 | 1.86 | $O^{2-}$ |
| O14 | 1.94 | $O^{2-}$ | O53 | 1.95 | $O^{2-}$ |
| O15 | 1.94 | $O^{2-}$ | O54 | 2.14 | $O^{2-}$ |
| O16 | 1.99 | $O^{2-}$ | O55 | 1.98 | $O^{2-}$ |
| O17 | 2.06 | $O^{2-}$ | O57 | 0.64 | $\mu_4\text{-OH}^{-b}$ |
| O40 | 1.78 | $RO^{-c}$ | | | |
| O40' | 1.78 | $RO^{-c}$ | | | |
| O83 | 1.65 | $RO^{-c}$ | | | |

[a] An oxygen BVS in the ~1.8-2.0, ~0.9-1.2 and ~0.2-0.4 ranges is indicative of non-, single- and double- protonation, respectively.
[b] Square pyramidal O geometry.
[c] Carboxylate O atoms forming a triangle that is proposed to be capped by a $H^+$ giving lowered BVS values for the O atoms akin to partial occupancy by ROH (i.e., $MeCO_2H$). A prime indicates the symmetry-related atom.

Supplementary Table 6.
Bond distances for $\mu_3$-OH$^-$ in a triangle of Ce$^{4+}$ ions.

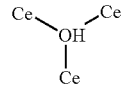

| | Parameter | Distance (Å) |
|---|---|---|
| 1 | Ce2-O15 | 2.364 (5) |
| | Ce7-O15 | 2.411 (5) |
| | Ce10-O15 | 2.450 (5) |
| | Ce3-O16 | 2.367 (5) |
| | Ce8-O16 | 2.429 (5) |
| | Ce9-O16 | 2.420 (5) |
| 2a | Ce7-O39 | 2.295 (15) |
| | Ce11-O39 | 2.34 (7) |
| | Ce11'-O39 | 2.34 (7) |

Supplementary Table 7.
Ce—O separations in $\mu_4$-OH$^-$ bridged Ce$^{3+}$/3Ce$^{4+}$ and 4Ce$^{4+}$ squares

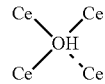

| | Parameter | Distance (Å) |
|---|---|---|
| 1 | Ce1-O12 | 2.843 (6) |
| | Ce2-O12 | 2.674 (5) |
| | Ce3-O12 | 2.669 (5) |
| | Ce4-O12 | 2.724 (6) |
| | Ce4-O14 | 2.990 (6) |
| | Ce7-O14 | 2.600 (5) |
| | Ce9-O14 | 2.681 (5) |
| | Ce12-O14 | 2.721 (6) |
| 3a | Ce1-O4 | 2.739 (13) |
| | Ce8-O4 | 2.766 (4) |
| | Ce8'-O4 | 2.766 (4) |
| | Ce13-O4 | 2.766 (13) |
| 3b | Ce30-O57 | 2.755 (3) |
| | Ce30'-O57 | 2.755 (3) |
| | Ce31-O57 | 2.751 (14) |
| | Ce33-O57 | 2.736 (14) |

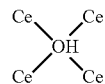

| | Parameter | Distance (Å) |
|---|---|---|
| 2$^a$ | Ce1-O7 | 2.808 (13) |
| | Ce1'-O7 | 2.808 (13) |
| | Ce8-O7 | 2.772 (13) |
| | Ce8'-O7 | 2.772 (13) |
| | Ce3-O27 | 2.816 (13) |
| | Ce6-O27 | 2.743 (12) |
| | Ce9-O27 | 2.861 (12) |
| | Ce11-O27 | 2.750 (12) |
| 2b | Ce23-O64 | 2.790 (17) |
| | Ce27-O64 | 2.790 (5) |
| | Ce32-O64 | 2.795 (17) |
| | Ce27-O64 | 2.790 (5) |
| | Ce30-O75 | 2.796 (3) |
| | Ce31-O75 | 2.711 (16) |

Supplementary Table 8.
Ce—O/N separations in RCO$_2^-$— and MeCN-bridged Ce$^{3+}$/3Ce$^{4+}$ and 4Ce$^{4+}$ squares

| | Parameter | Distance (Å) |
|---|---|---|
| 3a | Ce9-O32 | 2.715 (13) |
| | Ce10-O32 | 2.996 (41) |
| | Ce10-O32 | 2.996 (41) |
| | Ce11-O32 | 3.054 (11) |
| | Ce11-O38 | 2.628 (13) |
| | Ce12-O38 | 3.004 (43) |
| | Ce12-O38 | 3.004 (43) |
| | Ce13-O38 | 3.388 (12) |

| | Parameter | Distance (Å) |
|---|---|---|
| 3b | Ce32-N3 | 2.69 (3) |
| | Ce27-N3 | 3.098 (13) |
| | Ce27-N3 | 3.098 (13) |
| | Ce24-N3 | 3.269 (28) |
| | Ce24-O74 | 2.535 (16) |
| | Ce22-O74 | 3.045 (72) |
| | Ce22-O74 | 3.045 (72) |
| | Ce31-O74 | 3.483 (15) |

SUPPLEMENTARY REFERENCES 1. van der Sluis, P. & Spek, A. L. SQUEEZE. *Acta Cryst*, A46, 194-201(1990).
2. Spek. A. L. PLATON, *Acta Cryst*. D65 148-155 (2009).

Example 12

Introduction

Cerium-dioxide nanoparticles (CNPs, nanoceria) are widely used in catalysis, mechanical polishing, solid-oxide fuel cells, UV-shielding, and other applications.[1-7] CNPs are useful and reactive materials due to the general advantage of nanoparticles in that they possess a high surface area to volume ratio, but also because of the increased amount of Ce$^{3+}$ present on the surface, relative to the bulk material, and the ease at which Ce can switch between the trivalent and tetravalent oxidation state. CeO$_2$ possesses the fluorite structure where each Ce ion is surrounded by eight tetrahedral oxides. This fluorite lattice allows for the creation of oxygen vacancies with the reduction of Ce$^{4+}$ to Ce$^{3+}$, contributing to the overall reactivity of these nanoparticles. More recently, CNPs have gained increased attention due to their increased reactivity at lower temperatures and even room temperature, especially in the area of nanomedicine.[7-18] This is largely due to CNPs scavenging ability of reactive oxygen species (ROS). Under conditions of oxidative stress, an imbalance is created in which over-abundant ROS overwhelm cellular defenses—typically regulated and protected by antioxidants—and thus damage biological cells. There are many pathological conditions in which oxidative stress plays an important role such as cancer, stroke, Alzheimer's, inflammation, or neurodegeneration. Therefore, significant efforts are being made to identify materials to safely scavenge ROS.[19-23]

CNPs have been shown to scavenge a variety of radical species though their multi-enzyme mimetic ability. Due to the ability of cerium to easily switch between the $Ce^{3+}$ and $Ce^{4+}$ oxidation state, these nanoparticles have been shown to be regenerative and to serve a dual role as oxidation or reduction catalysts depending on the reaction conditions— $Ce^{4+}$ is important for oxidation and $Ce^{3+}$, combined with electron shuffling through oxygen vacancies, is important for reduction.[13,14] Das et al. reported that CNPs protect adult rat spinal cord neurons against oxidative stress.[25] Other previous studies have shown that nanoceria could protect photoreceptor cells, radiation-induced cellular damage, nerve cell protection and others.[26-31] Naturally occurring ROS include the superoxide (O2•—) and hydroxyl radicals (•OH), the former one being the most common one in the cell since it is a byproduct of aerobic respiration. Hydroxyl radicals represent the most damaging ROS and are formed in macrophages and microglia when exposed to certain bacteria, or when biological tissue is exposed to ionizing radiation. Typically, ROS are removed from cells via enzymes such as superoxide dismutase (SOD), which catalyzes the disproportionation of superoxide to oxygen gas and hydrogen peroxide; or catalase, which is responsible for the degradation of $H_2O_2$ to water and dioxygen. CNPs have shown SOD and catalase mimetic behavior depending on different variables such as $Ce^{3+}/Ce^{4+}$ ratio, size, morphology, surface coatings, and environmental conditions.[24,32] For example, Xue et al. demonstrated that 5-10 nm nanoceria has greater antioxidant activity than 15-20 nm CNPs due to the increased surface density of $Ce^{3+}$ for the smaller nanoparticles, therefore enabling them to scavenge a greater amount of •OH.[33] However, the oxidizing ability of CNPs has also been reported, and may have a pro-oxidative effect through a possible Fenton-like reaction.[32] Xu and Que investigated whether nanoceria act directly as an oxidase or as an oxidant in the oxidation of organic dyes and determined that the pH of the environment affected the reactivity—nanoceria can act as a consumable oxidant under acidic conditions, whereas in neutral or basic conditions the $Ce^{3+}/Ce^{4+}$ cycling can be maintained catalytically allowing nanoceria to act as an oxidase.[13] Finally, Lu et al. demonstrated that several factors, such as concentration of OH—, and the sizes, morphologies and concentrations of nanoceria could result in conversion between antioxidant and oxidant activity.[34] In addition other factors such as synthetic methods, composition, surface charge, pH and particle aggregation have been suggested as possible causes for CNPs toxicity.[14, 32, 35] Due to the immense promise of CNPs to serve as antioxidants, further, well controlled studies should be carried out to address exactly which properties of CNPs affect the reactivity and which ones result in toxic conditions. However, because size and surface features cannot be controlled very well and because the $Ce^{3+}/Ce^{4+}$ ratio is difficult to determine with confidence, it can be challenging to address the reactivity of these CNPs in a controlled manner.

Atomically-precise cerium-oxide nanoclusters are feasible through the synthesis and characterization of $Ce_{24}$ (4), $Ce_{38}$ (6) and $Ce_{40}$ (7) have recently been demonstrated, as shown above. These clusters are on the nanometer scale while still displaying the fluorite structure of $CeO_2$ and therefore represent true molecular pieces of $CeO_2$. Further extension of the family of Ce/O nanoclusters are reported herein in both size and $Ce^{3+}/Ce^{4+}$ ratio through the synthesis and characterization to atomic precision of $[Ce_6O_4(OH)_4(H_2O)_4(dmb)_{12}](Ce_6; 1;$ dmb=anion of dimethoxybenzoic acid), $[Ce_{16}O_{17}(OH)_6(O_2CPh)_{24}(HO_2CPh)_3(H_2O)]$ $(Ce_{16};$ 2), $[Ce_{19}O_{18}(OH)_{10}(O_2CPh)_{26}(H_2O)(py)_3](Ce_{19};$ 3) and $[Ce_{24}O_{27}(OH)_9(PhCO_2)_{30}(py)_4]$ $(Ce_{24};$ 5), which is similar to the previously reported $Ce_{24}$ (4), but possesses one more reduced ion. With a family of seven atomically-precise Ce/O nanoclusters, the ROS scavenging ability of this family of nanoclusters as a function of size and $Ce^{3+}/Ce^{4+}$ ratio was investigated though the use of spin-trap techniques in conjunction with electron paramagnetic resonance (EPR) spectroscopy. Results as shown herein indicate that while size may not play a role in the effectiveness of scavenging •OH, nanoclusters with a low concentration of $Ce^{3+}$ or no $Ce^{3+}$ can scavenge •OH more effectively than those with a higher concentration of $Ce^{3+}$.

EXPERIMENTAL SECTION

All manipulations were performed under aerobic conditions using chemicals and solvents as received, unless otherwise stated. $[Ce_{24}O_{28}(OH)_8(PhCO_2)_{30}(py)_4]$ (4; also referred to as $Ce_{24}$), $[Ce_{38}O_{54}(OH)_8(EtCO_2)_{36}(py)_8]$ (6; also referred to as $Ce_{38}$) and $[Ce_{40}O_{54}(OH)_4(MeCO_2)_{46}(py)_4]$ (7; also referred to as $Ce_{40}$) were prepared as reported previously.

$[Ce_6O_4(OH)_4(H_2O)_4(dmb)_{12}]$ (1; also referred to as $Ce_6$). To a stirred solution of dmbH (1.5 g, 8.0 mmol) in $MeNO_2$ was added $Fe(NO_3)_3·9H_2O$ (0.40 g, 1.0 mmol), $(NH_4)_2[Ce(NO_3)_6]$ (0.55 g, 1.0 mmol) and $NEt_3$ (1.1 mL, 8.0 mmol), which caused the solution to turn dark red and begin to deposit a white precipitate. The slurry was stirred a further 10 min and then filtered. The mother liquor was allowed to stand undisturbed for two days at room temperature, during which time large yellow blocks of 1·8MeNO₂ slowly formed. The crystals were collected by filtration, washed with $MeNO_2$ and dried in vacuum. The yield was 79% based on Ce. Anal. Calcd (Found) for 1·5H₂O·3MeNO₂ $(C_{111}H_{139}N_3Ce_6O_{47})$: C, 38.05 (37.69); H, 4.00 (3.50); N, 1.20 (1.28). Selected IR data (KBr disk, cm−1): 3457 (mb), 2941 (w), 2838 (w), 1595 (s), 1557 (s), 1473 (s), 1403 (s), 1251 (s), 1174 (w), 1142 (w), 1109 (s), 1029 (w), 838 (w), 816 (w), 769 (w), 736 (w), 631 (w), 596 (w), 551 (m).

$[Ce_{16}O_{17}(OH)_6(O_2CPh)_{24}(HO_2CPh)_3(H_2O)]$ (2; also referred to as $Ce_{16}$). To a stirred solution of $PhCO_2H$ (0.98 g, 8.0 mmol) in MeCN was added $Fe(NO_3)_3·9H_2O$ (0.40 g, 1.0 mmol), $(NH_4)_2[Ce(NO_3)_6]$ (0.55 g, 1.0 mmol) and $NEt_3$ (1.1 mL, 8.0 mmol), which caused the solution to turn dark red and begin to deposit a white precipitate. The slurry was stirred a further 10 min and then filtered. The mother liquor was allowed to stand undisturbed for two weeks at room temperature, during which time yellow blocks of 2·15MeCN·5H₂O slowly formed. The crystals were collected by filtration, washed with MeCN and dried in vacuum. The yield was 7% based on Ce. Anal. Calcd (Found) for 2·2MeCN $(C_{193}H_{152}N_2Ce_{16}O_{78})$: C, 39.25 (39.34); H, 2.59 (2.77); N, 0.47 (0.50). Selected IR data (KBr disk, cm−1): 3435 (mb), 3061 (w), 1594 (m), 1534 (s), 1492 (w), 1448 (w), 1403 (s), 1307 (w), 1178 (w), 11070 (w), 1025 (w), 849 (w), 716 (s), 687 (w), 584 (w), 510 (m), 427 (m).

$[Ce_{19}O_{18}(OH)_{10}(O_2CPh)_{26}(H_2O)(py)_3]$ (3; also referred to as $Ce_{19}$). To a stirred solution of pyridine/water (10:1 mL v/v) was added $(NH_4)_2[Ce(NO_3)_6]$ (0.55 g, 1.0 mmol), $PhCO_2H$ (0.24 g, 2.0 mmol), and $NH_4I$ (0.14 g, 1.0 mmol). The golden yellow solution was stirred for 30 minutes, followed by the addition of 20 mL of MeCN to the solution. The solution was then left to sit for three days, during which time X-ray quality yellow square plates of 3·3.5py·8MeCN formed. The crystals were collected by filtration, washed with MeCN and dried in vacuum. The yield was 25% based on Ce. Anal. Calcd (Found) for 3-10H$_2$O-MeCN ($C_{199}H_{178}N_4Ce_{19}O_{90}$): C, 35.53 (35.18); H, 2.67 (2.40); N, 0.83 (1.00). Selected IR data (KBr disk, cm−1): 3430 (mb), 3134 (mb), 1594 (m), 1534 (s), 1492 (w), 1447 (w), 1402 (s), 1307 (w), 1178 (w), 1069 (w), 1025 (w), 849 (w), 717 (s), 688 (w), 558 (w), 514 (m), 489 (m) 406 (s).

[$Ce_{24}O_{27}(OH)_9(O_2CPh)_{30}(py)_4$] (5; also referred to as $Ce_{24}$). To a stirred solution of pyridine (10 mL) was added Ce(NO$_3$)$_3$·6H$_2$O (0.43 g, 1.0 mmol) and PhCO$_2$H (0.24 g, 2.0 mmol). The colorless solution was stirred for 30 minutes, followed by the addition of 20 mL of MeCN to the solution. The solution was then left to sit for one week, during which time X-ray quality brown square plates of 5·3.75py formed. The crystals were collected by filtration, washed with MeCN and dried in vacuum. The yield was 30% based on Ce. Anal. Calcd (Found) for 5-3py ($C_{245}H_{193}N_7Ce_{24}O_{96}$): C, 36.18 (36.37); H, 2.39 (2.41); N, 1.21 (1.22). Selected IR data (KBr disk, cm−1): 5333 (w), 3064 (m), 1594 (s), 1537 (s), 1492 (w), 1448 (w), 1405 (s), 1307 (w), 1178 (w), 1142 (w), 1070 (w), 1025 (w), 849 (w), 717 (s), 679 (w), 558 (w), 513 (m), 488 (m) 408 (s).

DMPO Spin-Trap Sample Preparation. Immediately before the EPR measurements, each sample was prepared by mixing H$_2$O$_2$(10 mM), DMPO (0.5 mM), and ceria nanoclusters (1 mM) in water. FeCl$_2$ (10 mM) was added last to generate OH• radicals. Upon addition of FeCl$_2$ a timer was started to ensure that each sample had the same time to react. The mixture was vortexed for 10 seconds and immediately transferred to a capillary. After 1 minute of total time, the first EPR spectrum of the time scan was recorded. Successive scans were recorded at a one minute interval for a total time course of ten minutes. For the control samples, the same procedure was followed as above, except that the addition of ceria nanoclusters was replaced with an equal volume of water. Additional control experiments with each nanocluster were carried out replacing FeCl$_2$ with an equal volume of water.

X-ray Crystallography. Data were collected for 1·8MeNO$_2$, 2·15MeCN·5H$_2$O, 3·3.5py·8MeCN, and 5·3.75py at 100 K on a Bruker DUO diffractometer using Mo Kα radiation (Δ=0.71073 Å) and an APEXII CCD area detector.

Raw data frames were read by the program SAINT[36] and integrated using 3D profiling algorithms. The resulting data were reduced to produce hkl reflections and their intensities and estimated standard deviations. The data were corrected for Lorentz and polarization effects and numerical absorption corrections were applied based on indexed and measured faces.

The structure was solved and refined in SHELXTL2013[37] for 1·8MeNO$_2$ and SHELXTL2014[38] for 2·15MeCN·5H$_2$O, 3·3.5py·8MeCN, and 5·3.75py, using full-matrix least-squares refinement. The non-H atoms were refined with anisotropic thermal parameters and all of the H atoms were calculated in idealized positions and refined riding on their parent atoms.

For 1·8MeNO$_2$, the asymmetric unit comprises a half Ce$_6$ cluster, a water molecule and four nitromethane solvent molecules. The four solvent molecules were disordered and could not be modeled properly, thus program SQUEEZE[39], a part of the PLATON[40] package of crystallographic software, was used to calculate the solvent disorder area and remove its contribution to the overall intensity data. The oxygen of the trapped water molecule, O31 is disordered and was refined against O31'. It is important to note that their protons were not disordered but were obtained from a Difference Fourier map and refined freely. Similarly, the protons of coordinated water oxygen ligands, O29 and O30, were refined freely. In the final cycle of refinement, 16226 reflections (of which 14605 are observed with I>2σ(I)) were used to refine 839 parameters and the resulting R1, wR$_2$ and S (goodness of fit) were 2.77%, 6.84% and 1.085, respectively. The refinement was carried out by minimizing the wR$_2$ function using F$^2$ rather than F values. R$_1$ is calculated to provide a reference to the conventional R value but its function is not minimized.

For 2·15MeCN·5H$_2$O, the Ce$_{16}$ clusters are located on 3-fold rotational axes thus a third occupies the asymmetric unit. In addition to the clusters, there are fifteen acetonitrile solvent molecules (ratio is 1/3 cluster with five solvent molecules). The solvent molecules were disordered and could not be modeled properly, thus program SQUEEZE[39], a part of the PLATON[40] package of crystallographic software, was used to calculate the solvent disorder area and remove its contribution to the overall intensity data. The cluster also exhibits a disordered benzoate ligand (C21-C27) refined in two parts with the minor part being C21'-C27'. The hydroxy protons on O2 and O9 were obtained from a Difference Fourier map and refined freely. But the proton on O15 was placed in an idealized position and was refined riding on its parent atom. The protons of the coordinated water ligand, O7, could not be located and were thus not included in the final refinement model. Because of proximity to disordered parts of the cluster, there were five water molecules that could not be removed by SQUEEZE and were refined in the final model of the structure. They were O1'-O5'. In the final cycle of refinement, 13114 reflections (of which 6272 are observed with I>2σ(I)) were used to refine 769 parameters and the resulting R$_1$, wR$_2$ and S (goodness of fit) were 6.62%, 17.68% and 0.914, respectively. The refinement was carried out by minimizing the wR$_2$ function using F$^2$ rather than F values. R$_1$ is calculated to provide a reference to the conventional R value but its function is not minimized.

For 3·3.5py·8MeCN, the asymmetric unit comprises the Ce$_{19}$ cluster, three and a half pyridine solvent molecules and eight acetonitrile solvent molecules. One of the phenyl rings is disordered and refined in two parts. Another disorder is between a water ligand (water protons could not be located) and a pyridine ligand. All of the rings were constrained to maintain ideal geometry using the AFIX 66 command. The acetonitrile solvent molecules were significantly disordered and could not be modeled properly, thus program SQUEEZE[39], a part of the PLATON[40] package of crystallographic software, was used to calculate the solvent disorder area and remove its contribution to the overall intensity data. In the final cycle of refinement, 44246 reflections (of which 17558 are observed with I>2σ(I)) were used to refine 1400 parameters and the resulting R1, wR$_2$ and S (goodness of fit) were 7.93%, 18.85% and 0.977, respectively. The refinement was carried out by minimizing the wR$_2$ function using F$^2$ rather than F values. R$_1$ is calculated to provide a reference to the conventional R value but its function is not minimized.

For 5·3.75py, the asymmetric unit comprises a half Ce$_{24}$ cluster and 3.75 pyridine solvent molecules disordered over seven locations. Oxygen protons could not be located from Difference Fourier maps thus four of those were calculated in calculated idealized positions on O12, O14, O15 and O16. On the other hand, no protons were found on the nitrogen atoms of the pyridine rings. Uncertainty remains regarding the protonation of any of the pyridine molecules. In the final cycle of refinement, 25279 reflections (of which 15097 are observed with I>2σ(I)) were used to refine 1433 parameters and the resulting $R_1$, $wR_2$ and S (goodness of fit) were 9.38%, 23.38% and 1.500, respectively. The refinement was carried out by minimizing the $wR_2$ function using $F^2$ rather than F values. $R_1$ is calculated to provide a reference to the conventional R value but its function is not minimized.

Physical Measurements. Infrared spectra were recorded in the solid state (KBr pellets) on a Nicolet Nexus 670 FTIR spectrometer in the 400-4000 cm-1 range. Elemental analyses (C, H, and N) were performed by the in-house facilities of the University of Florida, Chemistry Department for 1 and at Atlantic Microlab, Inc. for 2, 3, and 5. Electron paramagnetic resonance (EPR) measurements were recorded on a Bruker ELEXSYS-II E500 with a Bruker 4116DM resonator mounted on an Oxford Instruments CF900 helium cryostat for low temperature experiments. For 3, data were collected at 5 K in the 50 to 7050 G field range temperature with the following parameters: power 6.32×10−1 mW, frequency 9.65 GHz, modulation frequency 100.00 kHz, modulation amplitude 10.00 G, 80.00 ms conversion time and 4,000 data points. For 5, data were collected at 10 K in the 50 to 7050 G field range with the following parameters: power 6.32×10−1 mW, frequency 9.43 GHz, modulation frequency 100.00 kHz, modulation amplitude 10.00 G, 80.00 ms conversion time and 2,048 data points. For the DMPO spin-trap experiments data were collected using a Bruker SHQE resonator at room temperature in the 3435 to 3585 G field range and typical acquisition parameters were: power $20.00 \times 10^{-1}$ mW, frequency 9.86 GHz, modulation frequency 100.00 kHz, modulation amplitude 1.00 G, 40.00 ms conversion time and 1,024 data points.

Results and Discussion

Syntheses. Both complex 1 and 2 were synthesized through a similar reaction. The reaction of 2,6-dimethoxybenzoic acid (dmbH), $Fe(NO_3)_3 \cdot 6H_2O$, $(NH_4)_2[Ce(NO_3)_6]$, and $NEt_3$ in an 8:1:1:8 ratio in MeCN or $MeNO_2$ led to the isolation of 1·8MeNO$_2$ in 79% yield. A similar reaction, employing benzoic acid in place of dmbH led to the isolation of 2·15MeCN in 7% yield. The ratios were systematically explored, but either did not produce any product, or did not improve the yield of the reaction. One of the striking features of this reaction is that no Fe is incorporated in the final product, however, attempts to synthesize 1 or 2 in the absence of Fe were unsuccessful. A different $Ce_6$ complex published by Powell, et al. demonstrated a similar transition metal effect in which no product was formed in the absence of either Cu or Mn.[41]

Complexes 3 and 5 were synthesized in a similar manner to those reported in examples above. The reaction of ceric ammonium nitrate (CAN), $PhCO_2H$, and $NH_4I$, in a 1:2:1 ratio in py:$H_2O$ (10:1 mL) gave complex 3·3.5py·8MeCN in a 25% yield. Complex 3 contains four reduced ions, and a different nuclearity than 4 demonstrating that the oxidation state of Ce present in the final product as well as the nuclearity can be affected by small changes to the reaction scheme since in the synthesis of 4 no reducing agent was added.

When a $Ce^{3+}$ source was employed, $Ce(NO_3)_3$, in place of CAN in the reaction scheme of 4, complex 5·7.5py was synthesized. The reaction of $Ce(NO_3)_3 \cdot 6H_2O$ and $PhCO_2H$ in a 1:2 ratio in py (10 mL) with MeCN added for crystallization gave 5·7.5py in 30% yield. Complex 5 has the same topology as 4, but has an additional reduced ion as determined by BVS calculations and EPR measurements (vide infra).

Description of Structures. Complex 1 (also referred to as $Ce_6$) comprises a central $Ce_6$ octahedron with a carboxylate group capping each face (FIGS. 38A-38C). The core comprises a $[Ce_6(\mu_3\text{-O})_4(\mu_3\text{-OH})_4]^{12+}$ octahedron in which the faces of the octahedron are bridged by a $\mu_3$-O or $\mu_3$-OH$^-$ (FIGS. 38A-38C). All Ce ions were determined to be in their +4 oxidation state from bond valence sum (BVS) calculations (Table S1). The protons on the OH$^-$ groups were not located crystallography, but rather Ce—O bond lengths, BVS calculations and charge balance were used to determine the protonated oxides (Table S2). O1 and O3 have average Ce—O bond lengths of 2.295(3) Å and O2 and O4 have average Ce—O bond lengths of 2.286(3) and 2.283(3) Å, respectively. This suggests that O2 and O4 are oxygen anions while O1 and O3 are OH$^-$ groups, however there is no obvious reason for the H$^+$ to prefer one location over another and they could be disordered between O1-O4. The dmb-groups are all bridging in their familiar η1:η1:μ-mode and bridge all 12 edges of the octahedron. $Ce_2$ and $Ce_3$ are both nine-coordinate while Ce1 is eight-coordinate. The $Ce^{IV}_6$ cluster has been reported previously in slightly different forms while still containing the same octahedral $\{Ce_6(\mu\text{-}O^{2-})_x(\mu\text{-}OH^-)_{8-x}\}$ core, but at different protonation levels and varying ligation.[41-46]

Figure 39A:
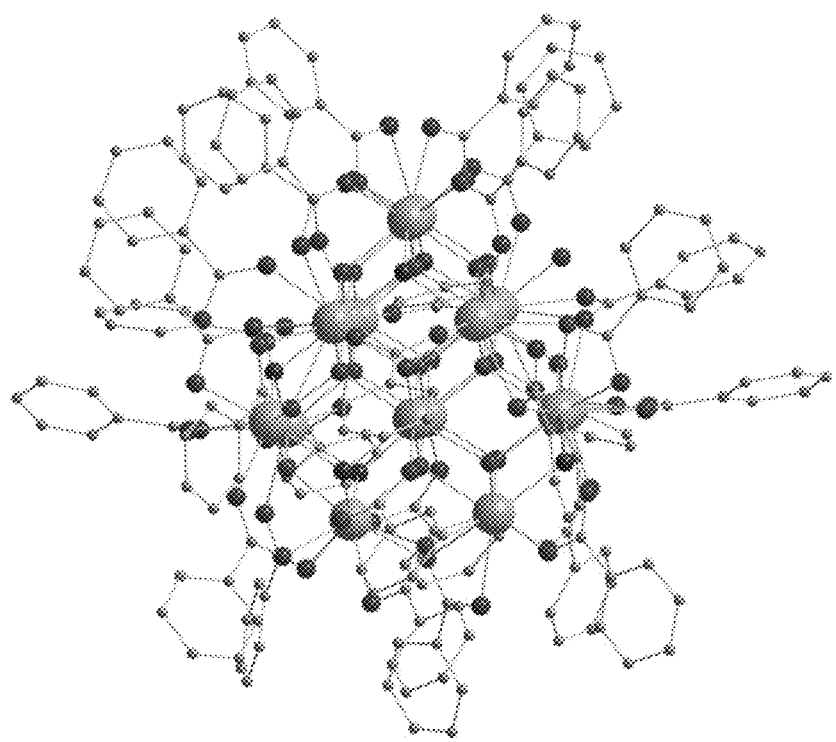
FIGS. 39A-39C show the full structure of complex 2 (FIG. 39A), core of complex 2 (FIG. 39B) and core in facet view (FIG. 39C). Color code: $Ce^{IV}$ gold, O red, protonated O (i.e. $OH^-$) purple, C grey. H atoms have been omitted for clarity. Green surfaces represent the (111) facet.
Figure 39B:
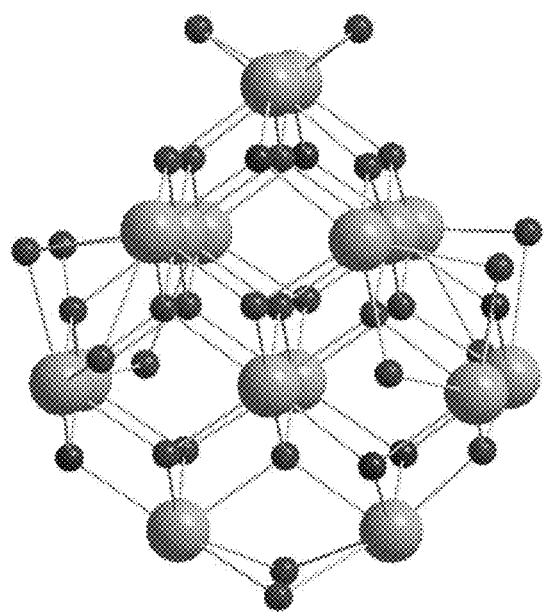
Figure 39C:
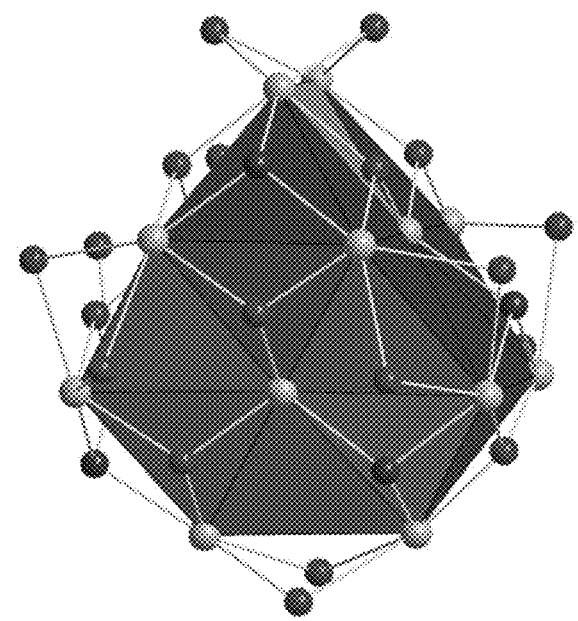

Complex 2 (also referred to as $Ce_{16}$; FIGS. 39A-39C) comprises a $[Ce_{16}(\mu_4\text{-O})_7(\mu_3\text{-O})10(\mu\text{-OH})_6]^{24+}$ core that truly resembles the bulk $CeO_2$ structure. The fluorite structure that makes up the core of 2 can be described as alternating layers of Ce and oxides/hydroxides, where the Ce ions are linked by tetrahedral oxides. All of the Ce ions are in their +4 oxidation state (Table S3). Four of the Ce ions are eight-coordinate and 12 are nine-coordinate. The ligation is completed by 24 $PhCO_2$ groups, three $PhCO_2H$ and one terminal $H_2O$. Twelve of the $PhCO_2$ groups are in their regular η1:η1:μ-bridging mode and 12 of the $PhCO_2$ groups chelate and bridge. The protons on O2 and O9 were located crystallographically, but the proton on O15 was placed in an idealized position and refined. The protons on O7 were not located crystallographically, but were instead assigned on the basis of BVS calculations and charge balance considerations (Table S4).

Figure 47:
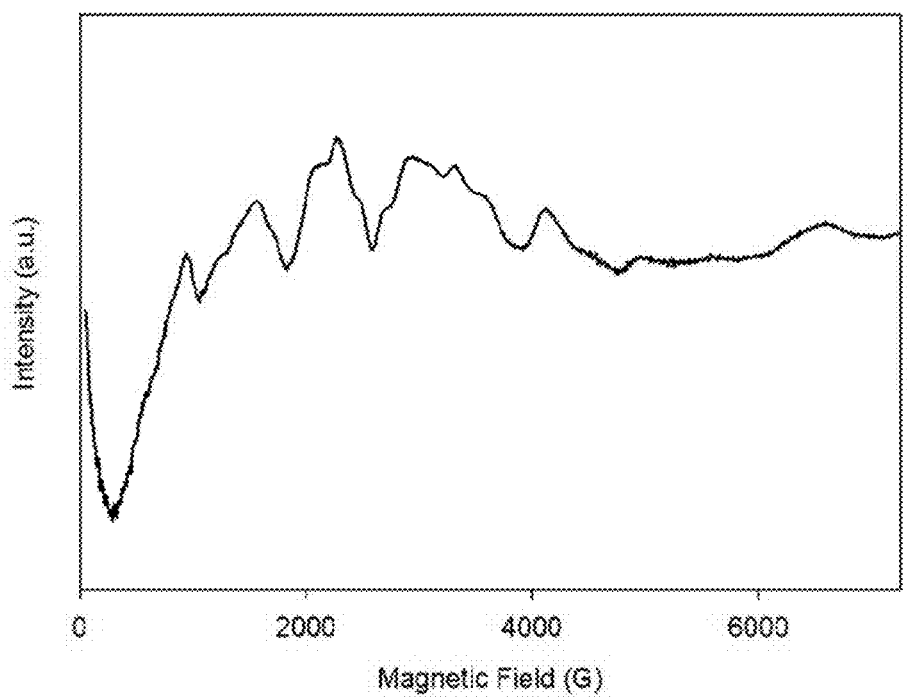
FIG. 47 is an EPR spectrum of $Ce_{19}$ nanocluster 3 as a microcrystalline powder at 5.0 K in the 0 to 7000 G field range in parallel mode.

Complex 3 (also referred to as $Ce_{19}$; FIGS. 40A-40C) comprises a $[Ce_{19}O_{18}(OH)_{10}]^{26+}$ core that again resembles the fluorite structure of $CeO_2$. There are four reduced ions, $Ce_2$, $Ce_{17}$, $Ce_{18}$ and $Ce_{19}$, as determined by BVS calculations (Table S5), which all reside on the outside of the core. The reduced ions do cause deviations from ideal fluorite positions, however, the fluorite structure is still retained. Five of the Ce ions are eight-coordinate and 14 of the Ce ions are nine-coordinate; all of the $Ce^{3+}$ ions are nine-coordinate. There are 18 oxide ions in the core and ten hydroxide groups and one terminal water ligand coordinated to $Ce_{16}$. The protons were not located crystallographically but were instead determined from BVS calculations (Table S6). The presence of unpaired electrons from $Ce^{3+}$ ions was confirmed via EPR spectroscopy (FIG. 47). The ligation is completed by 26 $PhCO_2^-$ and 3 py molecules, with one py disordered with a water molecule.

Figure 48:
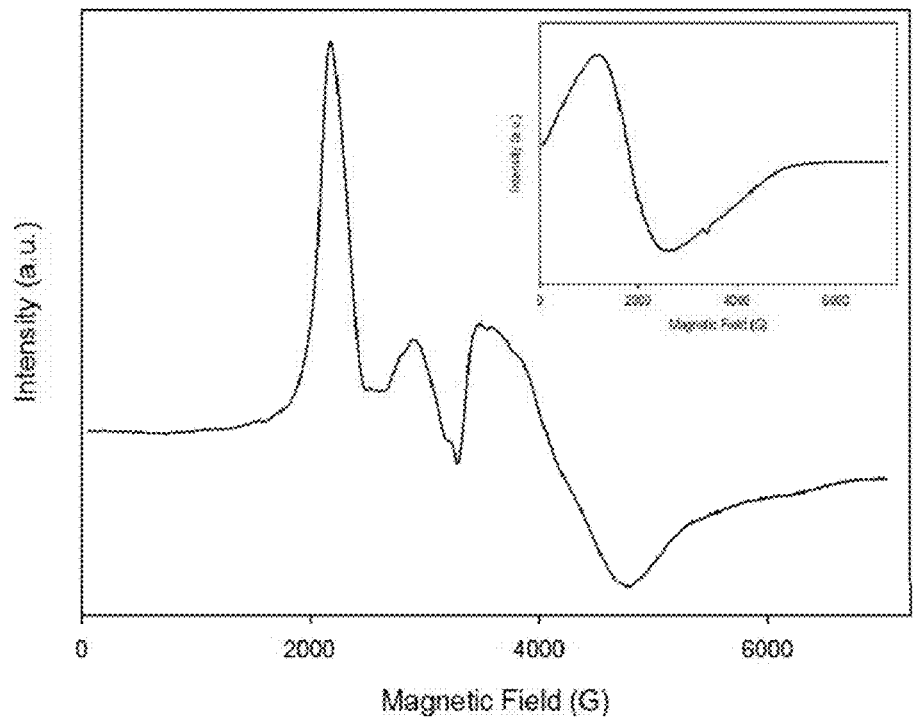
FIG. 48 is an EPR spectrum of $Ce_{24}$ nanocluster 5 as a microcrystalline powder at 10.0 K in the 0 to 7000 G field range. The large signal around 3500 G is from a Cu impurity present in the resonator. Inset is the EPR spectrum of 4 for comparison.
Figure 49A:
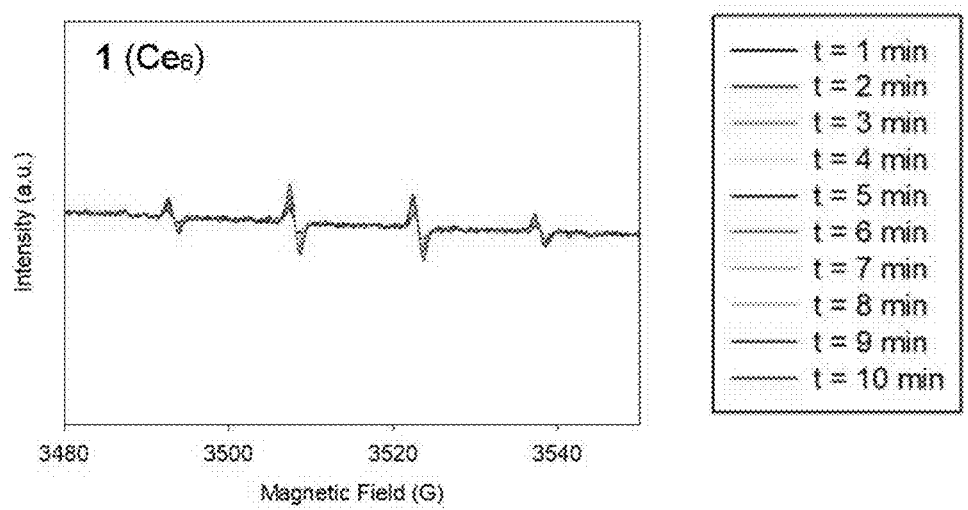
FIGS. 49A-49C are EPR spectra of the DMPO spin-trap adduct generated from the reaction between $H_2O_2$ (10 mM), DMPO (0.5 M) and 1 mM of the corresponding Ce nanocluster ($Ce_6$, FIG. 49A; $Ce_{16}$, FIG. 49B; and $Ce_{19}$, FIG. 49C) in the absence of Fe. All of the plots have the same scaling of the intensity axis (−1.0 to 1.0) except for 7 (−1.2 to 1.2).
Figure 49B:
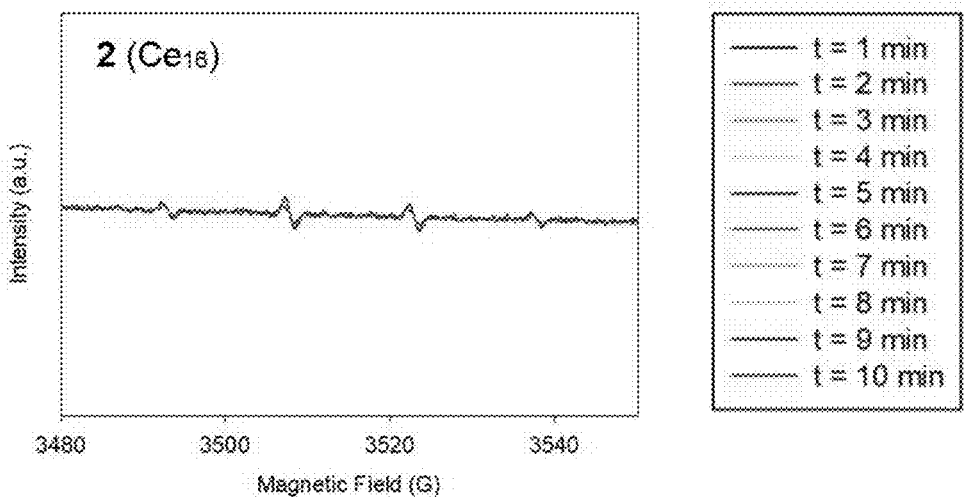
Figure 49C:
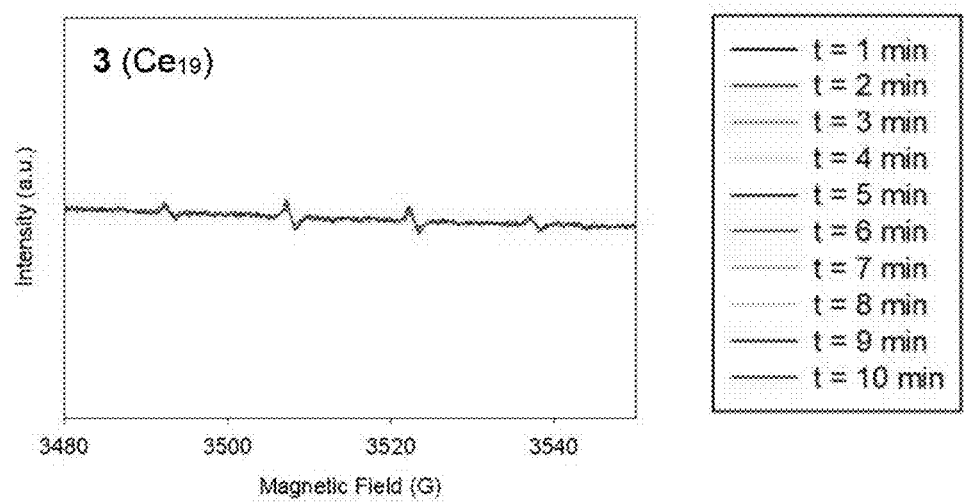
Figure 50A:
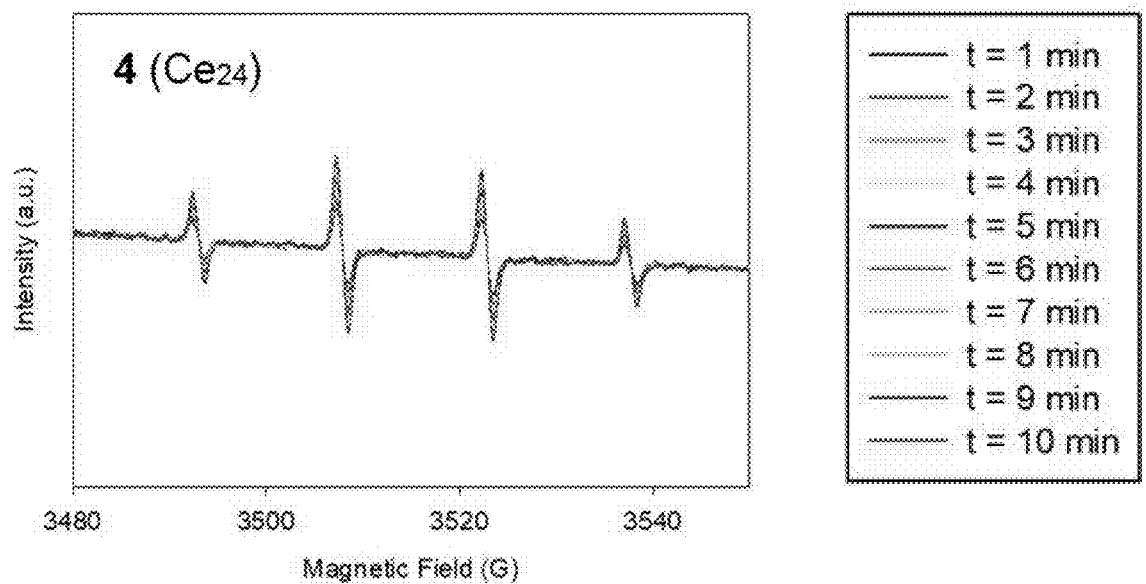
FIGS. 50A-50D are EPR spectra of the DMPO spin-trap adduct generated from the reaction between $H_2O_2$ (10 mM), DMPO (0.5 M) and 1 mM of the corresponding Ce nanocluster ($Ce_{24}$ (complex 4), FIG. 50A; $Ce_{24}$ (complex 5), FIG. 50B; $Ce_{38}$, FIG. 50C, and $Ce_{40}$, 50D), in the absence of Fe. All of the plots have the same scaling of the intensity axis (−1.0 to 1.0) except for 7 (−1.2 to 1.2).
Figure 50B:
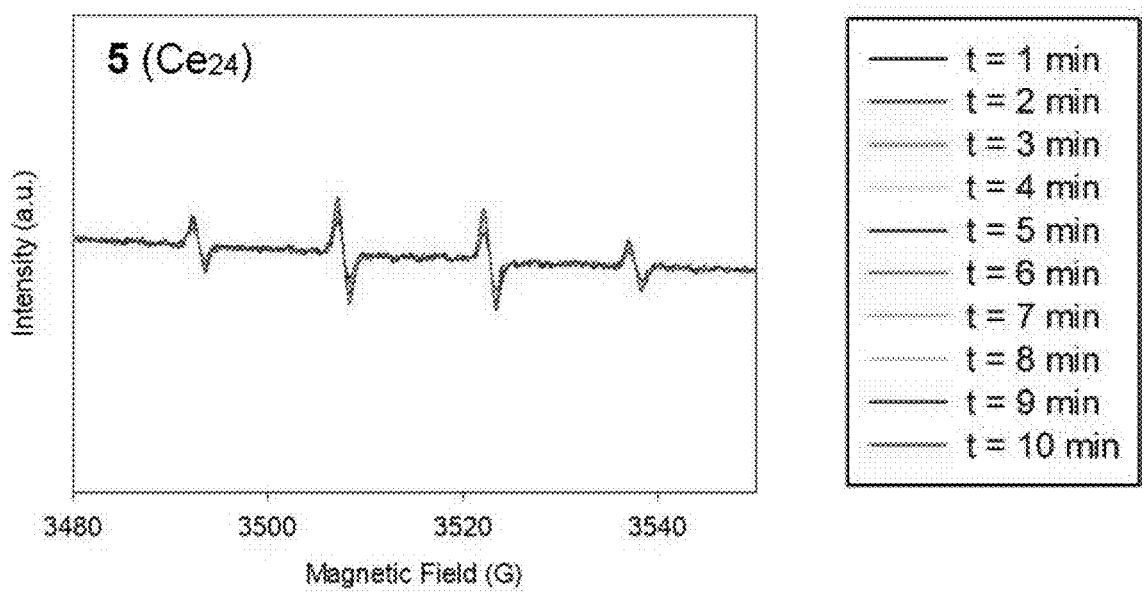
Figure 50C:
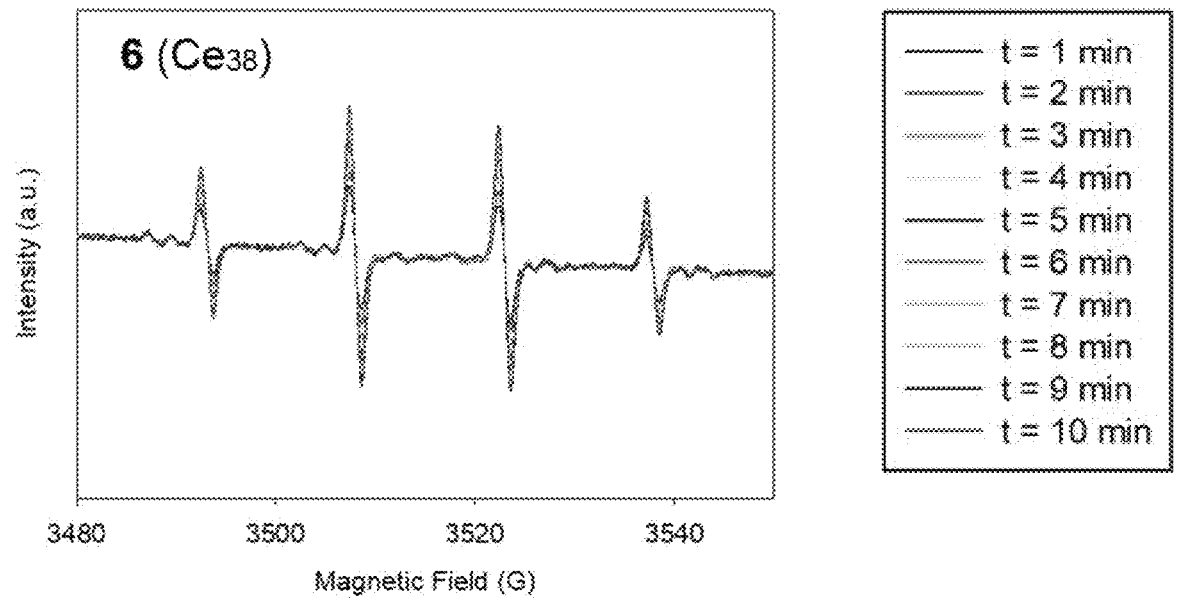
Figure 50D:
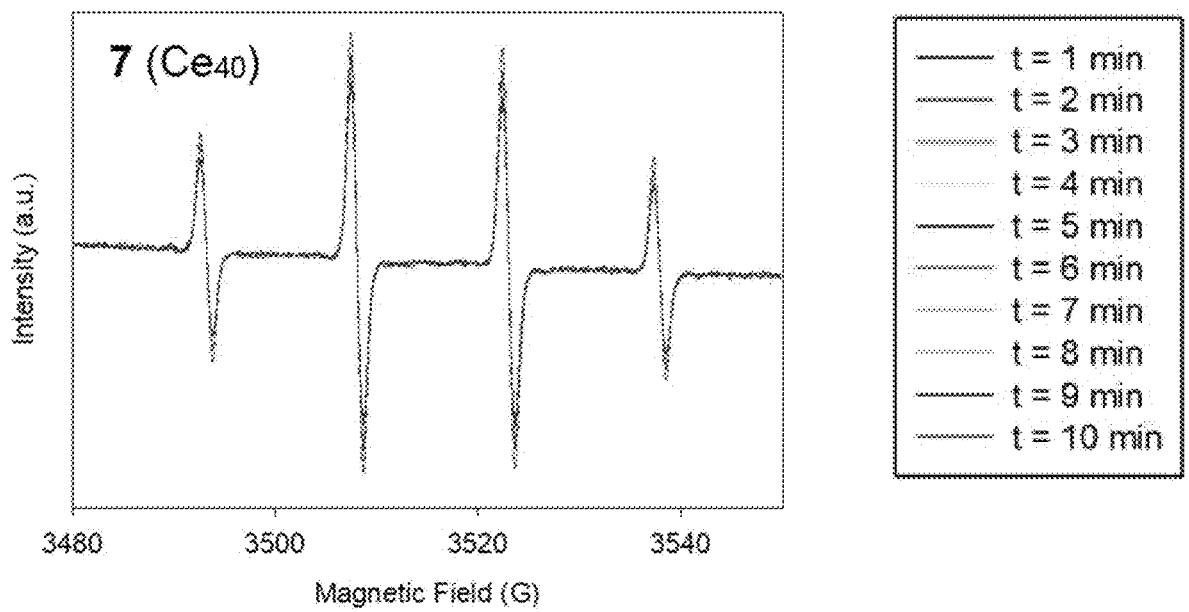

Complex 5 (also referred to as $Ce_{24}$; FIGS. 41A-41C) is structurally identical to the previously reported complex 4. The only difference is in the oxidation state of one of the Ce ions, specifically $Ce_9$, as determined by BVS calculations (Table S7) and EPR measurements (FIG. 48). The core comprises 21 $Ce^{4+}$ ions and three $Ce^{3+}$ ions in contrast to 4 which comprises 22 $Ce^{4+}$ ions and two $Ce^{3+}$ ions. The additional $Ce^{3+}$ ion was identified based on the intermediate BVS value of ~3.5. Since $Ce_4$ is related to another Ce ion by symmetry, we interpret this as one ion is a $Ce^{3+}$ ion and the other one is a $Ce^{4+}$ ion. The EPR spectrum for this complex, in comparison to 4, shows different features, indicating that there are additional unpaired electrons from the third $Ce^{3+}$ ion and these unpaired electrons may be interacting with one another. O19 has a slightly lower BVS value in 5 (1.64) than in 4 (1.71) which could be the site of a disordered proton for charge balance, especially given that all other O BVS values for 5 are almost identical to the corresponding O BVS value for 4 (Table S8). Additionally, there is no reason for $H^+$ to favor a particular $\mu_3$-$O_2^-$ ion when so many are essentially equivalent. Ten of the Ce ions are eight-coordinate, 12 of the Ce ions are nine-coordinate and two of the Ce ions are ten-coordinate, both of which are $Ce^{3+}$ ions. There are 27 bridging $O_2^-$ ions in the core along with nine $OH^-$ groups that were identified based on BVS calculations. The remaining ligation is provided by 30 $PhCO_2$ ligands and four terminal py ligands.

Comparing the Ce/O nanoclusters that are shown herein, there are some overall themes that are evident from this family (FIG. 42): (i) they all exhibit the same fluorite structure of bulk $CeO_2$, with central eight-coordinate cubic $Ce^{4+}$ ions and surface $Ce^{3+}$ or $Ce^{4+}$ ions in various coordination environments; (ii) 3, 4, 5, and 7 all contain various $Ce^{3+}/Ce^{4+}$ ratios, 4 and 7 contain two and 3 and 5 contain four and three $Ce^{3+}$ ions respectively. All $Ce^{3+}$ ions are positioned on the outside of the core where they are coordinated to fewer oxides than central $Ce^{4+}$ ions; (iii) they have $Ce_xO_y$ core diameters (largest Ce•• Ce distance) from about 0.5 nm to over 1.5 nm; (iv) all of the nanoclusters display facets as do CNPs (FIG. 42), although 1 may represent the size limit for which this is possible. Complexes 1 and 2 possess only (111) facets, while 3, 4, 5, and 7 display (111) and (100) facets, and 7 displays all three facets (111), (100), (110) and (v) there is a common structural motif of a $\mu_3$- or $\mu_4$-$OH^-$ capping a $Ce_4$ square in a strained environment, which may be a site of increased reactivity.

At the surface, the edges of $Ce_4$ squares are carboxylate-bridged and a $\mu_3$- or $\mu_4$-$OH^-$ caps the whole square. Interestingly, when $Ce^{3+}$ ions are present they occur within (100) $Ce^4$+$3Ce^{3+}$ squares, except for $Ce_2$ in 3. Complexes 3, 4, 5, 6, and 7 contain three, four, four, six, and two such squares respectively. 3 contains three (100) squares in which the $\mu_4$-$OH^-$ that has been observed in 4, 6, and 7 has now become $\mu_3$-$OH^-$ because there are two $Ce^{3+}$ ions contained in the square. This can cause the $\mu_3$-$OH^-$ to move slightly out of the center of the square, shifting it ~3.5 Å from one of the $Ce^{3+}$ ions. To demonstrate this point, from the view of FIG. 43, 3, 4, and 5 all have a very similar arrangement of Ce and O/$OH^-$ ions at one end of the core, but they differ in the number of $Ce^{3+}$ ions and the locations of $OH^-$ groups. From this view, complex 4, has two $Ce_4$ squares, with the $Ce^{3+}$ ion ($Ce_4$) joining the two squares and a $\mu_4$-OH— capping each square. There is one extremely long interaction from $Ce_4$ to O14 that is ~3.0 Å (Table S9), however, upon further reduction as in 5, the longest interaction is now between $Ce_4$ and O12 (2.91 Å). Once this area is further reduced as in 3, the OH group shifts away from one of the $Ce^{3+}$ ions in the square, breaking one interaction within each square becoming $\mu_3$-$OH^-$ groups, demonstrating the flexibility and adaptability of these sites. This direct comparison of the same structural motif in three different clusters with different $Ce^{3+}$:$Ce^{4+}$ ratios provides further evidence for favorable environments for $Ce^{3+}$ ions. Within the (100) squares, if there is a long $\mu_4$-$OH^-$••$Ce^{3+}$ bond, then within that square it can become more favorable for a $Ce^{3+}$ ion. Once there are (100) squares that join together and contain two $Ce^{3+}$ ions each, it is now more favorable for the $OH^-$ group to move closer to the $Ce^{4+}$ ions and away from the two $Ce^{3+}$ ions in the square. These $\mu_4$-$OH^-$ capping Ce4 (100) squares may be possible sites of O vacancies and the shift to $\mu_3$-$OH^-$ observed in 3 in squares containing two $Ce^{3+}$ ions provides further support for this hypothesis. In addition, the absence of $Ce^{3+}$ ions in 1 and 2 can therefore be attributed to these complexes displaying only (111) facets and no (100) and the absence of $Ce^{3+}$ ions in 3 can be attributed to the lack of joining (100) facets.

Radical Scavenging Activity of Ce/O Nanoclusters. While the structural information gained about the surface of these nanoclusters is informative, the question then still remains if they still exhibit the catalytic activity characteristic of CNPs. To answer this, their ability to scavenge ROS radicals was explored, an important test reaction of CNP catalytic activity in the <20 nm range in biomedical applications.[48]

To probe the hydroxyl radical scavenging ability of 1-7 in a controlled manner, EPR spectroscopy was employed to monitor spin-trapped hydroxyl radicals by using the 5,5-dimethyl-1-pyrroline N-oxide (DMPO) spin-trap. The half-life of hydroxyl radicals in solution at room temperature is very short, but by reacting these unstable radicals with nitrones or nitroso compounds, long-lived nitroxide radicals can be formed which can be detected, quantified, and monitored by EPR spectroscopy. The characteristic DMPO/•OH adduct spectrum comprises can comprise four lines with peak intensity ratios 1:2:2:1 due to the overlap between the hyperfine coupling of the unpaired electron with the N and the β-H. They have the same hyperfine coupling constant of 14.9 G. Hydroxyl radicals were generated by the Fenton reaction and catalytic scavenging activity was assessed by monitoring the EPR signal of the DMPO/•OH adduct in the absence (control) and the presence of 1-7. EPR spectra were recorded every minute, and many of the nanoclusters reached their asymptotic state well before monitoring stopped. The intensity of the second line in the four-line spectrum was plotted vs. time for the Fenton reaction in the absence of nanoclusters (control) and for the Fenton reaction in the presence of 1 mM of each nanocluster (1-7). The results were normalized and are plotted in FIGS. 44A-44C.

Most of the complexes, regardless of size, significantly reduce or completely scavenge all free radicals after one minute. Only complexes 3 and 5 do not efficiently scavenge radicals. Within one minute, in fact, the intensity of the DMPO/HO• adduct signal was reduced to ~0 by 1, 4, and 6 with 2 and 7 taking only slightly longer. This is a dramatic increase in scavenging efficiency compared to CNPs at this ≤20 nm size regime previously investigated by analogous EPR spin-trap techniques:[50] For example, 18 nm CNPs decrease the half-life of the DMPO/HO• adduct from 960 s to 747 s, whereas for 1-3 the half-life is much less than one minute.[14] Similarly, Das et al. monitored the radical scavenging ability by EPR of 3-5 nm CNPs at 1 mM and 10 μM concentrations, showing a decrease in the decay constant for catalysis at 10 μM from 19.4 min to 7.4 min;[49] interestingly, there is little effect at 1 mM, which was assigned to agglomeration of the CNPs. Nanoclusters 1, 2, 4, 6, and 7 thus show higher activities than CNPs, which may be due to a combination of their small size, resulting large surface area, and protection from agglomeration by the surface carboxylate monolayer. Complexes 1, 2, 4, and 6 vary in size (0.54 nm-1.18 nm) showing that for nanoclusters on the nanometer size regime, size may not be an important factor in reactivity.

Figure 44A:
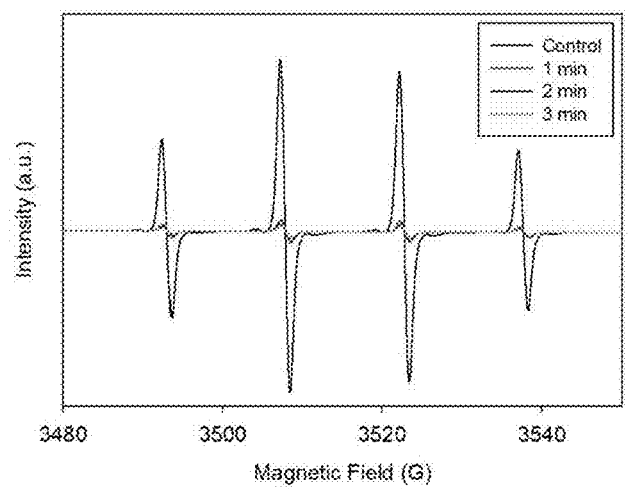
FIGS. 44A-44C are graphs depicting the investigation of catalytic radical scavenging by nanoclusters 1-7.
Figure 44B:
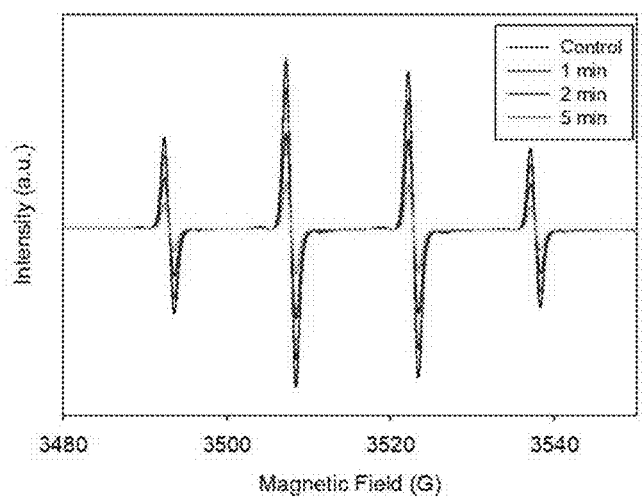
Figure 44C:
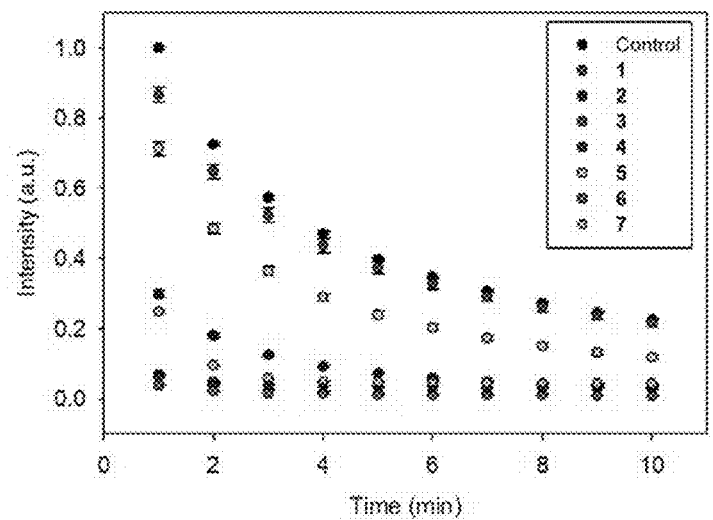
Figure 45A:
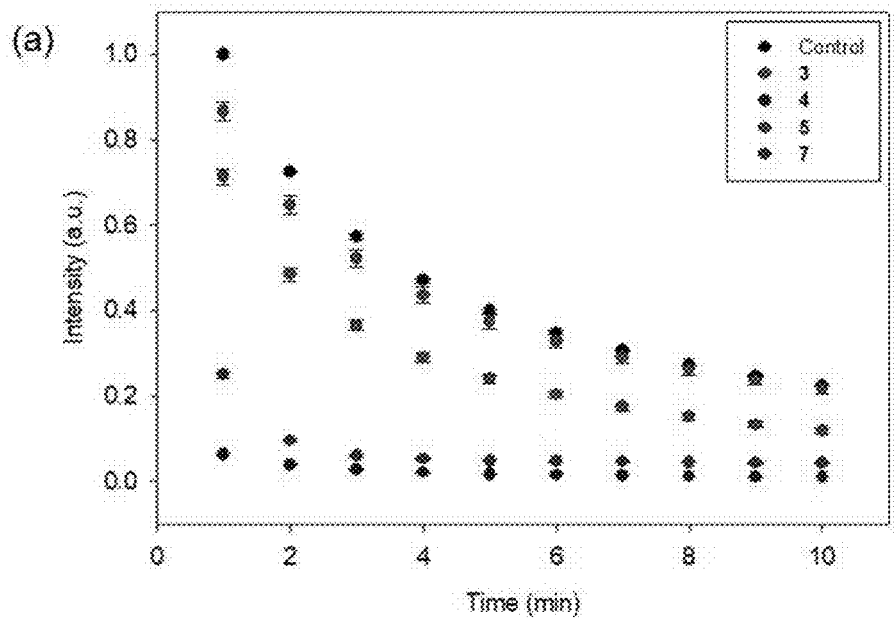
FIGS. 45A-45B represents Plots of signal intensity of the second peak (at ~3506 G) of the DMPO spin-trap adduct in the absence (control) and presence of (a) complexes that contain $Ce^{3+}$ ions (FIG. 45A) and (b) complexes that contain only $Ce^{4+}$ ions (FIG. 45B).
Figure 45B:
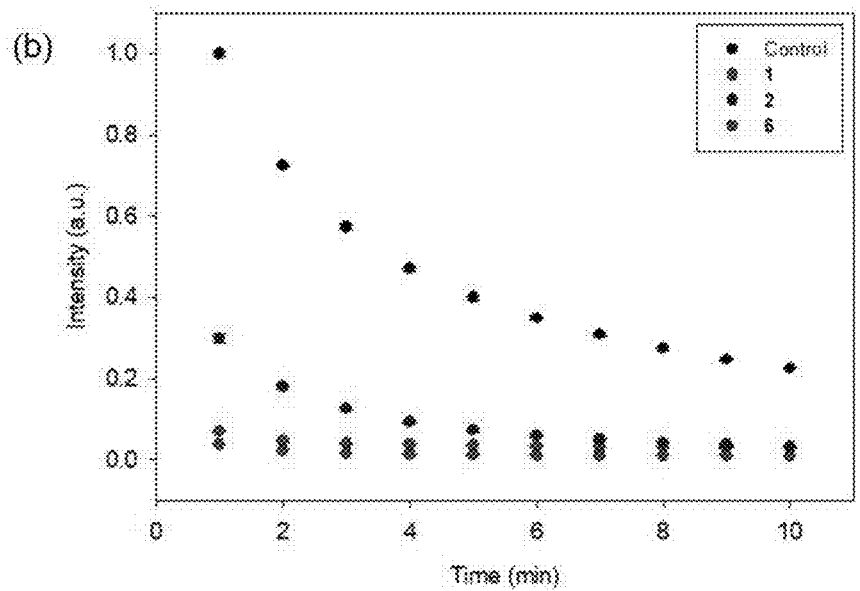

When FIGS. 44A-44C is instead viewed as two separate plots, one for those complexes containing $Ce^{3+}$ ions (3, 4, 5, and 7; FIG. 45A) and those complexes that only contain $Ce^{4+}$ ions (1, 2, and 6; FIG. 45B) a clear trend emerges: for complexes containing $Ce^{3+}$ ions, the higher the $Ce^{3+}/Ce^{4+}$ ratio, the lower the scavenging ability. On the other hand, clusters that only contain $Ce^{4+}$ are effective scavengers, regardless of size. In addition, complexes 4 and 7, which only have two $Ce^{3+}$ ions each, are still efficient radical scavengers since both complexes possess relatively low $Ce^{3+}/Ce^{4+}$ ratios. Complexes that only contain $Ce^{4+}$ all scavenge effectively, regardless of size. This is the first time that exact size and $Ce^{3+}/Ce^{4+}$ ratio has been investigated and relative reactivity compared.

Figure 42:
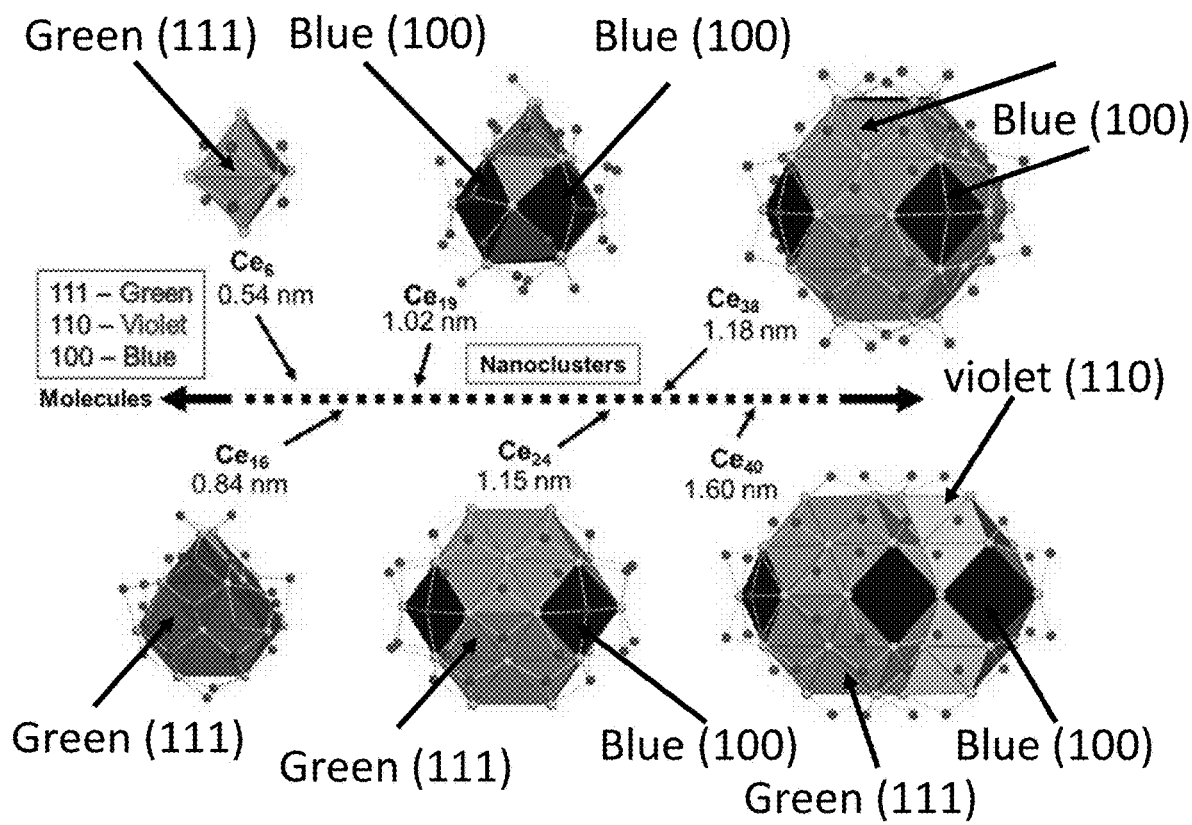
FIG. 42 represents Cores of complexes 1-7 with facets color coded demonstrating their various sizes and $Ce^{3+}/Ce^{4+}$ ratios. Color code: $Ce^{IV}$ gold, $Ce^{III}$ light blue, O red, protonated O (i.e. OH⁻) purple. Only carboxylate O atoms that are bridging are included. C and H have been omitted for clarity. Green surfaces represent the (111) facet, blue surfaces represent the (100) facet and violet surfaces represent the (110) facet. Note that complex 5 has the same topology as 4, but has an additional reduced ion as determined by BVS calculations and EPR measurements
Figure 43:
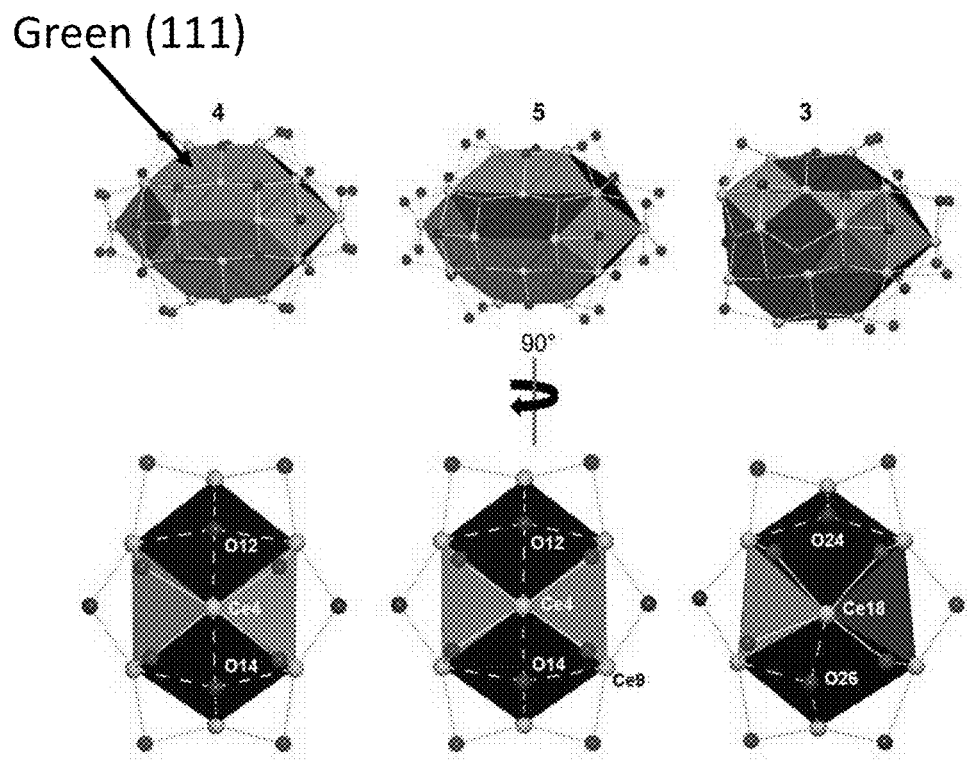
FIG. 43 illustrates the cores of complexes 4, 5, and 3 rotated to view them all in the same "end-on" fashion. For 3 the $\mu_4$-OH⁻ has moved out of the center of the $Ce_4$ square with two $Ce^{3+}$ ions in each square and therefore is now $\mu_3$-OH⁻.. Color code: $Ce^{IV}$ gold, $Ce^{III}$ light blue, O red, OH⁻ purple. Facet colors: (111) facet green, (100) facet blue. Interaction between OH⁻ and surrounding Ce ions indicated by dashed lines.

As shown in FIG. 42, each nanocluster in the Ce/O family possess well-defined facets. Facet-dependent antioxidant ability has been investigated. Zhang et al. synthesized three different morphologies of CNPs: nanoparticles, nanorods, and nanowires and investigated their antioxidant activity.[51] The authors attributed the superior scavenging ability of the nanowires and nanorods to the higher exposure of the (100) and (110) facets on these morphologies than the nanoparticles due to the low vacancy formation energy of the (100) and (110) facets, allowing for efficient $Ce^{3+}/Ce^{4+}$ cycling. Further, they concluded that the nanowires expose a higher ratio of (100)/(110) which results in improved antioxidant ability when compared to nanobars. The size of the particles and $Ce^{3+}$ concentration was determined to be similar for all morphologies and therefore did not contribute to the differences in scavenging ability. With atomically-precise nanoclusters with defined facets and $Ce^{3+}/Ce^{4+}$ ratios, we can probe facet-dependent reactivity. For the nanoclusters, complexes 2-3-2-7 all display the (111) and (100) facets, with 2-7 displaying a (110) facet as well, whereas 2-1 and 2-2 only display (111) facets. Complex 2-6 is fully oxidized, but still possess six (100) facets and efficiently scavenges radicals whereas complexes 2-1 and 2-2 are also fully oxidized, but only possess (111) facets and scavenge radicals as well; 2-1 exhibits almost identical reactivity to 2-6. Finally, as previously mentioned, complexes 2-4 and 2-5 are structurally identical, both displaying the same number and locations of (111) and (100) facets, but only varying in oxidation state (two $Ce^{3+}$ ions for 2-4 vs. three for 2-5), yet they show significantly different scavenging abilities. These results provide support for the conclusion that the antioxidant ability of CNPs is not due to facet-dependent reactivity, but instead is controlled by the $Ce^{3+}/Ce^{4+}$ ratio.

Figure 46A:
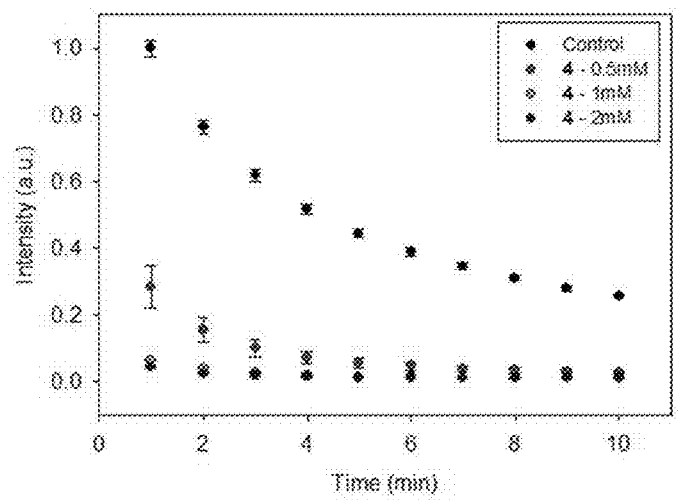
FIGS. 46A-46C shows intensity plots of the DMPO spin-trap adduct in the absence (blank) and presence of (a) complex 4 (FIG. 46A), (b) complex 5 (FIG. 46B), or (c) complex 7 in concentrations of 0.5 mM, 1 mM, and 2 mM (FIG. 46C).
Figure 46B:
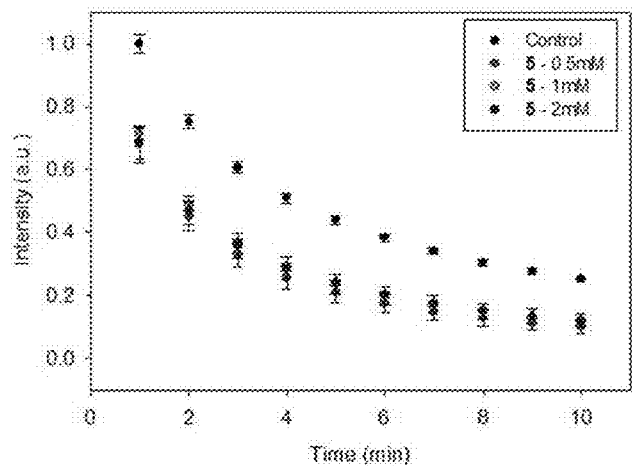
Figure 46C:
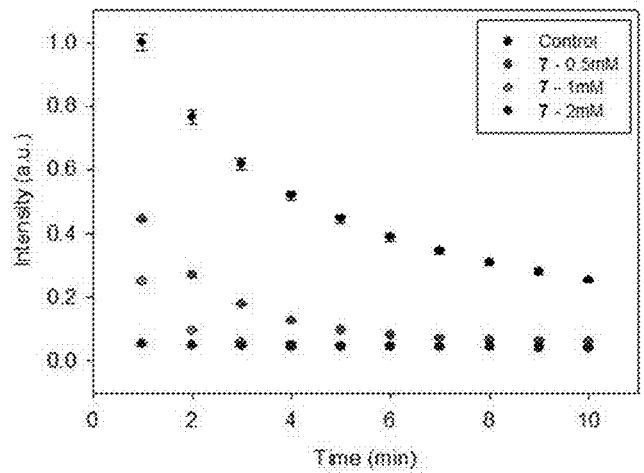

We have addressed size and $Ce^{3+}/Ce^{4+}$ ratio without the occurrence of agglomeration since these nanoclusters are protected by an organic shell that prevents aggregation of the inorganic core. To demonstrate that the nanoclusters do not aggregate, the effect of concentration of a nanocluster on scavenging ability was investigated for complexes 4, 5 and 7 (FIG. 46A-46C). Complexes 4 and 5 were chosen since they only vary in $Ce^{3+}/Ce^{4+}$ ratio, but show different scavenging ability and are not water soluble. 7 was chosen since it is fully water soluble. For 4 and 7, higher concentrations of the nanoclusters result in more radicals scavenged. This suggests that agglomeration is unlikely, as the relative surface area would not be linear with respect to concentration. For 5, since it is not an effective radical scavenger, there are no observable differences in scavenging ability by varying the concentration.

The radical-generating ability of CNPs has been reported, and factors such as synthetic conditions, composition, surface charge, pH, $Ce^{3+}:Ce^{4+}$ ratio, and particle agglomeration have been suggested as possible causes for CNP toxicity.[15, 16, 24, 32, 52] However, due to the difficulty in controlling these properties, exact variables that promote pro- vs anti-oxidant activity by CNPs have not been fully established. Thus it was also explored whether 1-7 in the absence of Fe also possess oxidizing (radical-generating) ability. All of the nanoclusters do show a very weak DMPO/HO• adduct signal in the absence of Fe, confirming their ability to generate OH• in an excess of $H_2O_2$ (FIGS. 49A-49C, FIGS. 50A-50D). However, there does not appear to be a $Ce^{3+}:Ce^{4+}$ ratio dependence on this ability. Further studies with these nanoclusters in which properties such as size and $Ce^{3+}:Ce^{4+}$ ratio are well controlled will continue to shed light on CNPs pro- and anti-oxidant abilities for biomedical applications.

CONCLUSIONS

The family of ultra-small, atomically-precise $CeO_2$ nanoclusters with monolayer organic shells has been expanded with the addition of $Ce_6$ (1), $Ce_{16}$ (2), $Ce_{19}$ (3), and $Ce_{24}$ (5). They all have the fluorite structure of $CeO_2$, as was previously demonstrated by the first members of this family, $Ce_{24}$ (4), $Ce_{38}$ (6), and $Ce_{40}$ (7). This family of nanoclusters now spans a large size range (0.54 nm-1.6 nm) and various $Ce^{3+}:Ce^{4+}$ ratios. Complexes 4 and 5 provide an excellent opportunity for comparison since they possess the same nuclearity and structure, but 5 contains one more reduced ion than 4. Complex 3 represents an important addition to the family since it now possesses the highest $Ce^{3+}:Ce^{4+}$ ratio of this family along with important structural similarities to 4 and 5. These structural similarities have allowed for a careful investigation of structural changes that occur upon reduction of the nanoclusters and continues to further support our conclusion that the $\mu_3$- or $\mu_4$-$OH^-$ groups that cap (100) squares of $Ce_4$ ions represent sites of increased reactivity and possible 0-vacancy sites.

Finally, it was shown that 1, 2, 4, 6 and 7 exhibit high catalytic activity as ROS scavengers at room temperature. The $Ce^{3+}/Ce^{4+}$ ratio was shown to have an impact on the radical scavenging ability of the nanoclusters. Comparing complexes 4 and 5, since they only differ in one reduced ion, complex 4 shows more efficient scavenging than 5, directly suggesting that $Ce^{3+}:Ce^{4+}$ ratio may dictate the radical scavenging ability. Further, those complexes that contain only $Ce^{4+}$ or a low $Ce^{3+}:Ce^{4+}$ ratio outperformed nanoclusters that contain a high $Ce^{3+}:Ce^{4+}$ ratio, regardless of size. There was no evidence for facet-dependent reactivity for the antioxidant ability of Ce/O nanoclusters. Therefore, $CeO_2$ nanoparticles and nanoclusters that contain little or no $Ce^{3+}$ may be more efficient hydroxyl radical scavengers. Higher $Ce^{3+}:Ce^{4+}$ ratios are currently under investigation for other types of ROS, such as superoxide.

TABLE 1

Crystal Data and Structure Refinement Parameters for 1, 2, 3, and 5.

| | 1 · 8MeNO$_2$ | 2 · 15MeCN | 3 · 3.5py · 8MeCN | 5 · 7.5py |
|---|---|---|---|---|
| formula[a] | C$_{116}$H$_{144}$Ce$_6$N$_8$O$_{78}$ | C$_{217.75}$H$_{182}$Ce$_{16}$N$_{15}$O$_{78}$ | C$_{235}$H$_{199}$Ce$_{19}$N$_{14}$O$_{81.50}$ | C$_{267.5}$H$_{215.5}$Ce$_{24}$N$_{11.5}$O$_{96}$ |
| Fw · g mol$^{-1}$ | 3739.10 | 6498.69 | 7185.35 | 8489.88 |
| space group | P$\bar{1}$ | Pa$\bar{3}$ | P2$_1$/n | P2$_1$/n |
| a, Å | 14.8430(9) | 35.4805(7) | 19.7865(11) | 21.8374(17) |
| b, Å | 16.1982(10) | 35.4805(7) | 35.949(2) | 26.302(2) |
| c, Å | 17.5748(11) | 35.4805(7) | 35.343(2) | 24.988(2) |
| α, deg | 64.7932(10) | 90 | 90 | 90 |
| β, deg | 70.8862(11) | 90 | 92.1055(12) | 90.845(2) |
| γ, deg | 71.3192(11) | 90 | 90 | 90 |
| V, Å$^3$ | 3530.6(4) | 44665(3) | 25123(3) | 14351(2) |
| Z | 1 | 8 | 4 | 2 |
| T, K | 100(2) | 100(2) | 100(2) | 100(2) |
| λ, Å[b] | 0.71073 | 0.71073 | 0.71073 | 0.71073 |
| ρ$_{calc}$, g cm$^{-3}$ | 1.759 | 1.933 | 1.900 | 1.939 |
| μ, mm$^{-1}$ | 2.003 | 3.279 | 3.449 | 3.804 |
| R1[c,d] | 0.0277 | 0.0662 | 0.0793 | 0.0938 |
| wR2[e] | 0.0684 | 0.1768 | 0.1885 | 0.2338 |

[a]Including solvent molecules.
[b]Graphite monochromator.
[c]I > 2σ(I).
[d]R1 = 100Σ(||F$_o$| − |F$_c$||)/Σ|F$_o$|.
[e]wR2 = 100[Σ[w(F$_o^2$ − F$_c^2$)$^2$]/Σ[w(F$_o^2$)$^2$]]$^{1/2}$, w = 1/[Σ$^2$(F$_o^2$) + [(ap)$^2$ + bp], where p = [max(F$_o^2$, 0) + 2F$_c^2$]/3.

TABLE S1

Bond Valence Sums and Coordination Numbers (CN) for Ce Atoms in 1.[a,b]

| | Atom | CN | Ce$^{III}$ | Ce$^{IV}$ |
|---|---|---|---|---|
| 1 | Ce1 | 8 | 4.48 | 3.94 |
| | Ce2 | 9 | 4.37 | 3.85 |
| | Ce3 | 9 | 4.38 | 3.86 |

[a]The bold values are the ones closest to the charge for which they were calculated; the oxidation state is thus the nearest integer to the bold value.
[b]CN = coordination number.

TABLE S2

Bond Valence Sums and Assignments for the O Atoms[a] in 1.

| | Atom | BVS | Assignment |
|---|---|---|---|
| 1 | O1 | 1.69 | OH$^-$ |
| | O2 | 1.73 | O$^{2-}$ |
| | O3 | 1.69 | OH$^-$ |
| | O4 | 1.74 | O$^{2-}$ |

[a]An O BVS in the ~1.8-2.0, ~1.0-1.2 and ~0.2-0.4 ranges is indicative of non-, single- and double- protonation, respectively.

TABLE S3

Bond Valence Sums and Coordination Numbers (CN) for Ce Atoms in 2.[a,b]

| | Atom | CN | Ce$^{III}$ | Ce$^{IV}$ |
|---|---|---|---|---|
| 2 | Ce1 | 8 | 4.43 | 3.89 |
| | Ce2 | 8 | 4.54 | 3.99 |
| | Ce3 | 9 | 4.30 | 3.78 |
| | Ce4 | 9 | 4.48 | 3.94 |
| | Ce5 | 9 | 4.39 | 3.85 |
| | Ce6 | 9 | 4.39 | 3.86 |

[a]The bold values are the ones closest to the charge for which they were calculated; the oxidation state is thus the nearest integer to the bold value.
[b]CN = coordination number.

TABLE S4

Bond Valence Sums and Assignments for the O Atoms[a] in 2.

| | Atom | BVS | Assignment |
|---|---|---|---|
| 2 | O1 | 2.13 | O$^{2-}$ |
| | O2 | 1.62 | OH$^-$ |
| | O3 | 1.87 | O$^{2-}$ |
| | O4 | 1.78 | O$^{2-}$ |
| | O5 | 1.73 | O$^{2-}$ |
| | O6 | 2.04 | O$^{2-}$ |
| | O7 | 0.33 | H$_2$O |
| | O8 | 2.16 | O$^{2-}$ |
| | O9 | 1.58 | OH$^-$ |
| | O10 | 2.14 | O$^{2-}$ |
| | O15 | 1.25 | RCO$_2$H |

[a]An O BVS in the ~1.8-2.0, ~1.0-1.2 and ~0.2-0.4 ranges is indicative of non-, single- and double- protonation, respectively.

TABLE S5

Bond Valence Sums and Coordination Numbers (CN) for Ce Atoms in 3.[a,b]

| | Atom | CN | Ce$^{III}$ | Ce$^{IV}$ | Atom | CN | Ce$^{III}$ | Ce$^{IV}$ |
|---|---|---|---|---|---|---|---|---|
| 3 | Ce1 | 8 | 4.11 | 3.61 | Ce11 | 9 | 4.70 | 4.13 |
| | Ce2 | 9 | 3.15 | 2.76 | Ce12 | 9 | 4.33 | 3.81 |
| | Ce3 | 9 | 4.42 | 3.88 | Ce13 | 8 | 4.50 | 3.96 |
| | Ce4 | 9 | 4.36 | 3.83 | Ce14 | 9 | 4.79 | 4.21 |
| | Ce5 | 8 | 4.33 | 3.80 | Ce15 | 9 | 4.28 | 3.76 |
| | Ce6 | 8 | 4.30 | 3.77 | Ce16 | 9 | 4.49 | 3.94 |
| | Ce7 | 9 | 4.37 | 3.84 | Ce17 | 9 | 3.20 | 2.81 |
| | Ce8 | 8 | 4.28 | 3.76 | Ce18 | 9 | 3.20 | 2.81 |
| | Ce9 | 9 | 4.44 | 3.90 | Ce19 | 9 | 3.11 | 2.73 |
| | Ce10 | 9 | 4.39 | 3.86 | | | | |

[a]The bold values are the ones closest to the charge for which they were calculated; the oxidation state is thus the nearest integer to the bold value.
[b]CN = coordination number.

TABLE S6

Bond Valence Sums and Assignments for the O Atoms[a] in 3.

| | Atom | BVS | Assignment |
|---|---|---|---|
| 3 | O1 | 1.97 | $O^{2-}$ |
| | O2 | 1.98 | $O^{2-}$ |
| | O3 | 1.98 | $O^{2-}$ |
| | O4 | 2.10 | $O^{2-}$ |
| | O5 | 2.14 | $O^{2-}$ |
| | O6 | 2.13 | $O^{2-}$ |
| | O7 | 2.12 | $O^{2-}$ |
| | O8 | 2.07 | $O^{2-}$ |
| | O9 | 2.09 | $O^{2-}$ |
| | O10 | 1.99 | $O^{2-}$ |
| | O11 | 2.22 | $O^{2-}$ |
| | O12 | 1.04 | $OH^-$ |
| | O13 | 1.13 | $OH^-$ |
| | O14 | 1.04 | $OH^-$ |
| | O15 | 1.95 | $O^{2-}$ |
| | O16 | 2.07 | $O^{2-}$ |
| | O17 | 1.24 | $OH^-$ |
| | O18 | 2.04 | $O^{2-}$ |
| | O19 | 1.99 | $O^{2-}$ |
| | O20 | 1.98 | $O^{2-}$ |
| | O21 | 1.23 | $OH^-$ |
| | O22 | 2.04 | $O^{2-}$ |
| | O23 | 1.22 | $OH^-$ |
| | O24 | 0.83 | $OH^-$ |
| | O25 | 0.83 | $OH^-$ |
| | O26 | 0.81 | $OH^-$ |
| | O27 | 0.51 | $OH^-$ |
| | O80 | 1.94 | $O^{2-}$ |
| | O81[b] | 0.30 | $H_2O$ |

[a] An O BVS in the ~1.8-2.0, ~1.0-1.2 and ~0.2-0.4 ranges is indicative of non-, single- and double- protonation, respectively.
[b] O81 is disordered with a terminal py, thus confirming O81 to be a neutral $H_2O$ molecule

TABLE S7

Bond Valence Sums and Coordination Numbers (CN) for Ce Atoms in 5.[a, b]

| | Atom | CN | $Ce^{III}$ | $Ce^{IV}$ |
|---|---|---|---|---|
| 5 | Ce1 | 9 | 4.39 | 3.85 |
| | Ce2 | 9 | 4.35 | 3.82 |
| | Ce3 | 9 | 4.35 | 3.82 |
| | Ce4 | 10 | 3.05 | 2.68 |
| | Ce5 | 8 | 4.21 | 3.70 |
| | Ce6 | 8 | 4.49 | 3.94 |
| | Ce7 | 9 | 4.42 | 3.88 |
| | Ce8 | 8 | 4.48 | 3.93 |
| | Ce9 | 9 | 3.99 | 3.51 |
| | Ce10 | 8 | 4.48 | 3.94 |
| | Ce11 | 8 | 4.23 | 3.72 |
| | Ce12 | 9 | 4.44 | 3.90 |

[a] The bold values are the ones closest to the charge for which they were calculated; the oxidation state is thus the nearest integer to the bold value.
[b] CN = coordination number.

TABLE S8

Bond Valence Sums and Assignments for the O Atoms[a] in 5.

| | Atom | BVS | Assignment |
|---|---|---|---|
| 5 | O1 | 1.92 | $O^{2-}$ |
| | O2 | 1.90 | $O^{2-}$ |
| | O3 | 1.87 | $O^{2-}$ |
| | O4 | 2.13 | $O^{2-}$ |
| | O5 | 2.17 | $O^{2-}$ |
| | O6 | 1.97 | $O^{2-}$ |
| | O7 | 2.12 | $O^{2-}$ |
| | O8 | 1.82 | $O^{2-}$ |

TABLE S8-continued

Bond Valence Sums and Assignments for the O Atoms[a] in 5.

| | Atom | BVS | Assignment |
|---|---|---|---|
| | O9 | 2.09 | $O^{2-}$ |
| | O10 | 2.06 | $O^{2-}$ |
| | O11 | 2.13 | $O^{2-}$ |
| | O12 | 0.67 | $OH^-$ |
| | O13 | 1.95 | $O^{2-}$ |
| | O14 | 0.71 | $OH^-$ |
| | O15 | 1.23 | $OH^-$ |
| | O16 | 1.22 | $OH^-$ |
| | O17 | 1.91 | $O^{2-}$ |
| | O19 | 1.64 | $O^{2-}/OH^-$ |

[a] An O BVS in the ~1.8-2.0, ~1.0-1.2 and ~0.2-0.4 ranges is indicative of non-, single- and double- protonation, respectively

TABLE S9

Ce-($\mu_4$-$OH^-$) separations in $Ce^{3+}/3Ce^{4+}$ and Ce-($\mu_3$-$OH^-$) separations in $2Ce^{3+}/2Ce^{4+}$ $4Ce^{4+}$ squares. Distances listed in red do not represent bonds.

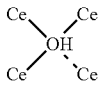

| | Parameter | Distance (Å) |
|---|---|---|
| 4 | Ce1-O12 | 2.843 (6) |
| | Ce2-O12 | 2.674 (5) |
| | Ce3-O12 | 2.669 (5) |
| | Ce4-O12 | 2.724 (6) |
| | Ce4-O14 | 2.990 (6) |
| | Ce7-O14 | 2.600 (5) |
| | Ce9-O14 | 2.681 (5) |
| | Ce12-O14 | 2.721 (6) |
| 5 | Ce1-O12 | 2.745 (10) |
| | Ce2-O12 | 2.697 (10) |
| | Ce3-O12 | 2.625 (10) |
| | Ce4-O12 | 2.909 (10) |
| | Ce4-O14 | 2.75 (1) |
| | Ce7-O14 | 2.659 (10) |
| | Ce9-O14 | 2.684 (10) |
| | Ce12-O14 | 2.812 (10) |

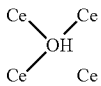

| | Parameter | Distance (Å) |
|---|---|---|
| 3 | Ce10-O24 | 2.474 (14) |
| | Ce12-O24 | 2.638 (13) |
| | Ce17-O24 | 2.592 (13) |
| | Ce18-O24 | 3.587 |
| | Ce15-O26 | 2.487 (14) |
| | Ce16-O26 | 2.654 (13) |
| | Ca18-O26 | 2.595 (13) |
| | Ce19-O26 | 3.542 |
| | Ce11-O25 | 2.632 (12) |
| | Ce14-O25 | 2.456 (13) |
| | Ce19-O25 | 2.601 (13) |
| | Ce17-O25 | 3.574 |

REFERENCES

1 Flytzani-Stephanopoulos, M., Nanostructured Cerium Oxide "Ecocatalysts". *MRS Bulletin* 2001, 26, 885-889.
2 Trovarelli, A., Catalytic Properties of Ceria and $CeO_2$—Containing Materials *Catal. Rev.* 1996, 38, 439-520.
3 Murray, E. P.; Tsai, T.; Barnett, S. A., A direct-methane fuel cell with a ceria-based anode. *Nature* 1999, 400, 649-651.

4 Kharton, V. V.; Figueiredo, F. M.; Navarro, L.; Naumovich, E. N.; Kovalevsky, A. V.; Yaremchenko, A. A.; Viskup, A. P.; Carneiro, A.; Marques, F. M. B.; Frade, J. R., Ceria-based materials for solid oxide fuel cells. *J. Mater. Sci.* 2001, 36, 1105-1117.

5 Sun, C.; Li, H.; Chen, L., Nanostructured ceria-based materials: synthesis, properties, and applications. *Energy Environ. Sci.* 2012, 5, 8475-8505.

6 Reed, K.; Cormack, A.; Kulkarni, A.; Mayton, M.; Sayle, D.; Klaessig, F.; Stadler, B., Exploring the properties and applications of nanoceria: is there still plenty of room at the bottom? *Environ. Sci. Nano* 2014, 1, 390-405.

7 Brayner, R.; Fievet, F.; Coradin, T.; Perullini, M.; Aldabe Bilmes, S.; Jobbagy, M., Cerium Oxide Nanoparticles: Structure, Applications, Reactivity, and Eco-Toxicology. In *Nanomaterials: A Danger or a Promise?*, Springer London: 2012; pp 307-333.

8 Carrettin, S.; Concepción, P.; Corma, A.; López Nieto, J. M.; Puntes, V. F., Nanocrystalline $CeO_2$ Increases the Activity of Au for CO Oxidation by Two Orders of Magnitude. *Angew. Chem. Int. Ed.* 2004, 43, 2538-2540.

9 Tabakova, T.; Boccuzzi, F.; Manzoli, M.; Sobczak, J. W.; Idakiev, V.; Andreeva, D., A comparative study of nanosized IB/ceria catalysts for low-temperature water-gas shift reaction. *Applied Catalysis A: General* 2006, 298, 127-143.

10 Lee, S. S.; Song, W.; Cho, M.; Puppala, H. L.; Nguyen, P.; Zhu, H.; Segatori, L.; Colvin, V. L., Antioxidant Properties of Cerium Oxide Nanocrystals as a Function of Nanocrystal Diameter and Surface Coating. *ACS Nano* 2013, 7, 9693-9703.

11 Das, S.; Dowding, J. M.; Klump, K. E.; McGinnis, J. F.; Self, W.; Seal, S., Cerium oxide nanoparticles: applications and prospects in nanomedicine. *Nanomedicine* 2013, 8, 1483-1508.

12 Walkey, C.; Das, S.; Seal, S.; Erlichman, J.; Heckman, K.; Ghibelli, L.; Traversa, E.; McGinnis, J. F.; Self, W. T., Catalytic properties and biomedical applications of cerium oxide nanoparticles. *Environ. Sci. Nano* 2015, 2, 33-53.

13 Xu, C.; Qu, X., Cerium oxide nanoparticle: a remarkably versatile rare earth nanomaterial for biological applications. *NPG Asia Mater.* 2014, 6, e90.

14 Spulber, M.; Baumann, P.; Liu, J.; Palivan, C. G., Ceria loaded nanoreactors: a nontoxic superantioxidant system with high stability and efficacy. *Nanoscale* 2015, 7, 1411-1423.

15 Nelson, B. C.; Johnson, M. E.; Walker, M. L.; Riley, K. R.; Sims, C. M. Antioxidant Cerium Oxide Nanoparticles in Biology and Medicine. *Antioxidants* 2016, 5, 15.

16 Pulido-Reyes, G.; Rodea-Palomares, I.; Das, S.; Sakthivel, T. S.; Leganes, F.; Rosal, R.; Seal, S.; Fernendez-Pinas, F., Untangling the biological effects of cerium oxide nanoparticles: the role of surface valence states. *Scientific Reports* 2015, 5, 15613.

17 Pirmohamed, T.; Dowding, J. M.; Singh, S.; Wasserman, B.; Heckert, E.; Karakoti, A. S.; King, J. E. S.; Seal, S.; Self, W. T., Nanoceria exhibit redox state-dependent catalase mimetic activity. *Chem. Commun.* 2010, 46, 2736-2738.

18 Karakoti, A. S.; Monteiro-Riviere, N. A.; Aggarwal, R.; Davis, J. P.; Narayan, R. J.; Self, W. T.; McGinnis, J.; Seal, S., Nanoceria as antioxidant: Synthesis and biomedical applications. *JOM* 2008, 60, 33-37.

19 Wason, M. S.; Zhao, J., Cerium oxide nanoparticles: potential applications for cancer and other diseases. *Am. J. Transl. Res.* 2013, 5, 126-131.

20 Gao, Y.; Chen, K.; Ma, J.; Gao, F., Cerium oxide nanoparticles in cancer. *OncoTargets Ther.,* 2014, 7, 835-840.

21 Emerit, J.; Edeas, M.; Bricaire, F., Neurodegenerative Diseases and Oxidative Stress. *Biomed. Pharmacother.* 2004, 58, 39-46.

22 Kim, C. K.; Kim, T.; Choi, I.-Y.; Soh, M.; Kim, D.; Kim, Y.-J.; Jang, H.; Yang, H.-S.; Kim, J. Y.; Park, H.-K.; Park, S. P.; Park, S.; Yu, T.; Yoon, B.-W.; Lee, S.-H.; Hyeon, T., Ceria Nanoparticles that can Protect against Ischemic Stroke. *Angew. Chem. Int. Ed.* 2012, 51, 11039-11043.

23 Kwon, H. J.; Cha, M.-Y.; Kim, D.; Kim, D. K.; Soh, M.; Shin, K.; Hyeon, T.; Mook-Jung, I., Mitochondria-Targeting Ceria Nanoparticles as Antioxidants for Alzheimer's Disease. *ACS Nano* 2016, 10, 2860-2870.

24 Grulke, E.; Reed, K.; Beck, M.; Huang, X.; Cormack, A.; Seal, S., Nanoceria: factors affecting its pro- and antioxidant properties. *Environ. Sci. Nano* 2014, 1, 429-444.

25 Das, M.; Patil, S.; Bhargava, N.; Kang, J.-F.; Riedel, L. M.; Seal, S.; Hickman, J. J., Auto-catalytic Ceria Nanoparticles Offer Neuroprotection to Adult Rat Spinal Cord Neurons. *Biomaterials* 2007, 28, 1918-1925.

26 Chen, J.; Patil, S.; Seal, S.; McGinnis, J. F., Rare earth nanoparticles prevent retinal degeneration induced by intracellular peroxides. *Nat Nano* 2006, 1, 142-150.

27 Tarnuzzer, R. W.; Colon, J.; Patil, S.; Seal, S., Vacancy Engineered Ceria Nanostructures for Protection from Radiation-Induced Cellular Damage. *Nano Lett.* 2005, 5, 2573-2577.

28 Schubert, D.; Dargusch, R.; Raitano, J.; Chan, S.-W., Cerium and yttrium oxide nanoparticles are neuroprotective. *Biochem. Biophys. Res. Commum.* 2006, 342, 86-91.

29 Xu, P. T.; Maidment, B. W.; Antonic, V.; Jackson, I. L.; Das, S.; Zodda, A.; Zhang, X.; Seal, S.; Vujaskovic, Z., Cerium Oxide Nanoparticles: A Potential Medical Countermeasure to Mitigate Radiation-Induced Lung Injury in CBA/J Mice. *Radiation Research* 2016, 185, 516-526.

30 Ouyang, Z.; Mainali, M. K.; Sinha, N.; Strack, G.; Altundal, Y.; Hao, Y.; Winningham, T. A.; Sajo, E.; Celli, J.; Ngwa, W., Potential of using cerium oxide nanoparticles for protecting healthy tissue during accelerated partial breast irradiation (APBI). *Physica Medica* 2016, 32, 631-635.

31 Alpaslan, E.; Yazici, H.; Golshan, N. H.; Ziemer, K. S.; Webster, T. J., pH-Dependent Activity of Dextran-Coated Cerium Oxide Nanoparticles on Prohibiting Osteosarcoma Cell Proliferation. *ACS Biomater. Sci. Eng.* 2015, 1, 1096-1103.

32 Ni, P.; Wei, X.; Guo, J.; Ye, X.; Yang, S., On the origin of the oxidizing ability of ceria nanoparticles. *RSC Adv.* 2015, 5, 97512-97519.

33 Xue, Y.; Luan, Q.; Yang, D.; Yao, X.; Zhou, K., Direct Evidence for Hydroxyl Radical Scavenging Activity of Cerium Oxide Nanoparticles. *J. Phys. Chem. C,* 2011, 115, 4433-4438.

34 Lu, M.; Zhang, Y.; Wang, Y.; Jiang, M.; Yao, X., Insight into Several Factors that Affect the Conversion between Antioxidant and Oxidant Activities of Nanoceria. *ACS Appl. Mater. Interfaces,* 2016, 8, 23580-23590.

35 Asati, A.; Santra, S.; Kaittanis, C.; Nath, S.; Perez, J. M., Oxidase-Like Activity of Polymer-Coated Cerium Oxide Nanoparticles. *Angew. Chem. Int. Ed.* 2009, 48, 2308-2312.

36 Bruker-AXS: Madison, WI, USA, 2013.

37 SHELXTL2013 (2013). Bruker-AXS, Madison, Wisconsin, USA.

38 SHELXTL2014 (2014). Bruker-AXS, Madison, Wisconsin, USA.
39 P. van der Sluis & A. L. Spek (1990). SQUEEZE, *Acta Cryst. A* 46, 194-201.
40 Spek, A. L. (2009). PLATON, *Acta Cryst. D* 65, 148-155.
41 Mereacre, V.; Ako, A. M.; Akhtar, M. N.; Lindemann, A.; Anson, C. E.; Powell, A. K., Homo- and Heterovalent Polynuclear Cerium and Cerium/Manganese Aggregates. *Helv. Chim. Acta.* 2009, 92, 2507-2524.
42 Das, R.; Sarma, R.; Baruah, J. B., A hexanuclearcerium (IV) clusterwith mixed coordination environment. *Inorg. Chem. Commun.* 2010, 13, 793-795.
43 Hennig, C.; et. al, Crystal Structure and Solution Species of Ce(III) and Ce(IV) Formates: From Mononuclear to Hexanuclear Complexes, *Inorg. Chem.* 2013, 52, 11734-11743.
44 Calvez, G.; Daiguebonne, C.; Guillou, O.; Le Dret, F., A New Series of Anhydrous Lanthanide-Based Octahedral Hexanuclear Complexes. *Eur. J. Inorg. Chem.* 2009, 2009, 3172-3178.
45 Mathey, L.; Paul, M.; Coperet, C.; Tsurugi, H.; Mashima, K. Cerium(IV) Hexanuclear Clusters from Cerium(111) Precursors: Molecular Models for Oxidative Growth of Ceria Nanoparticles. *Chem. Eur. J.* 2015, 21, 13454-13461.
46 Estes, S. L.; Antonio, M. R.; Soderholm, L., Tetravalent Ce in the Nitrate-Decorated Hexanuclear Cluster $[Ce_8(\mu_3\text{-}O)_4(\mu_3\text{-}OH)_4]^{12+}$: A Structural End Point for Ceria Nanoparticles. *J. Phys. Chem. C* 2016, 120, 5810-5818.
47 Das, S. et al. Cerium oxide nanoparticles: applications and prospects in nanomedicine. *Nanomedicine* 8, 1483-1508 (2013).
48 Xu, C. & Qu, X. Cerium oxide nanoparticle: a remarkably versatile rare earth nanomaterial for biological applications. *NPG Asia Mater* 6, e90 (2014).
49 Babu, S., Velez, A., Wozniak, K., Szydlowska, J. & Seal, S. Electron paramagnetic study on radical scavenging properties of ceria nanoparticles. *Chem. Phys. Lett.* 442, 405-408 (2007).
50 Schlick, S., Danilczuk, M., Drews, A. R. & Kukreja, R. S. Scavenging of Hydroxyl Radicals by Ceria Nanoparticles: Effect of Particle Size and Concentration. *J. Phys. Chem. C* 120, 6885-6890, (2016).
51 Zhang, Y.; Zhou, K.; Zhai, Y.; Qin, F.; Pan, L.; Yao, X. Crystal plane effects of nano-$CeO_2$ on its antioxidant activity. *RSC Adv.* 2014, 4, 50325-50330.
52 Gagnon, J.; Fromm, K. M. Toxicity and Protective Effects of Cerium Oxide Nanoparticles (Nanoceria) Depending on Their Preparation Method, Particle Size, Cell Type, and Exposure Route. *Eur. J. Inorg. Chem.* 2015, 2015, 4510-4517.

Unless defined otherwise, all technical and scientific terms used have the same meaning as commonly understood by one of ordinary skill in the art to which this disclosure belongs. Although any methods and materials similar or equivalent to those described can also be used in the practice or testing of the present disclosure, the preferred methods and materials are now described.

Embodiments of the present disclosure will employ, unless otherwise indicated, techniques of separating, testing, and constructing materials, which are within the skill of the art. Such techniques are explained fully in the literature.

It should be emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

At least the following is claimed:

1. A method of treating oxidative stress in a subject in need thereof, comprising:
   delivering, to a subject in need thereof, a pharmaceutical composition, wherein the pharmaceutical composition includes a therapeutically effective amount of a compound, or a pharmaceutically acceptable salt of the compound, and a pharmaceutically acceptable carrier, to treat the oxidative stress,
   wherein the compound comprises one or more molecular cerium-oxide nanocluster with cerium nuclearity of from 19 to 100 and having the formula $[Ce_xO_y(OH)_w(H_2O)_l(RCO_2)_z(L)_m]^n$, $Ce_xO_y(OH)_w(H_2O)_l(RPO_2)_z(L)_m]^n$ or $[Ce_xO_y(OH)_w(H_2O)_l(RPO_3)_z(L)_m]^n$, wherein x is from 19 to 100, wherein y is an integer number greater than 0, wherein l, m, n, w, z are 0 or an integer number, wherein R is selected from the group consisting of phenyl (Ph), $CH_3$, $CH_3CH_2$, an aromatic group, a polyaromatic group, a substituted phenyl, a polyphenyl group, a linear or branched aliphatic groups, a substituted linear or branched aliphatic group, a linear or branched alicyclic group, and combinations thereof, wherein L is one or more neutral organic molecules, wherein the molecular cerium-oxide nanocluster composition has a ratio of $Ce^{3+}/Ce^{4+}$ of from 0.01 to 0.5.

2. The method of claim 1, wherein L is $CH_3CN$ or pyridine (py).

3. The method of claim 1, wherein the molecular cerium-oxide nanocluster has a formula of $Ce_{19}O_{18}(OH)_9(PhCO_2)_{27}(py)_3$ ($H_2O$), $Ce_{24}O_{36-x-y}(OH)_x(H_2O)_y(PhCO_2)_{30}(py)_4$, $Ce_{38}O_{62-x-y}(OH)_x(H_2O)_y(CH_3CH_2CO_2)_{36}(py)_8$, or $Ce_{40}O_{56}(OH)_x(H_2O)_{2-x}(CH_3CO_2)_{46-y}(py)_4(CH_3CN)_y$.

4. The method of claim 1, wherein the composition comprises one or more of $Ce_6O_4(OH)_4(H_2O)_4(dmb)_{12}$, $Ce_{16}O_{17}(OH)_6(O_2CPh)_{24}(HO_2CPh)_3(H_2O)$, $Ce_{19}O_{18}(OH)_{10}(O_2CPh)_{26}(H_2O)(py)_3$, $Ce_{24}O_{27}(OH)_9(O_2CPh)_{30}(py)_4$, $Ce_{24}O_{28}(OH)_8(PhCO_2)_{30}(py)_4$, or $Ce_{38}O_{54}(OH)_8(CH_3CH_2O_2)_{36}(py)_8$, and wherein dmb defines an anion of dimethoxybenzoic acid.

5. The method of claim 1, wherein treating oxidative stress comprises scavenging reactive oxygen species.

6. The method of claim 1, wherein the molecular cerium-oxide nanocluster composition has a ratio of $Ce^{3+}/Ce^{4+}$ of from 0.1 to 0.21.

7. The method of claim 1, wherein x is from 19 to 40.

8. The method of claim 1, wherein x is 19, 24, 38, or 40.

9. The method of claim 1, wherein x is 19, 38, or 40.

* * * * *